United States Patent
Bake et al.

(10) Patent No.: US 10,377,907 B2
(45) Date of Patent: Aug. 13, 2019

(54) SUBSTRATE WITH A SUPERHYDROPHOBIC COATING AND A METHOD OF FABRICATING THEREOF

(71) Applicant: King Fahd University of Petroleum and Minerals, Dhahran (SA)

(72) Inventors: Abuduliken Bake, Dhahran (SA); Nesar Merah, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/806,989

(22) Filed: Nov. 8, 2017

(65) Prior Publication Data
US 2019/0136073 A1    May 9, 2019

(51) Int. Cl.
C09D 5/16 (2006.01)
H01L 31/0216 (2014.01)
C07F 7/02 (2006.01)
C07F 7/14 (2006.01)
C07F 7/18 (2006.01)

(52) U.S. Cl.
CPC ............ *C09D 5/1681* (2013.01); *C07F 7/025* (2013.01); *C07F 7/14* (2013.01); *C07F 7/1804* (2013.01); *H01L 31/02167* (2013.01)

(58) Field of Classification Search
None
See application file for complete search history.

(56) References Cited

U.S. PATENT DOCUMENTS

| | | | |
|---|---|---|---|
| 3,702,783 A * | 11/1972 | Hartlein | C03C 17/30 427/215 |
| 9,675,994 B2 | 6/2017 | Schoenfisch et al. | |
| 2002/0127415 A1* | 9/2002 | Standke | C08J 7/12 428/447 |
| 2008/0113188 A1* | 5/2008 | Shah | C08J 7/04 428/336 |
| 2009/0061199 A1* | 3/2009 | Egami | C09D 183/02 428/304.4 |
| 2013/0034653 A1* | 2/2013 | Kumar | B05D 5/06 427/162 |

(Continued)

FOREIGN PATENT DOCUMENTS

WO    2009/029979    3/2009

OTHER PUBLICATIONS

Plueddemann, E. P. (Silane Coupling agents, Chapter 2, Springer Science and Business Media, New York, 1991, pp. 31-54; CSA), (Year: 1991).*

(Continued)

Primary Examiner — Francisco W Tschen
(74) Attorney, Agent, or Firm — Oblon, McClelland, Maier & Neustadt, L.L.P.

(57) ABSTRACT

A substrate with a superhydrophobic coating, wherein the superhydrophobic coating includes a binding layer disposed on the substrate, and a hydrophobic layer disposed on the binding layer, wherein the hydrophobic layer includes perfluoroalkyl-functionalized silica nanoparticles, and a method of fabricating the substrate with the superhydrophobic coating. Various combinations of embodiments of the substrate with the superhydrophobic coating and the method of fabricating thereof are provided.

16 Claims, 43 Drawing Sheets

(56) References Cited

U.S. PATENT DOCUMENTS

2017/0174928 A1* 6/2017 Sigmund .............. C09D 127/18
2017/0267576 A1* 9/2017 Sigmund ................. C09D 7/62

OTHER PUBLICATIONS

Manca et al. Durable Superhydrophobic and Antireflective Surfaces by Trimethylsilanized Silica Nanoparticles-Based Sol-Gel Processing, Langmuir 2009, 25(11), 6357-6362 (Year: 2009).*
Spray, https://www.spray.com/Literature_PDFs/TM410B_Optimizing_Your_Spray_System.pdf, Retrieved on Nov. 16, 2018; Available Online Dec. 12, 2013 (Year: 2013).*
Lihui Xu et al., "Facile preparation of superhydrophobic polyester surfaces with fluoropolymer/SiO nanocomposites based on vinyl nanosilica hydrosols," Journal of Applied Polymer Science, vol. 131, No. 11, Jan. 9, 2014, 2 Pages.
Jun Liang et al., "Transformation of hydrophilic cotton fabrics into superhydrophobic surfaces for oil/water separation," The Journal of The Textile Institute, vol. 103, No. 3, Sep. 17, 2012, 5 Pages.
G. Gu et al., "Fabrication and characterization of transparent superhydrophobic thin films based on silica nanoparticles," Applied Physics, vol. 83, No. 1, Jan. 17, 2006, 3 Pages.
Masaya Hikita et al., "Super-Liquid-Repellent Surfaces Prepared by Colloidal Silica Nanoparticles Covered with Fluoroalkyl Groups," Langmuir, vol. 21, No. 16, Jul. 9, 2005, pp. 7299-7302.

* cited by examiner

Fig. 5
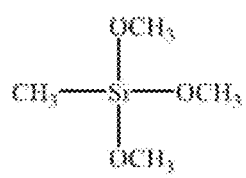
(a) MTMS
(b) GLYMO
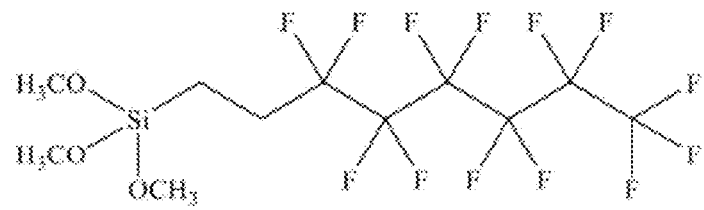
(c) PFOTS

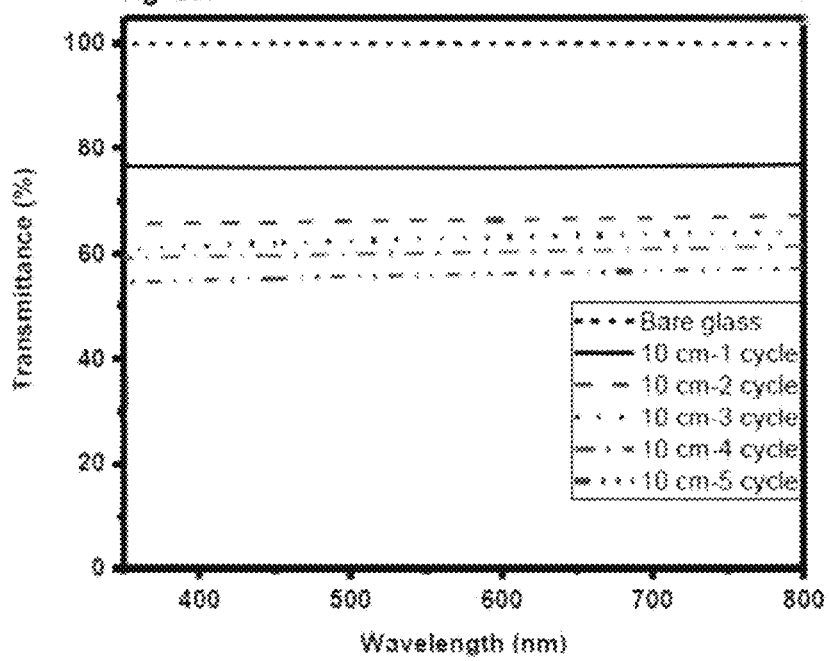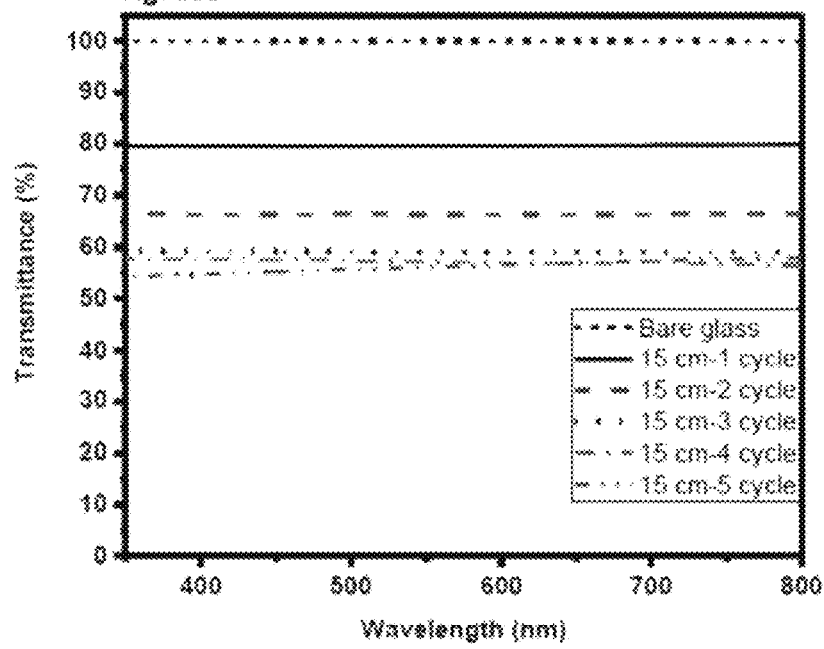

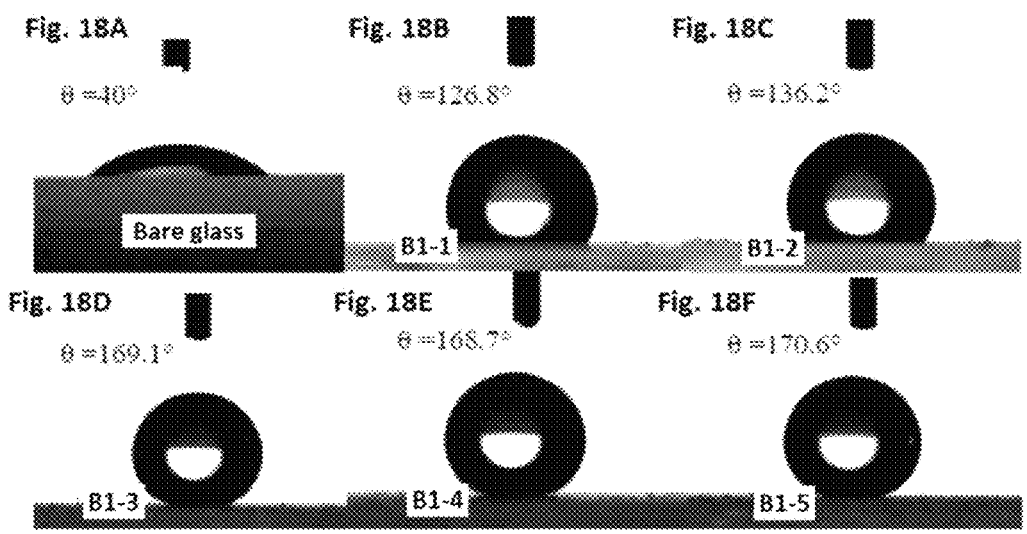

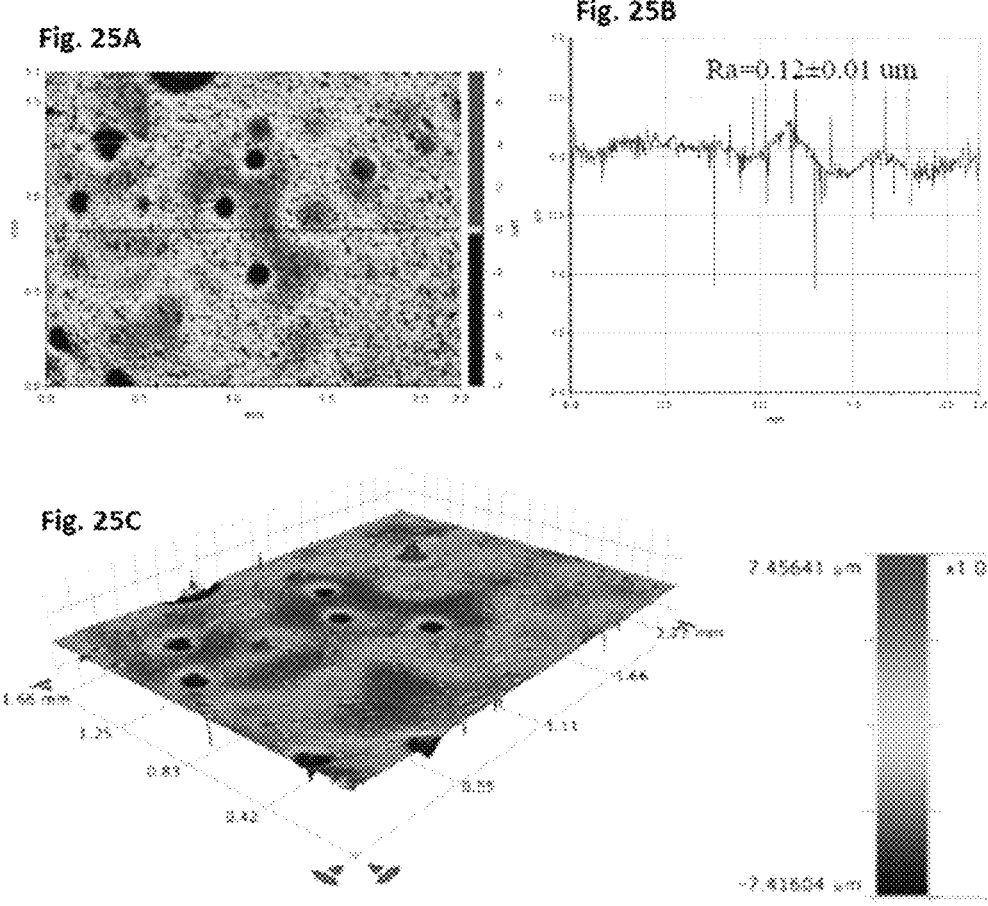

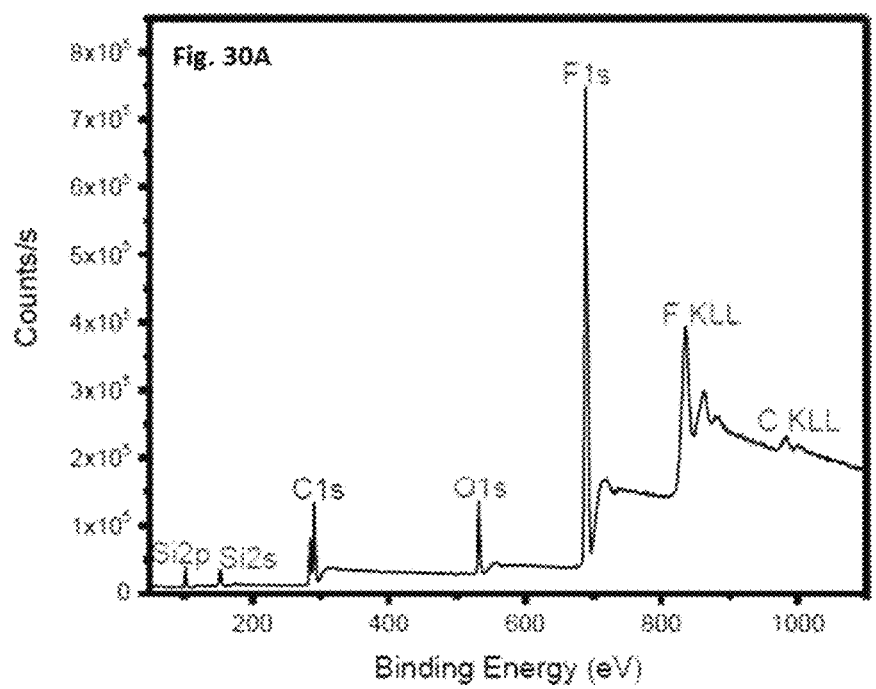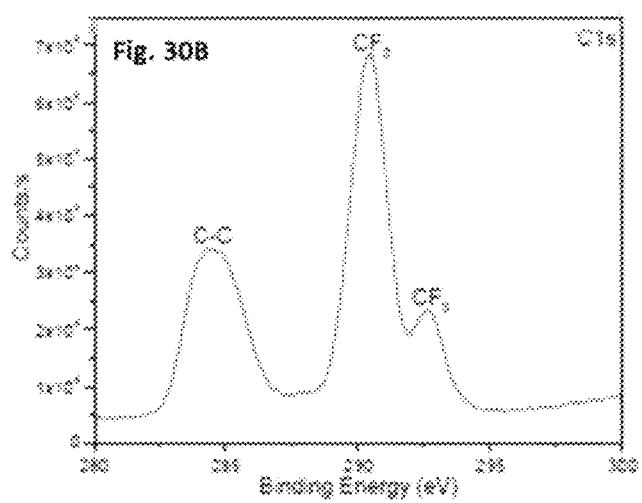

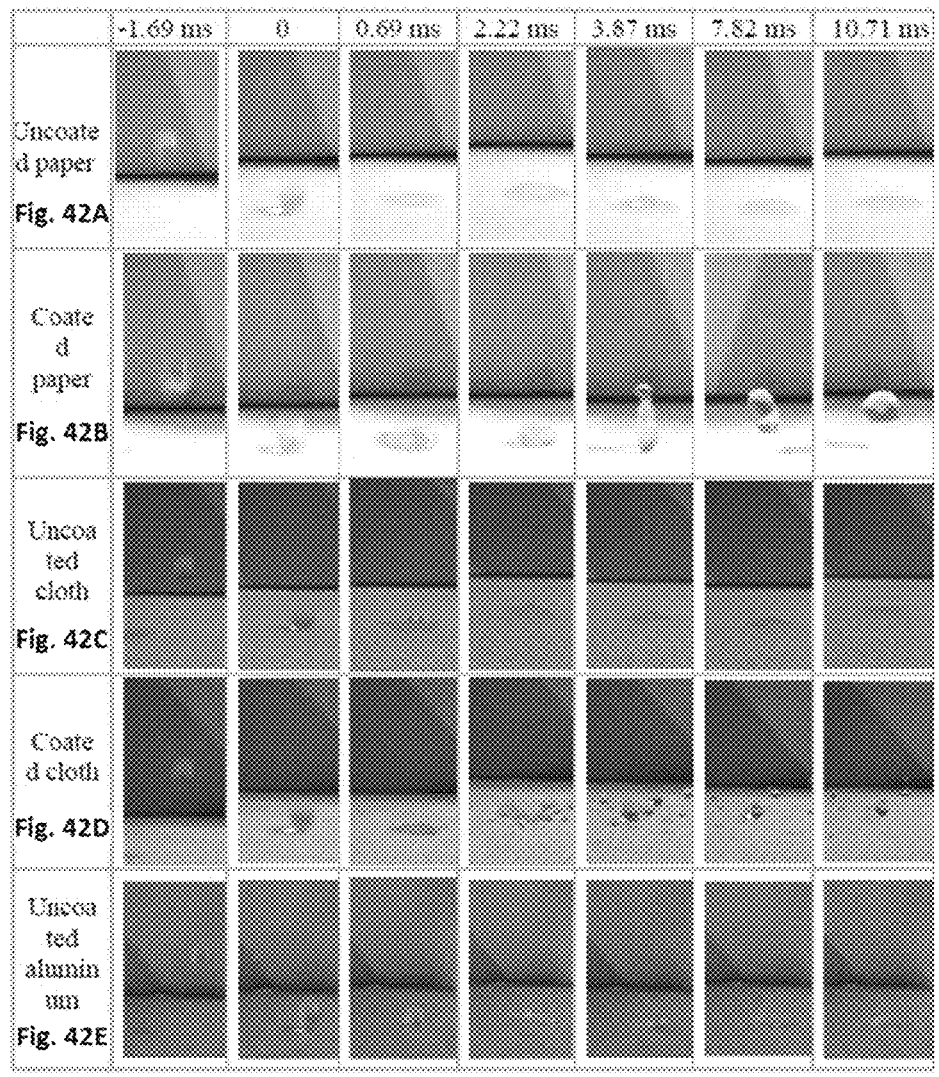

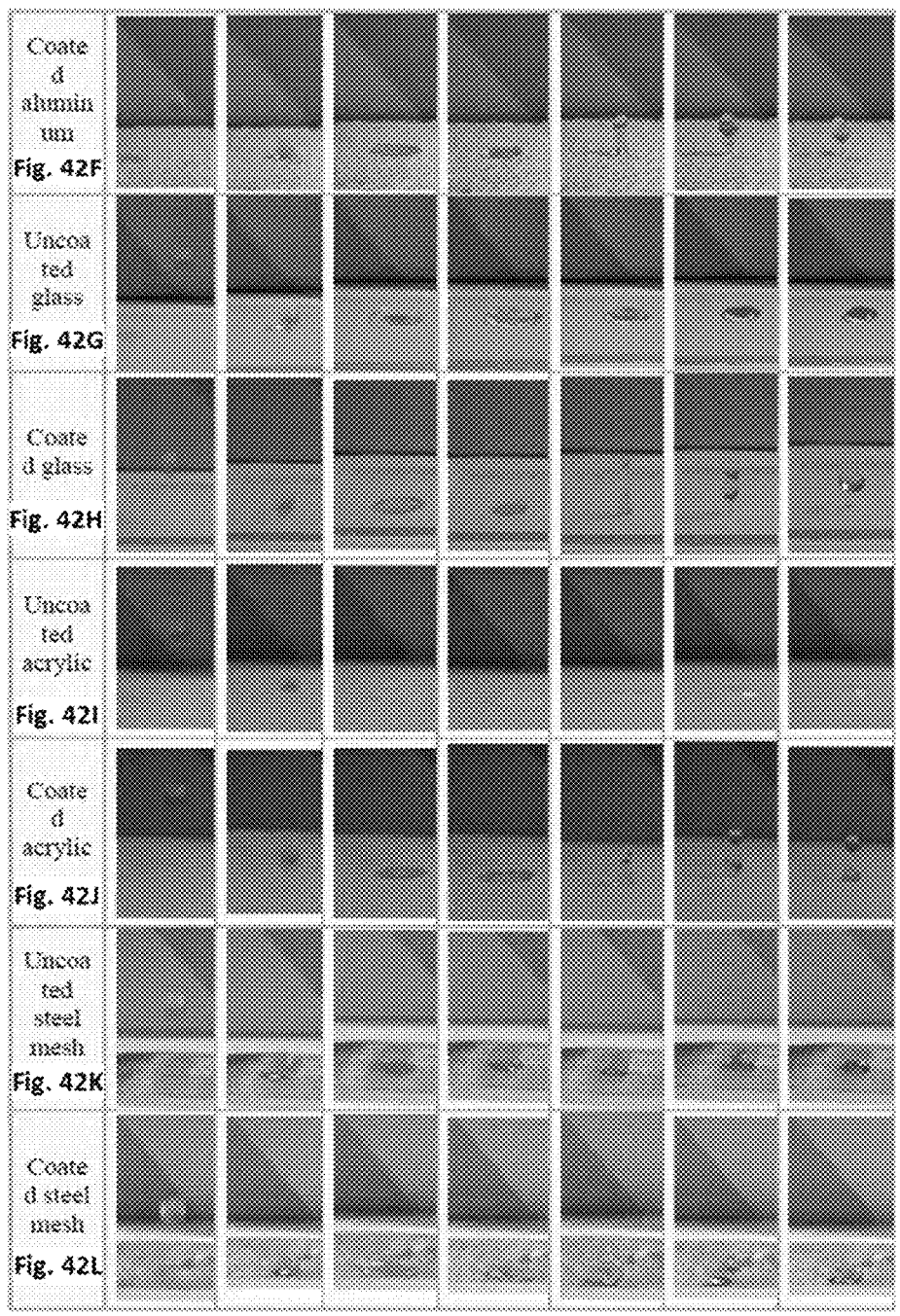

SUBSTRATE WITH A SUPERHYDROPHOBIC COATING AND A METHOD OF FABRICATING THEREOF

STATEMENT REGARDING PRIOR DISCLOSURES BY THE INVENTOR OR A JOINT INVENTOR

Abuduliken Bake, *Development of mechanically robust water-repellent surfaces*, M. Sc. Dissertation, King Fahd University of Petroleum and Minerals, January 2017, which is incorporated by reference in its entirety.

BACKGROUND OF THE INVENTION

Technical Field

The present invention relates to a substrate with a superhydrophobic coating and a method of fabricating thereof, wherein the superhydrophobic coating includes a binding layer disposed on the substrate and a hydrophobic layer disposed on the binding layer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Green and sustainable energy development has become a popular research area worldwide in the past few years, due to the major effects of green energy on environmental issues. Solar energy conversion is considered one major source of green energy, and devices such as photovoltaic (PV) panels can convert the solar radiation to electricity. Current ongoing research on solar energy is mostly dedicated towards minimizing costs and improving the efficiency of solar cells. Current Si-based solar modules provide a solar conversion efficiency of up to 25%. See M. A. Green, K. Emery, Y. Hishikawa, W. Warta, and E. D. Dunlop, "Solar cell efficiency tables (Version 45)," *Prog. Photovoltaics Res. Appl.*, vol. 23, no. 1, pp. 1-9, January 2015; and M. A. Green, "The path to 25% silicon solar cell efficiency: History of silicon cell evolution," *Prog. Photovoltaics Res. Appl.*, vol. 17, no. 3, pp. 183-189, 2009. However, maintaining solar cells to provide such efficiencies over an extended period of time is a challenging issue.

One main challenge to maintain the solar conversion efficiency within preferable high ranges is to keep the solar and photovoltaic (PV) panels as clean as possible. This is a daunting task, particularly in desert regions where the solar radiation is abundant but dust accumulation is inevitable. Accumulation and deposition of dust particles on the solar PV panels is a complicated process which is mainly governed by the weather conditions at the installation place. Dust deposition is mainly influenced by the characteristics of the dust particles, the surfaces of the panels, and environmental factors. Dust particles and other particulates can lead to a substantial reduction of efficiency in PV modules. Research conducted by Salim et al. found that PV system in a solar-village near Riyadh, Saudi Arabia reduced solar conversion efficiency of a PV panel by about 32% after 8 months of dust accumulation on the PV panels. See A. A. Salim, F. S. Huraib, and N. N. Eugenio, "PV power-study of system options and optimization," in *EC photovoltaic solar conference.* 8, 1988, pp. 688-692. A similar study conducted by Wakim in Kuwait revealed an efficiency reduction of about 17% after 6 days. See F. Wakim, "Introduction of PV power generation to Kuwait," *Kuwait Inst. Sci. Res. Kuwait City,* 1981. Sometimes the actual reduction of efficiency may be much more significant within a short period of time. In the regions with humid climates, PV solar panels may recover a portion of the efficiency loss after a rainfall. See F. Mejia, J. Kleissl, and J. L. Bosch, "The Effect of Dust on Solar Photovoltaic Systems," *Energy Procedia*, vol. Complete, no. 49, pp. 2370-2376, 2014.

A number of techniques have been developed to keep the surface free of mud and dust or to minimize the dust settlement on PV panel surfaces, in order to facilitate the harvesting of solar energy by PV panels. These techniques include cleaning the PV panel surfaces by high-pressure water fluids, mechanical methods (such as cleaning with mechanical robotic brushes and vibration), electrostatic removal of dusts and fabricating surfaces with self-cleaning properties. See G. He, C. Zhou, and Z. Li, "Review of Self-Cleaning Method for Solar Cell Array," *Procedia Eng.*, vol. 16, pp. 640-645, 2011; R. B. Williams, R. Tanimoto, A. Simonyan, and S. Fuerstenau, "Vibration Characterization of Self-Cleaning Solar Panels with Piezoceramic Actuation," 48*th AIAA/ASME/ASCE/AHS/ASC Struct. Struct. Dyn. Mater. Conf.,* 2007; P. E. Clark, S. A. Curtis, F. A. Minetto, and J. Keller, "Finding a Dust Mitigation Strategy that Works on the Lunar Surface," *Lunar Planet. Sci.,* 2007; C. Callea, C. R. Buhler, J. L. Mcfalib, and S. J. Snyder, "Particle Removal by Electrostatic and Dielectrophoretic Forces for Dust Control During Lunar Exploration Missions," *J. Electrostat.,* 2009. These techniques do not require intensive labor work and/or consume huge amounts of water and energy, thus save time, money, and water.

Modifying a PV panel surface to make it superhydrophobic with self-cleaning properties is a practical way of maintaining solar PV panels to prevent losses in efficiency. On a superhydrophobic surface, water droplets roll off the surface at a very small tilting angle or even without tilting, thereby collecting dust and dirt particles, and leaving behind a clean and dry surface. Hence, the development of superhydrophobic surfaces has been the focus of some research studies for applications in photovoltaic (PV) panels, frictionless transport of water through pipes with less energy consumptions, etc. See A. V. Rao, M. M. Kulkarni, D. P. Amalnerkar, and T. Seth, "Superhydrophobic silica aerogels based on methyltrimethoxysilane precursor," *J. Non. Cryst. Solids*, vol. 330, no. 1-3, pp. 187-195, 2003. In addition, researchers have been successful in combining several desirable characteristics such as self-cleaning, optical transparency, etc. in one product. See H. Budunoglu, A. Yildirim, M. O. Guler, and M. Bayindir, "Highly Transparent, Flexible, and Thermally Stable Superhydrophobic ORMOSIL Aerogel Thin Films," *ACS Appl. Mater. Interfaces*, vol. 3, no. 2, pp. 539-545, February 2011; S. L. Dhere, S. S. Latthe, C. Kappenstein, G. M. Pajonk, V. Ganesan, A. V. Rao, P. B. Wagh, and S. C. Gupta, "Transparent water repellent silica films by sol-gel process," *Appl. Surf. Sci.,* vol. 256, no. 11, pp. 3624-3629, 2010; Q. Feng, J. N. Wang, and K. D. Sanderson, "Organic Inorganic Composite," vol. 4, no. 4, pp. 2201-2209, 2010; S. Liu, X. Liu, S. S. Latthe, L. Gao, S. An, S. S. Yoon, B. Liu, and R. Xing, "Self-cleaning transparent superhydrophobic coatings through simple sol-gel processing of fluoroalkylsilane," *Appl. Surf. Sci.*, vol. 351, pp. 897-903, 2015; P. G. Parejo, M. Zayat, and D. Levy, "Highly efficient UV-absorbing thin-film coatings for protection of organic materials against photodegradation," *J. Mater. Chem.*, vol. 16, no. 22, p. 2165, 2006; R. Taurino, E. Fabbri, D. Pospiech, A. Synytska, and M. Messori, "Preparation of scratch resistant superhydrophobic hybrid coatings by sol-gel process," *Prog. Org. Coatings*, vol. 77, no. 11, pp. 1635-1641, 2014.

In addition to water-repellency and self-cleaning properties, some other properties of the coatings should be considered as well, for example, high transmittance of visible light, antireflection index, etc. Usually, the surface chemistry and the surface roughness of a material determine the surface hydrophobicity of that material. Accordingly, low surface energy chemistry and a preferred level of surface roughness may result in a superhydrophobic surface. The surface roughness and the transmittance are contradictory properties, such that an increase in the surface roughness reduces the transmittance and vice versa. Therefore, a balance between the surface roughness and the transmittance of a material should be tuned properly depending on the applications of that material. On the other hand, the superhydrophobic materials should be able to sustain harsh environments, and therefore mechanical stability/robustness and ultraviolet (UV) resistance should be considered as well. Xiu et al. revealed that the superhydrophobic coatings usually wear due to abrasion and continuous erosion by dust particles, which may result in a reduction of the surface water repelling properties. See Y. Xiu, Y. Liu, B. Balu, D. W. Hess, and C. Wong, "Robust superhydrophobic surfaces prepared with epoxy resin and silica nanoparticles," *IEEE Trans. Components, Packag. Manuf. Technol.*, vol. 2, no. 3, pp. 395-401, 2012.

A number of variables need to be determined in order to characterize a supcrhydrophobic surface of a material and to be able to fabricate a water-repellent surface with a self-cleaning characteristic. Among these variables, water contact angle, surface roughness, and surface energy are the most important ones. Water contact angle measurement is a method that can be used for qualitatively determination of the surface free energy of the substances. Water contact angle refers to the angle formed by the intersection of the liquid-solid interface and the liquid-vapor interface as illustrated by the angle α in the FIG. 1(*a*). Water contact angle of a hydrophilic surface is less than 900, this value is higher than 900 for hydrophobic surfaces. Superhydrophobic surfaces generally provide a water contact angle of higher than 130°, preferably higher than 1500. Water contact angle measurement is generally determined with goniometers. In actual applications, measurement of static contact angle alone to characterize wetting behavior is not enough, and other parameters such as advancing contact angle $α_a$ and the receding contact angle $α_r$ should be determined. The contact angles formed by expanding and contracting the liquid droplet or by the motion of the liquid droplet is referred to as the advancing contact angle $α_a$ and the receding contact angle $α_r$, respectively, schematic illustration is showed in FIG. 1(*b*). The difference between the advancing angle and the receding angle is called the hysteresis (H), which is a parameter that determines the hydrophobicity of a surface. See G. Bracco and B. Hoist, *Surface science techniques*, vol. 51, no. 1. 2013. In general, low hysteresis can contribute to the hydrophobicity and self-cleaning effect, but surfaces with high advancing angle and low receding angle may show poor hydrophobicity and leave water drops "pinned" onto the surface. See J. P. Youngblood and T. J. McCarthy, "Ultrahydrophobic polymer surfaces prepared by simultaneous ablation of polypropylene and sputtering of poly (tetrafluoroethylene) using radio frequency plasma," *Am. Chem. Soc. Polym. Prepr. Div. Polym. Chem.*, vol. 40, no. 2, pp. 563-564, 1999.

Water droplets of specific size can be used to evaluate the surface adhesion from the measurement of the sliding angle, which is the angle needed for a droplet to start sliding down from a tilted surface. Wolfram et al. described a relationship between the amount of force required for a droplet start to sliding on the solid surface and a sliding angle. See E. Wolfram, R. Faust, and J. Padday, "Wetting, spreading and adhesion," J F Padday, Ed, 1978.

Generally, on rough and heterogeneous surfaces, water droplets can exist in two kinds of equilibrium states, the Cassie-Baxter state and the Wenzel state, which are illustrated in FIG. 2. See A. Cassie, "40, 546 (1944): S. Baxter, ABD Cassie," *J. Text. Inst*, 1945; and R. N. Wenzel, "Resistance of Solid Surfaces to Wetting by Water," *Ind. Eng. Chem.*, vol. 28, no. 8, pp. 988-994, August 1936. According to a simulation done by Johnson and Dettre, with increasing surface roughness the dominant hydrophobicity mode is continuously transformed from Wenzel state to Cassie-Baxter state. See R. E. Johnson and R. H. Dettre, "Contact Angle Hysteresis. III. Study of an Idealized Heterogeneous Surface," *J. Phys. Chem.*, vol. 68, no. 7, pp. 1744-1750, 1964. If hydrophobicity is only governed by the Wenzel state, water droplets may settle on the surface even when the surface is tilted until vertical. If hydrophobicity is only governed by the Cassie-Baxter state, water droplets may starts sliding when the surface is tilted a little bit. See Z. Yoshimitsu, A. Nakajima, T. Watanabe, and K. Hashimoto, "Effects of surface structure on the hydrophobicity and sliding behavior of water droplets," *Langmuir*, vol. 18, no. 15, pp. 5818-5822, 2002. Dynamic wettability strongly related to contact angle hysteresis and not the static contact angle. For a water-repellant surface, its dynamic wettability is a very important factor. See D. Öner and T. J. McCarthy, "Ultrahydrophobic surfaces. Effects of topography length scales on wettability," *Langmuir*, vol. 16, no. 20, pp. 7777-7782, 2000.

Water contact angle on a surface is determined by the chemistry of the surface and the surface roughness. A number of techniques have been investigated to fabricate superhydrophobic surface by combining alteration of the surface chemistry with tuning the surface roughness. Rao et al. reported that the change in the contact angle was dominated by the surface chemistry modification rather than the surface roughness alteration. Development of controlled hierarchical rough surface has been achieved by mimicking the surface roughness of the insect's wing or self-cleaning lotus leaves. The surface structure of the developed rough surface enabled entrapment of air between water droplets and the surface as in the Cassie-Baxter state. As shown in the FIG. 2, in the case of Cassie-Baxter state, actual contact area between the solid surface and water droplet is much less than the Wenzel state. This contributes to a less wetting and an adherence between the surface and water droplets, thus creating a highly water repellent surface when combined with low surface energy.

Hydrophobicity is also increased by increasing surface roughness. Researchers have developed fractal surface with enhanced hydrophobicity incorporating different surface structures. See R. D. Hazlett, "Fractal applications: Wettability and contact angle," *J. Colloid Interface Sci.*, vol. 137, no. 2, pp. 527-533, 1990; S. Shibuichi, T. Onda, N. Satoh, and K. Tsujii, "Super Water-Repellent Surfaces Resulting from Fractal Structure," *J. Phys. Chem.*, vol. 100, no. 50, pp. 19512-19517, January 1996; A. Nakajima, A. Fujishima, K.

Hashimoto, and T. Watanabe, "Preparation of Transparent Superhydrophobic Boehmite and Silica Films by Sublimation of Aluminum Acetylacetonate," *Adv. Mater.*, vol. 11, no. 16, pp. 1365-1368, November 1999; and Hideo Nakae, Ryuichi Inui, Yosuke Hirata, and Hiroyuki Saito, "Effects of surface roughness on wettability," *Acta Mater.*, vol. 46, no. 7, pp. 2313-2318, 1998. It is however difficult to correlate the surface roughness and hydrophobicity. Didem Oner et al. prepared surfaces containing square spots of different sizes. They found that spots with X-Y dimensions of 32 μm and below exhibited superhydrophobic behavior with high advancing and receding contact angles. Yoshimitsu et al. developed a series of pillar and groove structures and concluded that groove surface structure on the silicon wafer having lower water contact angle than pillar surface structure. This is mainly because of better water shedding nature of groove surface structure than the pillar surface structure. Budunoglu et al. created micro and nanoscale roughness and resulted surface having contact angles up to 179° and sliding angles less than 5° associated with the thermal stability up to 500° C. See H. Budunoglu, "Highly transparent, flexible, and thermal stable superhydrophobic ORMOSIL aerogel thin films," *Appl. Mater. Interfaces*, pp. 539-545, 2010. Gao et al. developed superhydrophobic surfaces with hierarchical structure using PDMS and silica particles deposited onto glass slide. See N. Gao, Y. Y. Yan, X. Y. Chen, and D. J. Mee, "Superhydrophobic surfaces with hierarchical structure," *Mater. Lett.*, vol. 65, no. 19-20, pp. 2902-2905, 2011. The silica-PDMS film was deposited by using simple immersion method for 10 minutes. Two sizes of silica particles were used; 7 nm and 14 nm. They found that 14 nm particles sizes have higher contact angle than 7 nm particles size due to the regularity of its micro- and nano-structure. Silica particle-PDMS surface with 7 nm has more grooves and irregularities which minimize the amount of air pockets to maintain the water droplet. Even, the hysteresis contact angle has shown similar trend with 100 for 14-nm particles and 400 for 7-nm particles; the combination of the 14-nm and the 7-nm particles resulted in a hysteresis angle of 30°. Jin et al. developed hierarchical-structured superhydrophobic surfaces using PDMS by casting and laser etching. See M. Jin, X. Feng, J. Xi, J. Zhai, K. Cho, L. Feng, and L. Jiang, "Super-Hydrophobic PDMS Surface with Ultra-Low Adhesive Force a," pp. 1805-1809, 2005. The resulted surface texture is micro-submicron-nanostructures which is generated by micropillars and submicron-nano grooves with static and dynamic water contact angles 162° and <5°, respectively.

As mentioned above, Rao et al. concluded that the higher contact angles are dominated by the surface chemical modification rather than the roughness of the surface. The contact angle of a liquid droplet on a smooth solid surface was described by Thomas Young as in the below equation. See T. Young, "An Essay on the Cohesion of Fluids," *Philos. Trans. R. Soc. London*, vol. 95, no. 0, pp. 65-87, 1805.

$$\gamma_{lv}\cos\alpha_Y = \gamma_{sv} - \gamma_{sl} \text{ or } \cos\alpha_Y = \frac{\gamma_{sv} - \gamma_{sl}}{\gamma_{lv}}$$

Where, $\gamma_{lv}$ represents the liquid-vapor tension, $\gamma_{sv}$ represents the solid-vapor tension and $\gamma_{sl}$ represents the solid-liquid interfacial tensions, and a is the static contact angle. Table 1 provides the critical surface tension ($\gamma_c$) values of surface functional groups in relation to surface constitution at 20°. According to Table 1, it is clear that the surface functionalized by fluorocarbon group of $CF_3$ having lowest surface energy. Substitution of fluorine atoms by hydrogen atoms in $CF_3$ groups can increase the surface energy. Normally, to get low surface energy surface, functionalization of the surface by fluorocarbon groups is preferred as compared to hydrocarbon groups and chlorocarbon groups.

TABLE 1

Critical surface tension ($\gamma_c$) values in relation to surface constitution at 20°.

| Surface groups | $\gamma_c$ (mN/m) |
|---|---|
| Fluorocarbon surfaces | |
| —$CF_3$ | 6 |
| —$CF_2H$ | 15 |
| —$CF_2$—$CF_2$— | 18 |
| —$CF_2$—CFH | 22 |
| —$CF_2$—$CH_2$— | 25 |
| —CFH—$CH_2$— | 28 |
| Hydrocarbon surfaces | |
| —$CH_3$ (crystal) | 20-22 |
| —$CH_3$ (monolayer) | 22-24 |
| —$CH_2$—$CH_2$— | 31 |
| —CH— (phenyl ring edge) | 35 |
| Chlorocarbon surfaces | |
| —CClH—$CH_2$— | 39 |
| —$CCl_2$—$CH_2$— | 40 |
| —$CCl_2$ | 43 |

One way to create and adjust the surface roughness of a material is through using surface modified silica ($SiO_2$) particles. Modification of the silica particles by low surface energy reagents can lead to a low surface energy layer. Silica is in the form of colloid dispersion of silica nanoparticles in an aqueous phase, i.e. silica sols. Silica sols can be used in solution-gelation (or sol-gel) reactions, where reaction usually go through the hydrolysis and condensation process used to create oxide network structures with the surface functionalized by low surface energy functional groups. It is known that unmodified silica aerogel surface contains hydrolysable silanol (Si—OH) groups, which can be hydrolyzed through hydrolysis reactions. These hydroxyl (—OH) groups present on the surface of silica particles are considered as the main source of hydrophilicity. See T. Jesionowski, J. Zurawska, and A. Krysztafkiewicz, "Surface properties and dispersion behavior of precipitated silica," *J. Mater. Sci.*, vol. 37, no. 8, pp. 1621-1633, 2002. In order to make the surface of silica particles hydrophobic, silanol (Si—OH) groups should be replaced by more hydrolytically stable silicon alkyl groups (i.e. Si—$CH_3$). See G. H. Findenegg and S. Herminghaus, "Wetting: Statics and dynamics," *Curr. Opin. Colloid Interface Sci.*, vol. 2, no. 3, pp. 301-307, 1997. FIG. 3 is a schematic diagram showing replacement of hydrophilic groups of a silica by hydrophobic groups. See P. Buisson, C. Hernandez, M. Pierre, and A. Pierre, "Encapsulation of lipases in aerogels," *J. Non. Cryst. Solids*, vol. 285, no. 1-3, pp. 295-302, June 2001; A. Venkateswara Rao and D. Haranath, "Effect of methyltrimethoxysilane as a synthesis component on the hydrophobicity and some physical properties of silica aerogels," *Microporous Mesoporous Mater.*, vol. 30, no. 2-3, pp. 267-273, 1999. FIG. 4 shows the organically modified silanes with different functionalities. A tetra-functional silicon alkoxide (n=0) can act as a "network forming" structure since it has four hydrolyzable sites. A trifunctional silicon alkoxide (n=1) may behave as a "cross-linker" with its three hydrolyzable sites. A difunctional silicon alkoxide (n=2) having two hydrolyzable sites may act as a "bridging" agent, and a monofunctional silicon alkoxide (n=4) can be used as a "terminating" agent, since it has only one site that can take part in a reaction. See R. Ciriminna, A. Fidalgo, V. Pandarus, L. M. Ilharco, M. Pagliaro, and A. R. Pais, "The Sol-Gel Route to Advanced Silica-Based Materials and Recent Applications," 2012.

Some researchers reported that using commercially available abrasion resistance silicone resin improves the abrasion resistance of the superhydrophobic surfaces. See M. S. Lee and N. J. Jo, "Coating of Methyltriethoxysilane-Modified Colloidal Silica on Polymer Substrates for Abrasion Resistance," J. Sol-Gel Sci. Technol., vol. 24, no. 2, pp. 175-180, 2002; and L. Y. L. Wu, E. Chwa, Z. Chen, and X. T. Zeng, "A study towards improving mechanical properties of sol-gel coatings for polycarbonate," Thin Solid Films, vol. 516, no. 6, pp. 1056-1062, 2008. The enhancement of abrasion resistance can be obtained by using a coupling/bonding agent to increase the adhesion between the substrate and the thin hydrophobic layers. A superhydrophobic material with an enhanced abrasion resistance can be safely used in harsh environments without the concern of getting severe damages to the superhydrophobic material over time.

In view of the forgoing, one objective of the present disclosure is to provide a substrate with a superhydrophobic coating, wherein the superhydrophobic coating includes a binding layer disposed on the substrate, and a hydrophobic layer disposed on the binding layer, wherein the hydrophobic layer includes perfluoroalkyl-functionalized silica nanoparticles. The present disclosure further provides a method of fabricating the substrate with the superhydrophobic coating.

BRIEF SUMMARY OF THE INVENTION

According to a first aspect, the present disclosure relates to a method of forming a superhydrophobic coating, involving i) mixing a solution comprising an alkyl alkoxysilane, a glycidyl-containing alkoxysilane, an alcohol, ammonium hydroxide, and water to form a mixture and applying the mixture onto a substrate, ii) heating the substrate and the mixture applied thereon, wherein the substrate is functionalized with the alkyl alkoxysilane and the glycidyl-containing alkoxysilane, thereby forming a coated substrate comprising a binding layer on the substrate, iii) applying a suspension comprising perfluoroalkyl-functionalized silica nanoparticles onto the coated substrate to form a hydrophobic layer on the binding layer, thereby forming the superhydrophobic coating.

In one embodiment, the method further involves annealing the substrate with the superhydrophobic coating at a temperature in the range of 100° C. to 300° C. for no more than 2 hours.

In one embodiment, the mixture is applied onto the substrate by spray-coating, and the suspension is applied onto the coated substrate by spray-coating.

In one embodiment, the substrate and the mixture applied thereon are heated at a temperature of 30 to 90° C. for no more than 3 hours.

In one embodiment, the alkyl alkoxysilane is selected from the group consisting of methyltrimethoxysilane, methyltriethoxysilane, ethyltrimethoxysilane, trimethylethoxysilane, and dimethyldiethoxysilane.

In one embodiment, the glycidyl-containing alkoxysilane is (3-glycidyloxypropyl)trimethoxysilane.

In one embodiment, a weight percent of the perfluoroalkyl-functionalized silica nanoparticles in the suspension is in the range of 0.1 wt % to 2.0 wt %, relative to the total weight of the suspension.

In one embodiment, a molar ratio of the glycidyl-containing alkoxysilane to the alkyl alkoxysilane in the solution is from 1:1 to 1:5, and a molar ratio of the alkyl alkoxysilane to the water in the solution is from 1:3 to 1:6.

In one embodiment, the perfluoroalkyl-functionalized silica nanoparticles in the suspension are formed by sonicating silica nanoparticles in the presence of a perfluoroalkylsilane.

In one embodiment, the perfluoroalkylsilane is 1,1,2,2-perfluorooctyltriethoxysilane.

In one embodiment, an average diameter of the silica nanoparticles is in the range of 1 to 100 nm.

According to a second aspect, the present disclosure relates to a substrate with a superhydrophobic coating, wherein the superhydrophobic coating includes a binding layer disposed on the substrate, ii) a hydrophobic layer disposed on the binding layer, wherein the hydrophobic layer comprises perfluoroalkyl-functionalized silica nanoparticles, and wherein the perfluoroalkyl-functionalized silica nanoparticles are not in contact with the substrate.

In one embodiment, the binding layer has a thickness of no more than 100 μm.

In one embodiment, the substrate is selected from the group consisting of glass, quartz, paper, aluminum, steel, fabric, card board, and acrylic.

In one embodiment, the superhydrophobic coating has an average contact angle in the range of 110° to 175°.

In one embodiment, the superhydrophobic coating has an average light transmittance in the range of 60% to 90% for a light with a wavelength of 400 to 800 nm.

In one embodiment, the superhydrophobic coating has an average surface roughness in the range of 0.3 to 1.0 μm.

In one embodiment, the superhydrophobic coating has an average surface energy in the range of 3 to 12 $mJ/m^2$.

In one embodiment, the superhydrophobic coating maintains an average contact angle of 110° to 175° after being exposed to UV light for at least 12 hours.

In one embodiment, the superhydrophobic coating maintains an average light transmittance of 60% to 90% after being exposed to UV light for at least 12 hours.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 5 illustrates a chemical structure of (a) methyltrimethoxysilane, (b) (3-glycidyloxypropyl)trimethoxysilane, and (c) 1,1,2,2-perfluorooctyltriethoxysilane.

FIG. 15A represents transmittance spectra of the coated substrate, i.e. a transparent substrate that includes one or more binding layers thereon, 24 hours after preparation, wherein the substrate is spray-coated at a spray distance of 10 cm.

FIG. 15B represents transmittance spectra of the coated substrate, i.e. a transparent substrate that includes one or more binding layers thereon, 24 hours after preparation, wherein the substrate is spray-coated at a spray distance of 15 cm.

FIG. 18A represents a state of a water droplet on a bare glass substrate.

FIG. 18B represents a state of a water droplet on a superhydrophobic coating with one hydrophobic layer.

FIG. 18C represents a state of a water droplet on a superhydrophobic coating with two hydrophobic layers.

FIG. 18D represents a state of a water droplet on a superhydrophobic coating with three hydrophobic layers.

FIG. 18E represents a state of a water droplet on a superhydrophobic coating with four hydrophobic layers.

FIG. 18F represents a state of a water droplet on a superhydrophobic coating with five hydrophobic layers.

FIG. 25A is a 2D AFM micrograph of a surface of the superhydrophobic coating with three hydrophobic layers.

FIG. 25B is a line scan of the 2D AFM micrograph of a surface of the superhydrophobic coating with three hydrophobic layers.

FIG. 25C is a 3D AFM micrograph of a surface of the superhydrophobic coating with three hydrophobic layers.

FIG. 30A represents an XPS spectrum of the superhydrophobic coating with three hydrophobic layers over a binding energy range of 0 to 1,100 eV.

FIG. 30B represents an XPS spectrum of the superhydrophobic coating with three hydrophobic layers over a binding energy range of 280 to 300 eV.

FIG. 42A represents time-lapsed photos that capture the bouncing of a water droplet on a surface, wherein the surface is an uncoated paper.

FIG. 42B represents time-lapsed photos that capture the bouncing of a water droplet on a surface, wherein the surface is a coated paper.

FIG. 42C represents time-lapsed photos that capture the bouncing of a water droplet on a surface, wherein the surface is an uncoated cloth.

FIG. 42D represents time-lapsed photos that capture the bouncing of a water droplet on a surface, wherein the surface is a coated paper.

FIG. 42E represents time-lapsed photos that capture the bouncing of a water droplet on a surface, wherein the surface is an uncoated aluminum.

FIG. 42F represents time-lapsed photos that capture the bouncing of a water droplet on a surface, wherein the surface is a coated aluminum.

FIG. 42G represents time-lapsed photos that capture the bouncing of a water droplet on a surface, wherein the surface is an uncoated glass.

FIG. 42H represents time-lapsed photos that capture the bouncing of a water droplet on a surface, wherein the surface is a coated glass.

FIG. 42I represents time-lapsed photos that capture the bouncing of a water droplet on a surface, wherein the surface is an uncoated acrylic.

FIG. 42J represents time-lapsed photos that capture the bouncing of a water droplet on a surface, wherein the surface is a coated acrylic.

FIG. 42K represents time-lapsed photos that capture the bouncing of a water droplet on a surface, wherein the surface is an uncoated steel mesh.

FIG. 42L represents time-lapsed photos that capture the bouncing of a water droplet on a surface, wherein the surface is a coated steel mesh.

DETAILED DESCRIPTION OF THE EMBODIMENTS

Figure 1A:
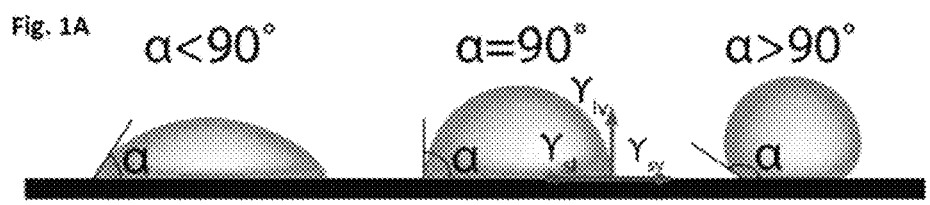
FIG. 1A illustrates a state of a water droplet on a surface under a static condition.

Referring now to the drawings, wherein like reference numerals designate identical or corresponding parts throughout the several views.

Figure 9:
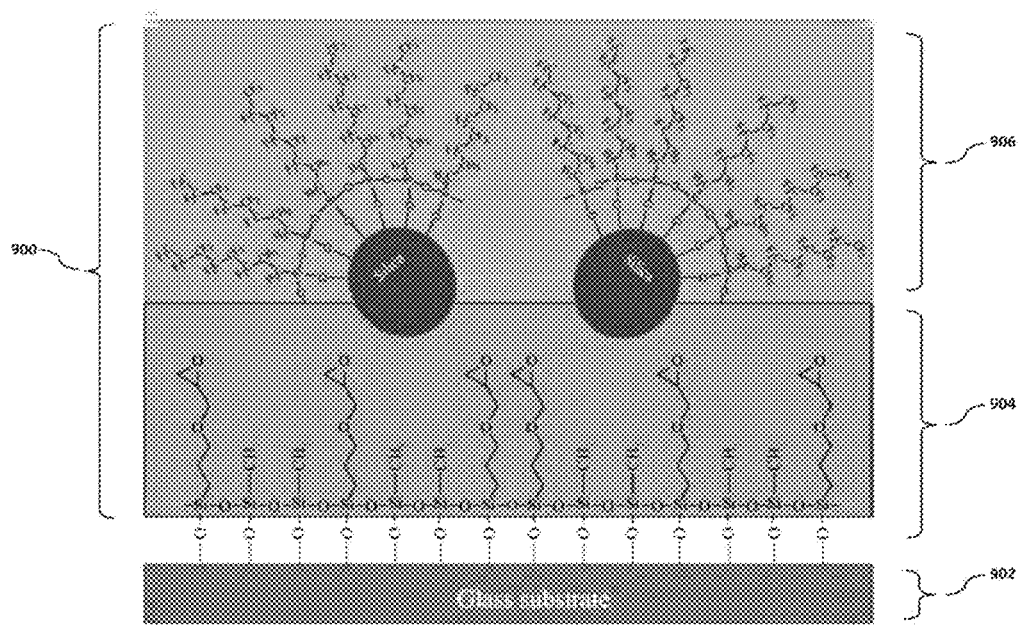
FIG. 9 illustrates a substrate with a superhydrophobic coating, wherein the superhydrophobic coating includes a binding layer disposed on the substrate, and a hydrophobic layer disposed on the binding layer.

Referring to FIG. 9, according to a first aspect, the present disclosure relates to a substrate 902 with a superhydrophobic coating 900, wherein the superhydrophobic coating includes a binding layer 904 disposed on the substrate 902, and a hydrophobic layer 906 disposed on the binding layer 904.

Hydrophobicity is a measure of wetting properties of a material's surface and relates to the difficulty or ease by which the material's surface is wet. In a number of technology fields and industrial applications, materials with one or more hydrophobic surfaces or one or more superhydrophobic surfaces are advantageous due to their self-cleaning properties and relative difficulty to wet. In antibacterial settings hydrophobicity of a surface may reduce biofouling of the surface. One measure for a surface hydrophobicity is a measurement of a contact angle of a water droplet. Accordingly, a "hydrophobic" surface is a surface, wherein a contact angle of a water droplet ranges from about 90° to about 130°, preferably from about 100° to about 120°; whereas a "superhydrophobic" surface is a surface, wherein a contact angle of a water droplet is greater than 110°, preferably greater than 130°, preferably in the range from about 150° to about 180°, preferably from about 160° to about 175°. In view of that, the term "superhydrophobic coating" as used in this disclosure refers to a layer that is coated on a material and provides a water contact angle of from about 110° to about 175°, preferably from about 120° to about 174°, preferably from about 130° to about 173° to the material.

Figure 1B:
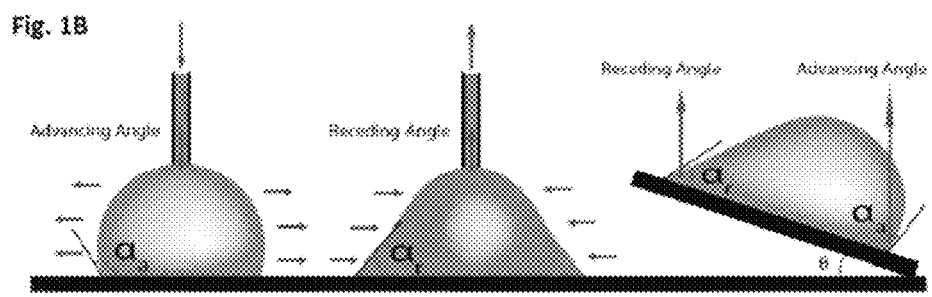
FIG. 1B illustrates a state of a water droplet on a surface under a dynamic condition.
Figure 2:
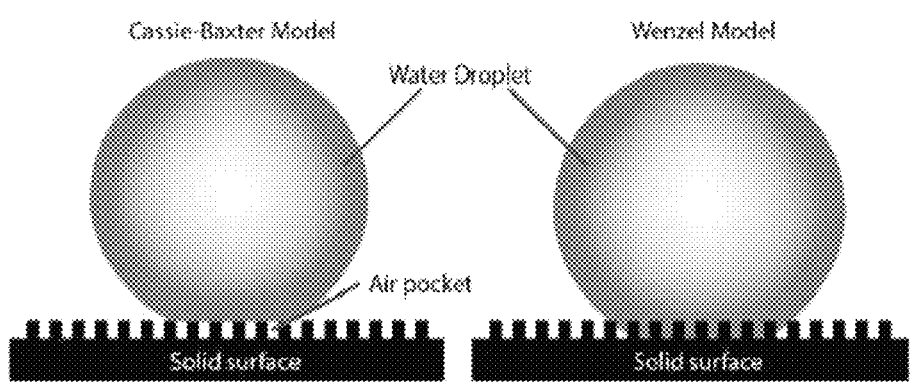
FIG. 2 illustrates the Cassie-Baxter state and the Wenzel state of a water droplet.
Figure 3:
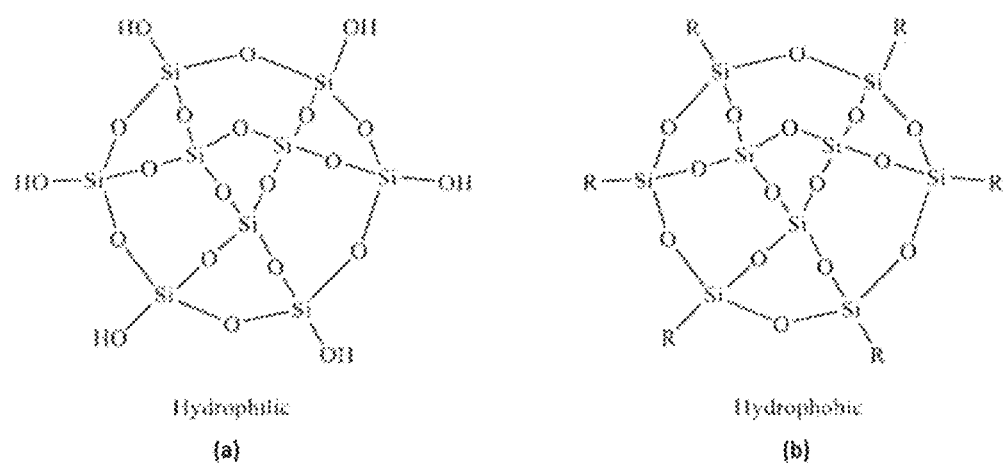
FIG. 3 illustrates a chemical structure of (a) a hydrophilic silica aerogel, (b) a hydrophobic silica aerogel.
Figure 4:
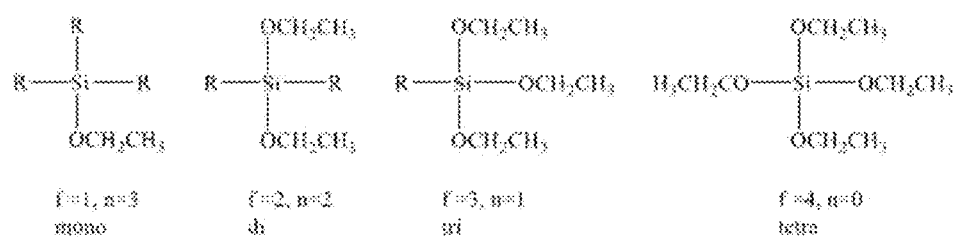
FIG. 4 illustrates a mono-, a di-, a tri-, and a tetra-functional silica.

As used herein, the term "contact angle" refers to the angle between a static drop of water, preferably deionized water, and a flat and horizontal surface upon which the drop of water is placed. Said angle is an intersection of a liquid-solid interface and a liquid-vapor interface as represented by a in FIG. 1(a). As the contact angle of a surface increases, a wetting resistance of the surface increases accordingly, wherein a liquid droplet, e.g. a water droplet, becomes substantially spherical on the surface. In one embodiment, the contact angle of the superhydrophobic coating 900 may be determined using a contact angle goniometer. Alternatively, the contact angle of the superhydrophobic coating may be determined using the methods known to those skilled in the art. In circumstances where water droplets move, a dynamic contact angle may be measured to characterize hydrophobicity of a moving surface. A moving surface may be due to expansion or contraction of the water droplets or due to a motion of the water droplet. A moving water droplet may form an advancing contact angle ($\alpha_a$) and a receding contact angle ($\alpha_r$) as represented in FIG. 1(b). The difference between the advancing angle and the receding angle is called the hysteresis (H). See G. Bracco and B. Hoist, *Surface science techniques*, vol. 51, no. 1. 2013. The contact angle of a water droplet on the superhydrophobic coating 900 may be in the range from about 110° to about 175°, preferably from about 120° to about 174°, preferably from about 130° to about 173°. The advancing contact angle of a water droplet on the superhydrophobic coating 900 may be in the range from about 130° to about 175°, preferably from about 140° to about 170°, preferably from about 145° to about 168°. The receding contact angle of a water droplet on the superhydrophobic coating 900 may be in the range from about 100° to about 170°, preferably from about 110° to about 165°, preferably from about 115° to about 162°. The hysteresis of a water droplet on the superhydrophobic coating 900 may be in the range from about 0° to about 20°, preferably from about 1° to about 15°, preferably from about 2° to about 10°.

The term "substrate" as used in this disclosure relates to any material, particle and/or object, wherein the hydrophobic layer 906 is disposed thereon. The substrate 902 may be made of a metal, a ceramic, a polymer, etc. In some embodiments, the substrate 902 is selected from the group consisting of glass, quartz, paper, aluminum, steel, fabric, card board, and acrylic. In a preferred embodiment, the substrate 902 is glass or quartz. In another preferred embodiment, the substrate 902 is a transparent polymer. Exemplary transparent polymers may include, without limitation, polyethylene terephthalate, polybutylene terephthalate, polyethylene terephthalate glycol-modified, polyethylene-2,6-naphthalate, triacetyl cellulose, liquid crystal polymers such as thermotropic liquid crystal polyester and thermotropic liquid crystal polyester amide, acrylic resins such as polyacrylate and polymethacrylate, olefin resins such as polyethylene and polypropylene, vinyl resins such as polyvinyl chloride, an ethylene-vinyl acetate copolymer, and an ethylene-vinyl alcohol copolymer, imide resins such as polyimide and polyamide-imide, and ether resins such as polyethernitrile, polyether sulfone, polystyrene, polycarbonate, poly methyl methacrylate, styrene acrylonitrile, styrene methyl methacrylate, methyl metacrylate butadiene styrene, and any combinations thereof. In a preferred embodiment, the substrate 902 is polymethylmethacrylate or polycarbonate. The substrate 902 may be a fibrous material, a non-woven fabric, a cotton fabric, a non-woven synthetic polymer fabric, e.g. polyester fabric, or combinations thereof. In some embodiments, the substrate 902 may be a printed circuit board, LCD screens, LED screens, surgical gowns, medical packaging, filters, piping, plumbing, sanitary surfaces, photovoltaic cells located in dry climates, hospital equipment and surfaces such as flooring and wall tiles, patient bed frames, tables, doors, or medical tubing. The substrate may be flexible or rigid depending on the application. In one embodiment, the substrate 902 has a slab geometry, wherein a thickness of the substrate may be in the range of 1 to 100 mm, preferably 2 to 50 mm, preferably 3 to 40 mm. The substrate may have a cylindrical geometry, e.g. a pipe, or a spherical geometry, e.g. a spherical container or a spherical vessel, or a curved geometry, e.g. a curved mirror.

In some embodiments, the substrate 902 is transparent, wherein an average light transmittance that passes through the substrate is in the range of 90% to 100%, preferably 95% to 99%, preferably 97% to 98%, for a light with a wavelength in the range of 400 to 800 nm. As used herein, a "transmittance" of a material refers to an effectiveness of transmitting radiant energy through the material, i.e. a percentage of the radiant energy that is transmitted through the material and is not lost due to absorption, scattering, reflection, etc. The term "light transmittance" refers to the amount of light photons in the UV-visible portion of a light spectrum that passes through the material, preferably light photons having a wavelength of 400 to 800 nm, preferably 410 to 790 nm, preferably 420 to 780 nm.

The term "binding layer" as used in this disclosure refers to an adhesive that is applied onto the substrate 902 to adhere the substrate 902 to the hydrophobic layer 906. The binding layer 904 may preferably have a thickness of no more than 100 µm, preferably no more than 50 µm. In some embodiments, the binding layer 904 may have a uniform thickness in the range of 300 to 700 µm, preferably 400 to 600 µm. As used herein, "a layer with a uniform thickness" refers to a layer, wherein a difference in the thickness of the layer at a first point and at a second point is preferably no more than 5%, preferably no more than 2%, preferably no more than 1% of the thickness of the layer at the first point or at the second point.

In some embodiments, an average light transmittance of the binding layer is in the range of 90% to 100%, preferably 95% to 99%, preferably 96% to 99%, for a light with a wavelength in the range of 400 to 800 nm.

The term "hydrophobic layer" as used in this disclosure refers to a layer that is applied onto the binding layer 904 and immobilized onto the substrate 902 by the binding layer 904. The hydrophobic layer 906 comprises perfluoroalkyl-functionalized silica nanoparticles 704. Due to the presence of the perfluoroalkyl-functionalized silica nanoparticles 704, the hydrophobic layer 906 provides self-cleaning and superhydrophobic properties to the superhydrophobic coating.

As shown in FIG. 9, the perfluoroalkyl-functionalized silica nanoparticles 704 are not in contact with the substrate 902. Preferably, the perfluoroalkyl-functionalized silica nanoparticles 704 are not present in the binding layer 904, and are only in contact with the binding layer 904. The perfluoroalkyl-functionalized silica nanoparticles 704 may be in contact with the binding layer 904 at a junction surface of the binding layer 904 and the hydrophobic layer 906, as shown in FIG. 9. In addition, the binding layer 904 preferably does not include any compounds that reduce a surface energy of the superhydrophobic coating, or any compounds that enhance the contact angle or the surface roughness of the superhydrophobic coating. The perfluoroalkyl-functionalized silica nanoparticles 704 are not englobed or matrixed within the binding layer 904. The perfluoroalkyl-functionalized silica nanoparticles 704 are preferably not in contact with the surface of the substrate.

In view of that, the binding layer 904 may preferably not influence the self-cleaning and/or superhydrophobic properties of the superhydrophobic coating. Preferably, the hydrophobic layer 906 has a uniform thickness, i.e. substantially the same thickness over an entire surface of the substrate 902, in the range of 10 nm to 500 µm, preferably 20 nm to 400 µm, preferably 50 nm to 300 µm.

In some embodiments, an average light transmittance of the hydrophobic layer 906 is in the range of 60% to 90%, preferably 65% to 88%, preferably 70% to 85%, for a light with a wavelength in the range of 400 to 800 nm.

In some embodiments, the superhydrophobic coating 900 is applied onto a transparent substrate, wherein an average light transmittance of the substrate with the superhydrophobic coating is in the range of 60% to 90%, preferably 70% to 88%, preferably 75% to 85%, for a light with a wavelength range of 400 to 800 nm. In a preferred embodiment, the superhydrophobic coating 900 is applied onto a transparent substrate, wherein the average light transmittance of the substrate with the superhydrophobic coating is reduced by no more than 25%, preferably no more than 20%, preferably no more than 15%, preferably no more than 10%, preferably no more than 5%, relative to the average light transmittance of the substrate 902.

In one embodiment, the superhydrophobic coating 900 has an average surface roughness in the range of 0.3 to 1.0 µm, preferably 0.35 to 0.8 µm, preferably 0.4 to 0.6 µm, preferably 0.42 to 0.5 µm. As used herein, the term "surface roughness" is a characteristic of a material's surface, which is quantified by deviations of a normal vector, which moves along the material's surface, from an ideal form of the material's surface. If the deviations are large, the surface is rough, and if the deviations are small, the surface is smooth. In one embodiment, the surface roughness of a material may be measured by manual comparison against a sample with a known surface roughness. Alternatively, the surface roughness of a material may be measured with a profilometer that may be obtained by a contact measurement and/or an optical measurement. In one embodiment, the surface roughness of the superhydrophobic coating 900 may be determined using atomic force microscopy (AFM).

In one embodiment, the superhydrophobic coating 900 has an average surface energy in the range of 5 to 8 mJ/m$^2$, preferably about 6 mJ/m$^2$. The term "surface energy" as used herein quantifies the disruption of intermolecular bonds that occur when a surface is created. The surface energy of the superhydrophobic coating 900 may be determined by methods known to those skilled in the art, e.g. Dyne Test Inks®, etc.

Figure 34:
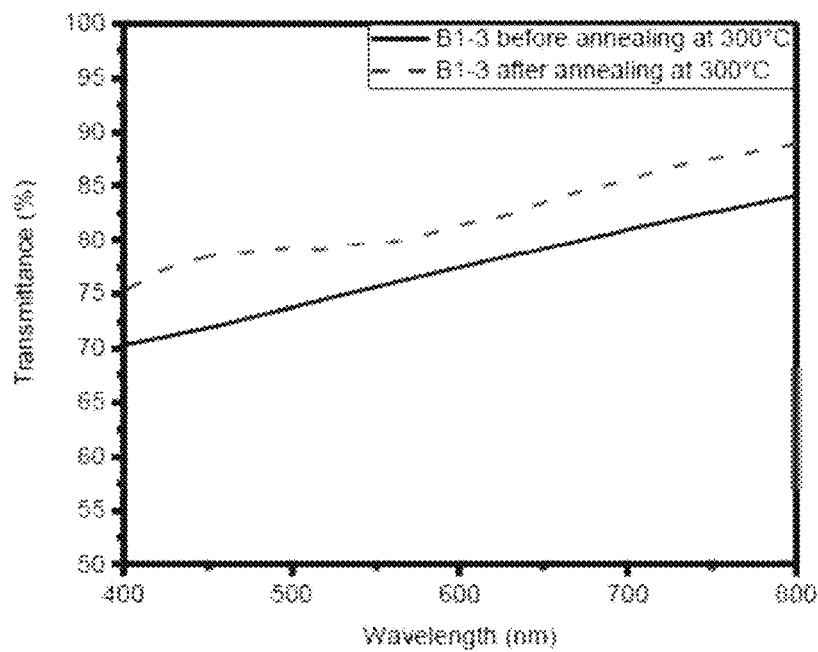
FIG. 34 represents transmittance spectra of the superhydrophobic coating before and after annealing at 300° C.

The substrate with the superhydrophobic coating may be utilized in harsh environments and climates, e.g. humid and rainy climates such as rain forests, dry sunny and dusty climates such as deserts, etc. Preferably, the average contact angle, the average light transmittance, and/or the surface roughness of the superhydrophobic coating 900 may not be reduced when utilized in the harsh environments. In some embodiments, using the superhydrophobic coating 900 in the harsh environments may reduce the average contact angle, the average light transmittance, and/or the surface roughness by no more than 2%, preferably no more than 1%, preferably no more than 0.5%, relative to an initial value of each of the variables. For example, in some embodiments, the superhydrophobic coating may be utilized at a temperature of no more than 350° C., preferably no more than 300° C., preferably in the range of 100° C. to 300° C., wherein the average contact angle, the average light transmittance, and/or the surface roughness are reduced by no more than 2%, preferably no more than 1%, preferably no more than 0.5%. In some embodiments, the average light transmittance of the superhydrophobic coating 900 over a visible light wavelength range (i.e. a light with a wavelength of 400 to 800 nm) may be increased by 2% to about 10%, preferably about 5% after annealing the substrate with the superhydrophobic coating at a temperature of 200° C. to 350° C., preferably 250° C. to 320° C., preferably about 300° C., as shown in FIG. 34. In some alternative embodiment, the superhydrophobic coating 900 is exposed to a UV light for at least 12 hours, preferably at least 24 hours, preferably at least 100 hours, preferably at least 200 hours, wherein the average contact angle, the average light transmittance, and/or the surface roughness is reduced by no more than 2%, preferably no more than 1%, preferably no more than 0.5%.

Figure 32:
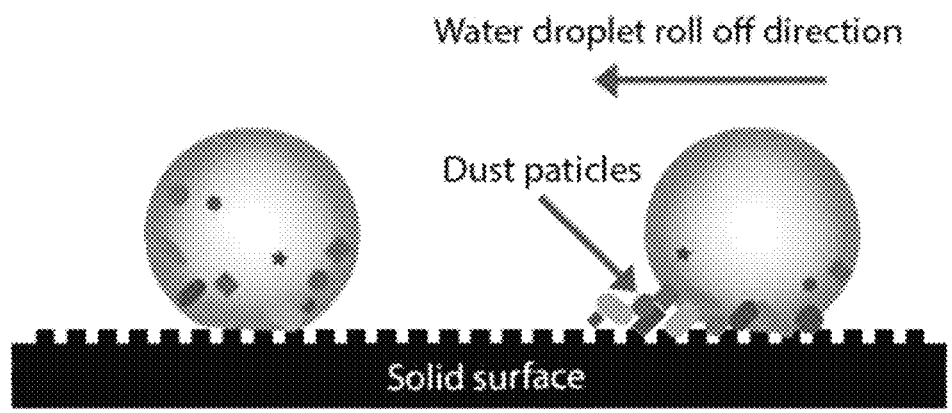
FIG. 32 illustrates a self-cleaning mechanism of the superhydrophobic coating.
Figure 33A:
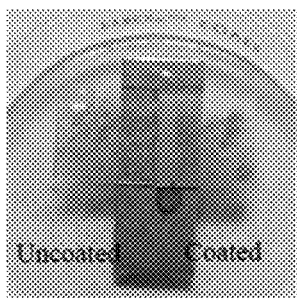
FIG. 33A represents a comparison of a self-cleaning property of a glass substrate (uncoated) and the superhydrophobic coating (coated) after dropping one water droplet.
Figure 33B:
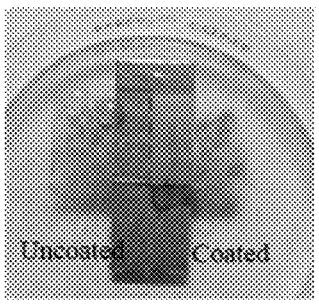
FIG. 33B represents a comparison of a self-cleaning property of a glass substrate (uncoated) and the superhydrophobic coating (coated) after dropping two water droplets.
Figure 33C:
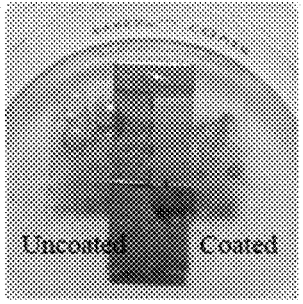
FIG. 33C represents a comparison of a self-cleaning property of a glass substrate (uncoated) and the superhydrophobic coating (coated) after dropping three water droplets.
Figure 33D:
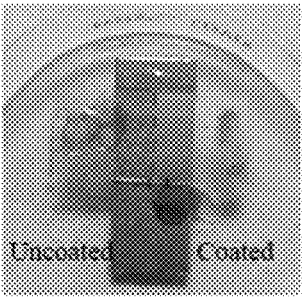
FIG. 33D represents a comparison of a self-cleaning property of a glass substrate (uncoated) and the superhydrophobic coating (coated) after dropping four water droplets.
Figure 33E:
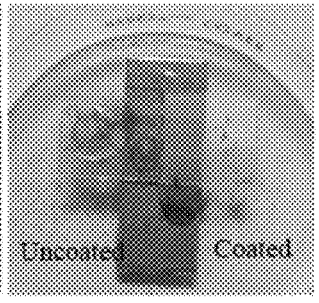
FIG. 33E represents a comparison of a self-cleaning property of a glass substrate (uncoated) and the superhydrophobic coating (coated) after dropping five water droplets.
Figure 33F:
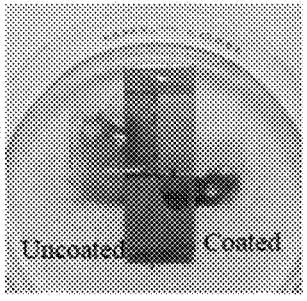
FIG. 33F represents a comparison of a self-cleaning property of a glass substrate (uncoated) and the superhydrophobic coating (coated) after dropping six water droplets.

The superhydrophobic coating 900 may have a self-cleaning property (as shown in FIGS. 32 and 33), due to a low surface energy (i.e. 3 to 12 mJ/m$^2$), a large contact angle (i.e. 110° to 175°), and a microscale roughness (i.e. 0.3 to 1.0 µm). The term "self-cleaning property" as used herein refers to a property of a surface wherein water droplets pick up dirt particles from the surface of the superhydrophobic coating, due to a substantially reduced water adhesion of the surface.

Figure 12:
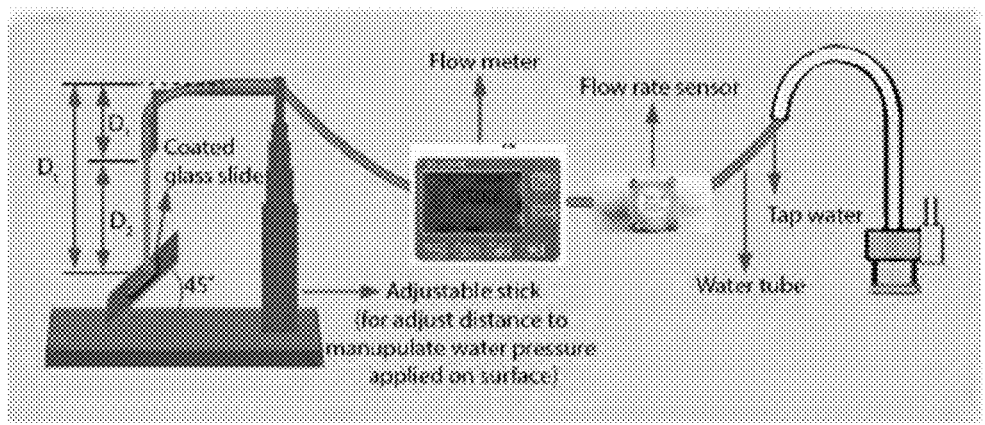
FIG. 12 illustrates a water jet test setup.
Figure 13:
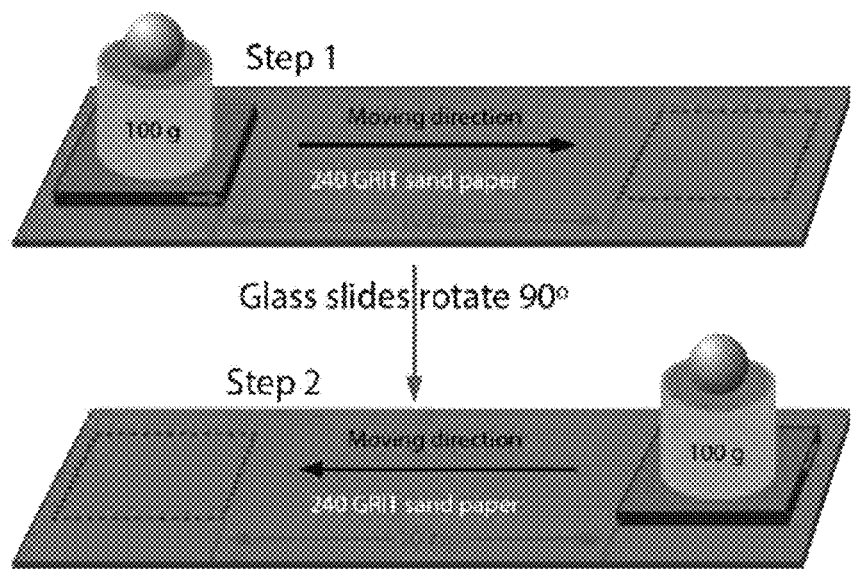
FIG. 13 illustrates an abrasion resistance test setup.
Figure 14A:
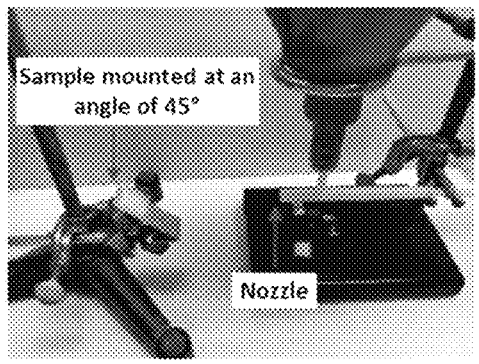
FIG. 14A illustrates a sand blast test setup before a sand blast test.
Figure 14B:
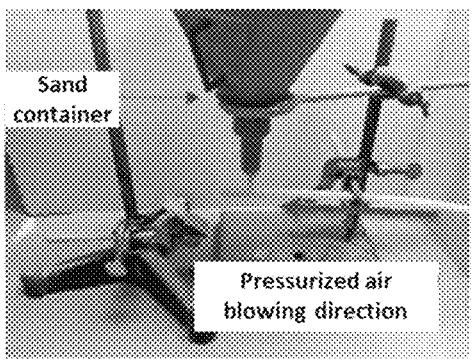
FIG. 14B illustrates a sand blast test setup after a sand blast test.

The hydrophobic layer 906 may preferably be stable and durable in the applications wherein the superhydrophobic coating is exposed to a continuous water contact, e.g. rain or ocean waves, or a continuous solid contact, e.g. dust storms or sandstorms, etc. Stability and durability of the hydrophobic layer 906 may be determined by a water-jet test, an abrasion resistance test, and/or by a sand blast test. Various methodologies may be utilized to characterize the stability and durability of the hydrophobic layer 906, as shown in FIGS. 12, 13, and 14. For example, in one embodiment a water-jet test may be conducted (as illustrated in FIG. 12) to evaluate the stability and durability of the hydrophobic layer 906 when exposed to a continuous water contact. Accordingly, the hydrophobic layer 906 of the superhydrophobic coating 900 may be exposed to a water-jet with a flow rate of 0.1 to 50 L/min, preferably 0.2 to 40 L/min, preferably 0.5 to 10 L/min, for about 30 to 120 minutes, preferably about 45 to 90 minutes, preferably about 60 minutes. The contact angle, the surface roughness, and the surface energy of the superhydrophobic coating are recorded before and after the water-jet test. After the water-jet test, the superhydrophobic coating 900 may preferably maintain at least about 80%, preferably at least about 90%, preferably at least about 95%, relative to the initial values of the contact angle, the surface roughness, and the surface energy of the superhydrophobic coating before the water-jet test.

In another embodiment, an abrasion resistance test may be performed (as illustrated in FIG. 13) to evaluate an abrasive resistance of the hydrophobic layer 906. Accordingly, the hydrophobic layer 906 of the substrate with the superhydrophobic coating is placed on sandpaper with a predetermined grit size, e.g. 240. While different pressures (i.e., from 130 to 1750 Pa) are applied to the superhydrophobic coating, e.g. by placing a weight on the the substrate with the superhydrophobic coating, the material is moved in a back-and-forth fashion with a known constant speed for multiple cycles, as shown in FIG. 13. The contact angle, the surface roughness, and the surface energy of the superhydrophobic coating are recorded before and after the abrasion resistance test. After the abrasion resistance test, the superhydrophobic coating may preferably maintain about 60% to about 95%, preferably about 70% to about 90%, preferably about 80% to about 85% of the contact angle, the surface roughness, and the surface energy, relative to the initial values before the abrasion resistance test.

Yet in another embodiment, a sand blast test may be performed (as shown in FIG. 14) to evaluate the stability and durability of the hydrophobic layer 906 when exposed to a continuous solid contact. Accordingly, the hydrophobic layer 906 of the substrate with the superhydrophobic coating is exposed to a sand blast that is provided with a pressurized air (a pressure in the range of 200 to 400 kPa, preferably about 300 kPa) for about 5 to 60 minutes, preferably about 10 to 30 minutes, preferably about 10 minutes. The contact angle, the surface roughness, and the surface energy of the superhydrophobic coating 900 are recorded before and after the sand blast test. After the sand blast test, the superhydrophobic coating 900 may preferably maintain about 50% to about 90%, preferably about 60% to about 85%, preferably about 65% to about 80%, relative to the initial values of the contact angle, the surface roughness, and the surface energy of the superhydrophobic coating before the sand blast test.

The binding layer 904 and the hydrophobic layer 906 may be applied onto various types of surfaces. These surfaces may include, without limitation, medical devices, plumbing fixtures, condenser coils, optical surfaces, boat hulls, aircrafts, counter tops, windows, appliances, hard floors, rugs, tubs, showers, mirrors, toilets, bidets, bathroom fixtures, sinks, refrigerators, microwaves, small kitchen appliances, tables, chairs, cabinets, drawers, sofas, love seats, benches, beds, stools, armoires, chests, dressers, display cabinets, clocks, buffets, shades, shutters, entertainment centers, arm rails, lamps, banisters, libraries, cabinets, desks, doors, shelves, couches, carts, pianos, statues, racks, fans, light fixtures, pool tables, ping pong tables, soccer tables, card tables, tools (e.g., hand powered and/or hand held tools, electrical tools, air powered tools, etc.), telephones, radios, televisions, stereo equipment, CD and DVD players, analog and digital sound devices, palm computers, laptop computers, desktop and tower computers, computer monitors, mp3 players, memory storage devices, cameras, camcorders, vehicle surfaces (e.g., windshield, tires, metal, fiberglass composite material, plastic outer surfaces, fabric and/or vinyl outer surfaces, fabric, vinyl, and/or leather interior surfaces, metal, plastic, wood and/or composite material interior surfaces, glass interior surfaces, etc.), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. Any surface where it is desirable to cause one or more types of liquids to run off of a surface, to not be absorbed into a surface, and/or to not stain a surface may be a substrate 902 for the binding layer 904 and the hydrophobic layer 906 of this invention disclosure. In a preferred embodiment, the binding layer 904 and the hydrophobic layer 906 may be applied on surfaces that are exposed to environmental conditions, which degrade the surfaces, to protect the surfaces. Also, the binding layer 904 and the hydrophobic layer 906 may be applied on surfaces to reduce microbial adhesion to the surfaces.

In a preferred embodiment, the binding layer 904 and the hydrophobic layer 906 may be applied onto a photovoltaic or solar cell that contains a transparent glass surface or a transparent polymeric surface. Exemplary solar cells or photovoltaic cells that may utilize the binding layer 904 and the hydrophobic layer 906 may include, without limitation, amorphous silicon solar cells, biohybrid solar cells, buried contact solar cells, cadmium telluride solar cells, concentrated PV solar cells, copper indium gallium selenide solar cells, dye-sensitized solar cells, gallium arsenide germanium solar cells, hybrid solar cells, luminescent solar concentrator cells, micromorph cells, monocrystalline solar cells, multijunction solar cells, nanocrystal solar cells, organic solar cells, perovskite solar cells, photoelectrochemical cells, plasmonic solar cells, plastic solar cells, polycrystalline solar cells, polymer solar cells, quantum dot solar cells, solid-state solar cells, thin-film solar cells, and wafer solar cells.

In another preferred embodiment, the binding layer 904 and the hydrophobic layer 906 may be applied onto an inner surface area of water pipes to reduce water/pipe frictions and thereby reduce a subsequent water pressure drops that occur in the water pipes.

According to a second aspect, the present disclosure relates to a method of fabricating the substrate with the superhydrophobic coating.

Accordingly, in a first step a mixture is applied onto the substrate 902, wherein the mixture is prepared by mixing a solution comprising alkyl alkoxysilane, a glycidyl-containing alkoxysilane, an alcohol, ammonium hydroxide, and water. Preferably, the alkyl alkoxysilane, the glycidyl-containing alkoxysilane, the alcohol, ammonium hydroxide, and water may be mixed (with no preference in mixing orders) in a dropwise manner for lab-scale applications, e.g. benchtop pilots, or a non-dropwise manner for large-scale applications, e.g. mid-size pilot plants or manufacturing plants.

In some embodiments, a molar ratio of the glycidyl-containing alkoxysilane to the alkyl alkoxysilane in the solution ranges from 1:1 to 1:5, preferably 1:1.5 to 1:3, more preferably about 1:2; whereas a molar ratio of the alkyl alkoxysilane to the water in the solution ranges from 1:3 to 1:6, preferably 1:3.5 to 1:5, more preferably about 1:4.5.

Also, a volumetric ratio of ammonium hydroxide to the glycidyl-containing alkoxysilane may vary in the range of 1:2 to 1:6, preferably 1:3 to 1:5, preferably 1:4. A volumetric ratio of the glycidyl-containing alkoxysilane to the alcohol may vary in the range of 1:2 to 1:10, preferably 1:3 to 1:7, preferably about 1:5. For example, in one embodiment, 10 ml of ethanol is mixed with 0.5 ml of ammonium hydroxide, 2.0 ml of the glycidyl-containing alkoxysilane, 2.58 ml of the alkyl alkoxysilane, and 1.47 ml of water.

The solution may preferably be mixed and stirred for at least 20 minutes, preferably at least 30 minutes, preferably at least 45 minutes, but no more than 90 minutes, with a magnetic stirrer or a mechanical stirrer, or other stirring means known to those skilled in the art.

The alkyl alkoxysilane may be at least one selected from the group consisting of methyltrimethoxysilane, methyltriethoxysilane, dimethyldiethoxysilane, ethyltrimethoxysilane, trimethylethoxysilane, dimethyldimethoxysilane, propyltriethoxysilane, propyltrimethoxysilane, isobutyltriethoxysilane, hexyltrimethoxysilane, hexyltriethoxysilane, cyclohexyltriethoxysilane, cyclohexyltributoxysilane, heptyltrimethoxysilane, heptyltriethoxysilane, octyltrimethoxysilane, octyltriethoxysilane, methyloctyldimethoxysilane, methyloctyldiethoxysilane, nonyltrimethoxysilane, nonyltriethoxysilane, decyltrimethoxysilane, decyltriethoxysilane, dodecyltrimethoxysilane, dodecyltriethoxysilane, tetradecyltrimethoxysilane, tetradecyltriethoxysilane, octadecyltrimethoxysilane, octadecyltriethoxysilane, and mixtures thereof. In a preferred embodiment, the alkyl alkoxysilane is methyltrimethoxysilane. The glycidyl-containing alkoxysilane may be selected from (3-glycidyloxypropyl)trimethoxysilane and/or [2-(3,4-epoxycyclohexyl)ethyl]trimethoxysilane; however, in a preferred embodiment, the glycidyl-containing alkoxysilane is (3-glycidyloxypropyl)trimethoxysilane. The ammonium hydroxide may be present to catalyze condensation reactions that occur in the solution to form the mixture. In view of that, in some embodiments, one or more compounds may be utilized in lieu of ammonium hydroxide, wherein the one or more compounds may be selected from the group consisting of hydroxylamine, tetra-methyl ammonium hydroxide, tetra-ethyl ammonium hydroxide, tetra-propyl ammonium hydroxide, tetra-butyl ammonium hydroxide, pyridine, triethylamine, and tributylamine. The alcohol may be selected from the group consisting of methanol, ethanol, propanol, i-butanol, n-butanol, and phenol. Preferably, the alcohol is ethanol. The water may preferably be demineralized and/or deionized water.

The mixture may be applied onto the substrate using various methods known to those skilled in the art, for instance, brushing, dipping, drop-coating, pouring, spin-coating, or spray-coating. Referring to FIG. 8, in a preferred embodiment, the mixture is applied onto the substrate with spray-coating. Accordingly, an inert gas 810 (e.g. a nitrogen gas) with a pressure in the range of 200 to 400 kPa, preferably about 300 kPa, is passed through an internal cavity 806 of a spray gun 804 that is mounted across from the substrate. The spray gun is fluidly connected to a vessel 808 that contains a liquid 812 (i.e. the mixture or a suspension); therefore the inert gas 810 draws the liquid 812 and sprays the liquid 812 onto the substrate 902. A spray distance, i.e. the distance between the substrate and a nozzle of the spray gun as shown in FIG. 8, may be adjusted according to the pressure of the inert gas 810. For example, in some embodiments, the pressure of the inert gas is in the range of 200 to 400 kPa, preferably about 300 kPa, wherein the spray distance is in the range of 12 to 18 cm, preferably 14 to 16 cm, preferably about 15 cm. In some preferred embodiments, the substrate may be spray-coated with the liquid 812 (i.e. the mixture or the suspension) for at least one cycle but no more than six cycles, preferably two to four cycles, preferably three cycles. Each coating "cycle" is a movement of the spray gun from a first side of the substrate to a second side that is across from the first side, for example, from a left side of the substrate to a right side or from a top side to a bottom side. One layer of coating may deposit on the substrate after each cycle. Accordingly, five layers of coating may form on the substrate after five coating cycles, thereby a thicker coating may obtain. The substrate may preferably be spray-coated at room temperature (i.e. a temperature of 20 to 30° C., preferably 22 to 28° C., preferably about 25° C.). The liquid 812 may be applied onto the substrate in a time-interval fashion, when more than one cycle is spray-coated onto the substrate. Accordingly, each subsequent cycle is applied after a predetermined time interval with respect to a preceding cycle, wherein the predetermined time interval may preferably be less than 5 minutes, preferably less than 3 minutes, preferably less than 2 minutes. Alternatively, the predetermined time interval may be more than 5 minutes, or in the range of 30 to 60 minutes, or 40 to 50 minutes.

In some embodiments, an automatic spray gun is utilized to uniformly spray the mixture onto the substrate. For example, a spray atomizer may be employed to uniformly spray the liquid 812 (i.e. the mixture or the suspension) onto the substrate. The liquid 812 may be applied to only one side/surface, or two sides/surfaces, or multiple sides/surfaces of the substrate depending on the shape and geometry of the substrate. For example, in some embodiments, the substrate has a planar shape (e.g. a fabric) and the liquid 812 may be applied to one side/surface of the substrate, therefore the liquid 812 may cover 20% to 50%, preferably 30% to 49%/o, preferably 40% to 48% of the total surface area of the substrate; alternatively, in some embodiments the liquid 812 may be applied to both sides/surfaces of the substrate, therefore the liquid 812 may cover 50% to 100%, preferably 70% to 99%, preferably 80% to 98% of the total surface area of the substrate.

In some embodiments, the method further involves plasma treating the substrate with a plasma gas under a reduced pressure of 0.5 atm to vacuum, or 0.3 atm to 0.1 atm. As used herein, plasma refers to a matter that exists in the form of ions and electrons, which is formed by electrically charging a gas. As used herein, the term "plasma treatment" refers to a way of functionalizing a surface of a material by interacting ions and electrons with the surface. The plasma gas may be oxygen, argon, and/or nitrogen, and the substrate may be plasma treated for 1 to 5 minutes, or 2 to 4 minutes under the reduced pressure. The substrate may be washed with an organic solvent, e.g. acetone, ethanol, toluene, hydrochloric acid, hydrofluoric acid, etc. and water to clean the substrate before and/or after plasma treatment. For example, in some embodiments, the substrate is first plasma treated and then the substrate is washed with water and/or an alcohol, e.g. methanol, ethanol, and/or isopropanol to hydroxylate the substrate. Accordingly, in the embodiments where the binding layer is applied onto a substrate that does not include hydroxyl groups, e.g. paper, aluminum, steel, fabric, card board, etc., the substrate may be hydroxylated before applying the binding layer.

Figure 6:
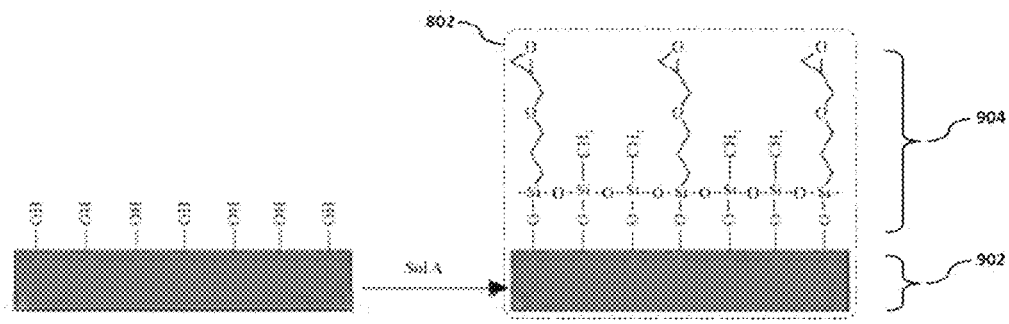
FIG. 6 illustrates a coated substrate that includes a binding layer on a substrate.

When the mixture is applied onto the substrate, in a next step, the substrate and the mixture that is applied may be heated, preferably in an inert atmosphere. Preferably, the substrate and the mixture may be heated at a temperature of 30 to 90° C., preferably 50 to 85° C., preferably 60 to 80° C., for no more than 3 hours, preferably no more than 2.5 hours, preferably about 2 hours. Also, the inert atmosphere may be provided by a glove-box or equipment/methods known to those skilled in the art. During the heating, the substrate may be functionalized with the alkyl alkoxysilane and the glycidyl-containing alkoxysilane, and thus a coated substrate 802 may be formed that contains a binding layer 904 that is chemically bound to the substrate 902, as shown in FIG. 6. The mixture, which is a sol-gel solution, may be solidified through a sol-gel process, wherein monomers present in a colloidal solution or a sol (i.e. the mixture) may convert into an integrated network (or a gel) of either discrete particles or network polymers. Transformations of the alkoxysilanes may be carried out through a series of hydrolysis, water condensation, and alcohol condensation reactions. Preferably, epoxide groups of the glycidyl-containing alkoxysilane are not reacted during heating, and therefore, the binding layer 904 contains epoxide groups, as shown in FIG. 6. Hydrolysis, water condensation, and alcohol condensation reactions of an alkyl alkoxysilane (R is an alkyl group) is shown in the reaction schemes below.

Hydrolysis:

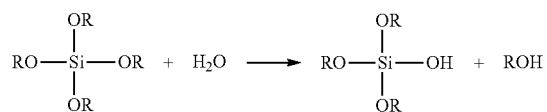

Water Condensation:

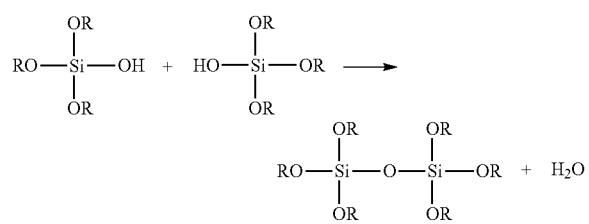

Alcohol Condensation:

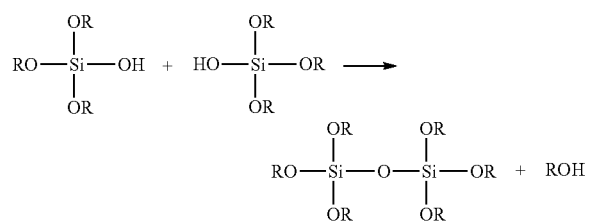

In addition, hydrolysis, water condensation, and alcohol condensation reactions of methyltrimethoxysilane are shown in the reaction schemes below.

Hydrolysis:

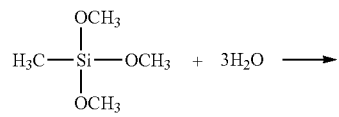

-continued

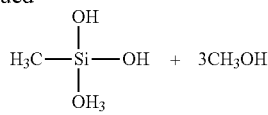

Water Condensation:

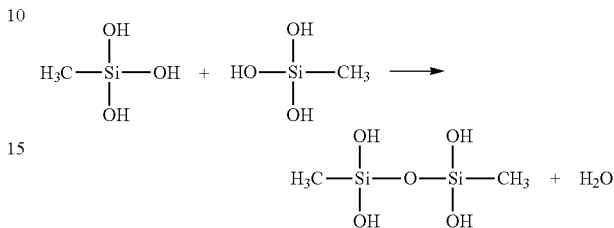

Alcohol Condensation:

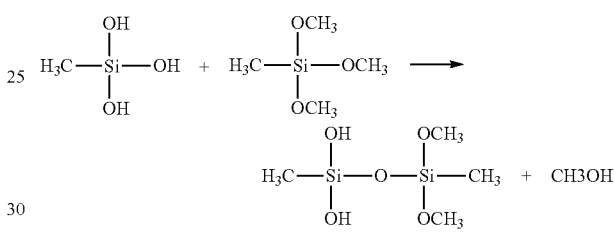

Due to the presence of hydrolyzable Si—OH functional groups and/or Si—OCH$_3$ functional groups, a 3D gel network may form on the substrate after a series hydrolysis and condensation reactions. As a result, a surface of the substrate may be covered by low surface energy functional groups, e.g. Si—CH$_3$.

The binding layer may be present on one side/surface, or two sides/surfaces, or multiple sides/surfaces of the substrate depending on the shape and geometry of the substrate. For example, in one embodiment, the substrate has a planar shape (e.g. a car windshield) and the binding layer is only present on one side/surface of the substrate, wherein the binding layer covers 20% to 50%, preferably 30% to 49%, preferably 40% to 48% of the total surface area of the substrate. In another embodiment, the binding layer is present on both sides/surfaces of the substrate, wherein the binding layer covers 50% to 100%, preferably 70% to 99%, preferably 80% to 98% of the total surface area of the substrate.

The method further involves applying a suspension comprising perfluoroalkyl-functionalized silica nanoparticles 704 onto the coated substrate 802 to form a hydrophobic layer 906 on the binding layer 904, thereby forming the substrate with the superhydrophobic coating. In a preferred embodiment, the suspension is immediately applied onto the coated substrate 802 after the heating step. As used herein, the term "immediately applied" refers to the embodiments where a time interval between the heating step and the step of applying the suspension is no more than 5 minutes, or preferably no more than 3 minutes, more preferably no more than 1 minute. Preferably, the suspension is immediately applied to avoid oxidation of functional groups (particularly hydroxyl groups) that are present in the binding layer 904 of the coated substrate 802, as shown in FIG. 6. In some embodiments, the coated substrate is kept in the inert atmosphere, and the suspension may be applied after about 30 minutes, preferably about 45 minutes, but preferably no more than 60 minutes after the heating. A binding between the binding layer 904 and the hydrophobic layer 906 may be due to the existence of hydrogen bonding between epoxide groups present in the binding layer and hydroxyl groups present in the perfluoroalkyl-functionalized silica nanoparticles and/or silica nanoparticles of the hydrophobic layer 906. In addition, the binding may be due to the formation of chemical bonds between the epoxide groups and the hydroxyl groups.

Figure 7:
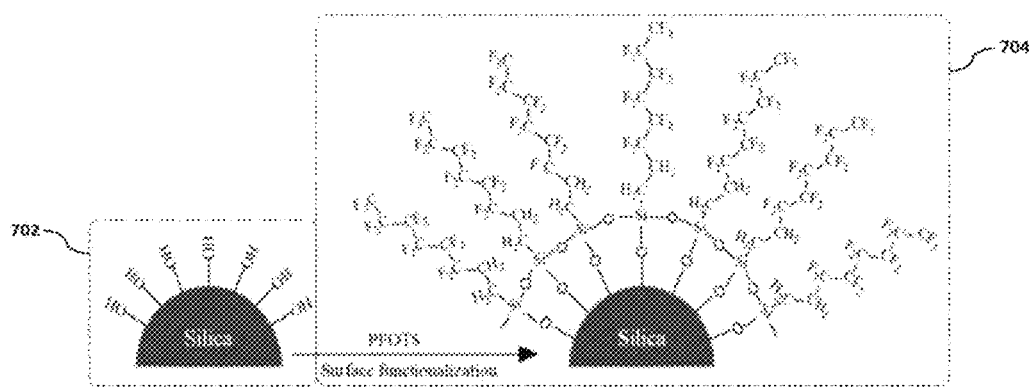
FIG. 7 illustrates a silica nanoparticle and a perfluoroalkyl-functionalized silica nanoparticle.

The perfluoroalkyl-functionalized silica nanoparticles 704 present in the suspension may be formed by sonicating silica nanoparticles 702 in the presence of a perfluoroalkylsilane. FIG. 7 shows a schematic of a perfluoroalkyl-functionalized silica nanoparticle 704 that is formed from a silica nanoparticle 702. In one embodiment, the perfluoroalkylsilane may be selected from the group consisting of (heptadecafluoro-1,1,2-2-tetrahydrodecyl)triethoxysilane, (3,3,3-trifluoropropyl)trimethoxysilane, heptadecafluoro-1,1,2,2-tetrahydrodecyl)trichlorosilane, chlorodimethyl(pentafluorophenyl)silane, chloromethyl)methylbis(pentafluorophenyl)silane, diisopropyl(3,3,4,4,5,5,6,6,6-nonafluorohexyl)silane, diisopropyl(3,3,4,4,5,5,6,6,7,7,8,8,8-tridecafluorooctyl)silane, trichloro(3,3,3-trifluoropropyl) silane, trichloro(3,3,4,4,5,5,6,6,7,7,8,8,8-tridecafluorooctyl) silane, triethoxy(4-(trifluoromethyl)phenyl)silane, tridecafluoro-1,1,2,2-tetrahydrooctyl)trimethoxysilane, and combinations thereof. In a preferred embodiment, the perfluoroalkylsilane is 1,1,2,2-perfluorooctyltriethoxysilane.

In a preferred embodiment, a weight percent of the perfluoroalkyl-functionalized silica nanoparticles 704 in the suspension is in the range of 0.1 wt % to 2.0 wt %, preferably 0.5 wt % to 2.0 wt %, preferably about 1.0 wt %, relative to the total weight of the suspension. In an alternative preferred embodiment, a weight percent of the silica nanoparticles 702 in the suspension is in the range of 0.1 wt % to 2.0 wt %, preferably 0.5 wt % to 2.0 wt %, preferably about 1.0 wt %, relative to the total weight of the suspension. In one embodiment, the silica nanoparticles 702 have an average diameter in the range of 1 to 100 nm, preferably 2 to 90 nm, preferably 5 to 80 nm. In some embodiments, the suspension may further include one or more organosilicon compounds, which may be an orthosilicate. Exemplary orthosilicates include, but are not limited to, tetraethyl orthosilicate, tetramethyl orthosilicate, tetrapropyl orthosilicate, tetrabutyl orthosilicate, tetraallyl orthosilicate, tetrakis(dimethylsilyl) orthosilicate, tetraamyl orthosilicate, and the like. In a preferred embodiment, the organosilicon compound is tetraethyl orthosilicate (TEOS). When present, a weight percent of the organosilicon compounds in the suspension may preferably be in the range of 0.1 wt % to 2.0 wt %, preferably 0.2 wt % to 1.5 wt %, preferably 0.3 wt % to 1.0 wt %, relative to the total weight of the suspension.

Preferably, the perfluoroalkylsilane may first be mixed with the silica nanoparticles 702 and optionally the organosilicon compounds in the presence of an alcohol, e.g. methanol, isopropanol, isobutanol, preferably ethanol, to form the suspension. Then, the suspension may be sonicated, preferably ultra-sonicated with an ultrasound sonication device, for at least 90 minutes, preferably at least 120 minutes, but no more than 180 minutes. Surface functionalization of the silica nanoparticles 702 may preferably take place during sonication. In some embodiments, at least 80 wt %, preferably at least 85 wt %, preferably at least 90 wt % of the silica nanoparticles that are mixed with the perfluoroalkylsilane may be perfluoroalkyl-functionalized. In view of that, at least 80 wt %, preferably at least 85 wt %, preferably at least 90 wt % of the total nanoparticles that are present in the hydrophobic layer are perfluoroalkyl-functionalized silica nanoparticles 704, while less than 20 wt %, preferably less than 15 wt %, preferably less than 10 wt % of the total nanoparticles that are present in the hydrophobic layer are silica nanoparticles 702. Sonication may also be useful if an inhomogeneous mixture is formed after hydrolysis of the perfluoroalkylsilane on the silica nanoparticles in the suspension. An inhomogeneous mixture may be formed due to aggregation of the silica nanoparticles 702 and/or aggregation of the perfluoroalkyl-functionalized silica nanoparticles 704. A milky or a cloudy appearance may be indicative of an inhomogeneous mixture. Sonicating the suspension may disrupt these aggregations and allow the perfluoroalkyl-functionalized silica nanoparticles 704 to be homogeneously dispersed in the suspension. A clear and transparent appearance may be indicative of a homogeneous mixture.

The binding layer 904 provides durability and stability to the superhydrophobic coating 900 by immobilizing the perfluoroalkyl-functionalized silica nanoparticles 704 on the surface of the superhydrophobic coating 900, whereas the perfluoroalkyl-functionalized silica nanoparticles 704 reduce the surface energy of the superhydrophobic coating due to the presence of perfluoroalkyl functional groups. The perfluoroalkyl-functionalized silica nanoparticles 704 further increase the surface roughness of the superhydrophobic coating.

In some embodiments, depending on a composition of the suspension the hydrophobic layer may further include one or more of a fluorocarbon, a perfluorocarbon, a resin, a hydrophobic fatty acid, and a hydrophobic self-assembled monolayer. Exemplary fluorocarbons and perfluorocarbons may include, but are not limited to, i) fluoroalkanes such as carbon tetrafluoride, perfluoroocatane, perfluoro-2-methylpentane, perfluorooctanoic acid, perfluoro-1,3-dimethylcyclohexane, perfluorodecalin, hexafluoroethane, perfluoropentane, pefluoromethylcyclohexane, perfluoro-1,3-dimethylcyclohexane, perfluoromethyldecalin, ii) fluoroalkenes/fluoralkynes such as perfluoroisobutene, tetrafluoroethylene, hexafluoropropylene, hexafluorobutyne, iii) perfluoroaromatic compounds such as hexafluorobenzene, octafluorotoluene, and octafluoronaphthalene, and iv) fluoropolymers such as polyvinylfluoride, polyvinylidene fluoride, polytetrafluoroethylene, polychlorotrifluoroethylene, fluorinated ethylene-propylene, perfluropolyether, perfluoropolyoxetane, pefluoroalkoxy polymer, polyethylenetetrafluoroethylen, polyethylenechlorotrifluoroethylene, and the like. Exemplary resins may include, but are not limited to, films or resins made from carbon layers or carbon sheets, phenolic resins, epoxy resins (e.g. bisphenol A and F epoxy resins, glycidylamine epoxy resin, aliphatic epoxy resin, etc.), polystyrene, poly(methylmethacrylate), a manganese-oxide/polystyrene ($MnO_2$/PS) nanocomposite, a zinc-oxide/polystyrene (ZnO/PS) nanocomposite, calcium carbonate, carbon nanotubes, silica nano-coatings, nano-pin films, and the like. The hydrophobic fatty acids may include, but are not limited to propanoic acid, butanoic acid, pentanoic acid, hexanoic acid, heptanoic acid, octanoic acid, nonanoic acid, decanoic acid, undecanoic acid, dodecanoic and, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, hexatriacontanoic acid, and combinations thereof. As used herein, the term "hydrophobic self-assembled monolayer" refers to a molecular assembly that forms spontaneously on a surface by adsorption, and is organized into an ordered domain. Preferably, the hydrophobic self-assembled monolayer may not interact strongly with the substrate, however the hydrophobic self-assembled monolayer may possess a head group that has a strong affinity for the substrate and may anchor the molecule to the substrate. Exemplary hydrophobic self-assembled monolayers include, but are not limited to, (11-mercatoundecyl)tetra(ethylene glycol), [11-(methylcarbonylthio)undecyl]-tetra-(ethylene glycol), tetra (ethylene glycol) dithiol, 1-hexadecanethiol, and the like.

In one embodiment, the suspension may be applied onto the coated substrate 802 by any one of the coating methods known to those skilled in the art, e.g. brushing, dip-coating, drop-coating, pouring, spin-coating or spray-coating. In a preferred embodiment, the suspension may be spray-coated onto the coated substrate 802, wherein spray-coating of the suspension is substantially similar to the spray-coating of the mixture, which is described and illustrated in FIG. 8. In some embodiments, the suspension may be spray-coated onto the coated substrate 802 for at least one cycle but no more than 10 cycles, preferably two to six cycles, preferably five cycles, in the time-interval fashion, wherein a thickness of the hydrophobic layer may be in the range of 10 nm to 500 μm, preferably 20 nm to 400 μm, preferably 50 nm to 300 μm. The suspension may be applied to only one side/surface, or two sides/surfaces, or multiple sides/surfaces of the substrate depending on the shape and geometry of the substrate. For example, in some embodiments, the substrate has a planar shape (e.g. a car windshield or a fabric) and the suspension may be applied to one side/surface of the substrate. Accordingly, the hydrophobic layer may cover 20% to 50%, preferably 30% to 49%, preferably 40% to 48% of the total surface area of the substrate; alternatively, in some embodiments the suspension may be applied to both sides/surfaces of the substrate, and therefore the hydrophobic layer may cover 50% to 100%, preferably 70% to 99%, preferably 80% to 98% of the total surface area of the substrate. In a preferred embodiment, the hydrophobic layer may completely cover the binding layer, whereas in some alternative embodiments, a total surface area of the hydrophobic layer is less than a total surface area of the binding layer.

Once the suspension is applied onto the coated substrate 802, the substrate with the superhydrophobic coating may be annealed at a temperature in the range of 100° C. to 300° C., preferably 110° C. to 200° C., preferably 120° C. to 150° C., for no more than 2 hours, preferably no more than 1.5 hours, preferably no more than 1 hour. Alternatively, the substrate with the superhydrophobic coating may be maintained at room temperature (i.e. a temperature of 20 to 30° C., preferably 22 to 28° C., preferably about 25° C.) for 20 to 30 hours, preferably about 24 hours. Accordingly, a portion of the perfluoroalkyl functional groups of the perfluoroalkyl-functionalized silica nanoparticles 704 present in the hydrophobic layer 906 may reorient to form a thermodynamically stable arrangement during annealing the substrate with the superhydrophobic coating. As a result of annealing, an average contact angle of a water droplet on the superhydrophobic coating may rise to a value in the range from about 150° to about 175°, preferably from about 155° to about 174°, preferably from about 160° to about 173°, and an average surface energy of the superhydrophobic coating may drop to a value in the range of preferably about 4 to 7 mJ/m$^2$, more preferably about 5 to 7 mJ/m$^2$.

The examples below are intended to further illustrate protocols for the substrate with the superhydrophobic coating and the method of fabricating thereof, and are not intended to limit the scope of the claims.

Example 1—Materials and Fabrication of Superhydrophobic Surfaces

The materials used to fabricate the intended robust superhydopohobic and self-cleaning surfaces are: 1) Silicon dioxide (nanopowder, 10-20 nm particle size (BET), 99.5% trace metals basis), 2) Methyltrimethoxysilane (MTMS), (3-Glycidyloxypropyl) trimethoxysilane (GLYMO), 1,1,2,2-Perfluorooctyl-trichlorosilane (PFOTS), 3) ethanol, 4) acetone, 5) Ammonia (30 Vol %). All of these chemicals were purchased from Sigma-Aldrich, Germany. FIG. 5 shows the molecular structure of the MTMS, GLYMO and PFOTS used in our experiments. The deionized (DI) water used during the experiment was collected from the Milli-DI® Water Purification System.

The coatings are prepared by the sol-gel method. Accordingly, coating solution A (referred to as Sol A) is prepared by adding the following chemicals into the beaker during magnetic stirring at a constant speed throughout the synthesis process. Molar ratio of GLYMO:MTMS:DI=1:2:9 adopted which is corresponding to the amount of Ethanol (10 ml), Ammonia (0.5 ml), GLYMO (2 ml), MTMS (2.58 ml) and DI water (1.47 ml). All of these chemicals were added to the beaker dropwise meanwhile stirring with magnetic stirrer. Beaker covered with the Aluminum foil to avoid reduction of solution by evaporation and solution stirred for 1 hour. After preparation of sol A, it was used immediately after 1 hour of stirring, otherwise after few hours or few days, the sol A becomes gel depending upon the amount of NH$_4$OH catalysis was added to Sol A. FIG. 6 shows how Sol A bonds to a glass surface. First of all, both MTMS and GLYMO in Sol A have three hydrolysable methoxy groups (—OCH3) sites hydrolyzed and substituted by hydroxyl groups (—OH). Hydroxyl groups on MTMS, GLYMO and glass through condensation reaction chemically bonded.

Coating sol B prepared with different weight percentage of silica nanoparticles functionalized by PFOTS in the ethanol as a solvent. FIG. 7 shows a schematic of functionalized silica particles that are surface functionalized by PFOTS.

Sol B with different percentage of silica was prepared as presented in the Table 2. Sol B consisting of ethanol, PFOTS and different weight percentage of silica sonicated in the ultrasonic bath for 2 hours. Sol B was kept in sealed bottle and was used as second layer after first layer of Sol A.

TABLE 2

Solution B composition for different weight percentage of silica.

| SiO2 wt % in Sol B | Ethanol (g) | Silica (g) | PFOTS (g) |
|---|---|---|---|
| 0 wt % | 9.8 | 0 | 0.2 |
| 0.5 wt % | 9.75 | 0.05 | 0.2 |
| 1.0 wt % | 9.7 | 0.1 | 0.2 |
| 2.0 wt % | 9.6 | 0.2 | 0.2 |

Prior to spray coating, new glass slides were cut into 25×25 mm pieces and thoroughly cleaned by first sonicating them in acetone followed by DI water for 10 minutes each then dried before spray coating them.

Figure 8A:
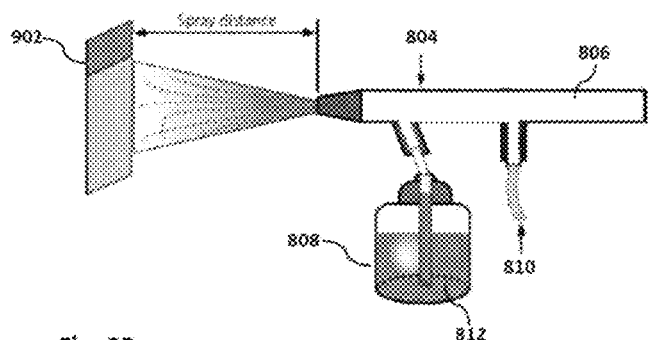
FIG. 8A illustrates a spray-coating setup to apply a coating onto a substrate.

The spray coating process was performed by BADGER NO 150 (USA) spray gun and the setup is illustrated in FIG. 8(a). First, the jar containing Sol A was connected to the spray gun with the gas inlet connected to nitrogen cylinder to apply constant pressure of 300 kPa during the spray coating process. The distance between the glass slides and spray gun tip was also one of the important parameter that can affect the uniformity of the film deposited on the glass substrate surface. If the spray gun is too far, sprayed solution will be wasted before reaching the surface of the glass under constant pressure. If the spray gun is too near, sprayed solution concentrates on the center of the surface. Thus, proper spray distance was chosen for getting uniform film on glass surface. First, the spray distance is set to 15 cm then Sol A was sprayed on the glass slides with 3 cycles. After coating the glass slides with Sol A, samples were carefully put in the oven at 80° C. for 2 hours to evaporate the ethanol solvent completely.

One spray cycle defined as follows: first step, glass substrate was fixed vertically as showed in FIG. 8(a). Spray gun was manually traveled from right/left side to left/right side of glass, solution was deposited on the glass surface during the spray gun travel (scan) through on it.

Figure 8B:
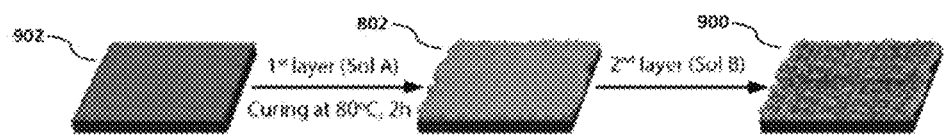
FIG. 8B illustrates a substrate after coating with a mixture (sol A) and a suspension (sol B).

After complete curing of the first layer Sol A, the glass slides were immediately sprayed with second layer of Sol B to functionalize the surface as well as to increase the roughness; schematic illustration of the process shown in FIG. 8(b). After completion of the surface modification, the glass substrate can either be cured at a certain temperature for certain time or kept at room temperature for 24 hours. In both cases, the PFOTS molecules need time to re-arrange their molecules to reach thermodynamic stable state. See M. Psarski, J. Marczak, G. Celichowski, G. B. Sobieraj, K. Gumowski, F. Zhou, W. Liu, and V. sp oo, "Hydrophobization of epoxy nanocomposite surface with 1,1,2,2-perfluorooctyltrichlorosilane for superhydrophobic properties," Cent. Eur. J. Phys., vol. 10, no. 5, pp. 1197-1201, 2012. In this study, glass slides were kept at room temperature for 24 hours after the deposition of second layer of Sol B. After this process, the surface becomes chemically stable and water contact angle measurements can be conducted. It is worth mentioning that the second layer which is Sol B should be immediately deposited after curing of the first layer. This is to avoid oxidation of the functional groups such as —OH of the first layer which are responsible for the condensation reaction that occurs between the two different layers.

After the deposition of the second layer Sol B which consists of silica nanoparticles surface functionalized by PFOTS, the samples were cured at certain temperature for specific time period. Thereafter, they were maintained at the room temperature for longer time to enable the proper alignment and arrangement of low surface energy —$CF_2$, —$CF_3$ functional groups to the surface as reported in the literature. Usually, it takes approximately up to 24 hours for PFOTS to rearrange itself so that low surface energy groups such as —$CF_3$ get arranged outward decreasing the total surface energy of the coating layer. As illustrated in the FIG. 9, first layer coating bonded with glass surface. Second layer of functionalized silica nanoparticles imbedded in the first layer coating.

In this study, annealing at 60° C. for 3 hours, annealing at 80° C. for 2 hours, or even keeping it at room temperature for approximately 24 hours, showed similar results. If the water contact angle was measured directly after application of second layer Sol B without annealing or waiting at room temperature for approximately 24 hours, the angle decreased with time and a transition from superhydrophobic to hydrophilic behavior was observed within very short time. It took only a few minutes for the contact angle to decrease from more than 150° to approximately 900 or below.

Table 3 gives the nomenclature for the samples coated with second layer of Sol B with different weight percentage of silica and different spraying cycles (1-5 cycles).

TABLE 3

Samples identification (name) according to silica weight percentage and spray cycles.

| SiO2 wt % | Spray cycles | | | | |
|---|---|---|---|---|---|
| | 1 | 2 | 3 | 4 | 5 |
| 0 | B0-1 | B0-2 | B0-3 | B0-4 | B0-5 |
| 0.5 | B0.5-1 | B0.5-2 | B0.5-3 | B0.5-4 | B0.5-4 |
| 1.0 | B1-1 | B1-2 | B1-3 | B1-4 | B1-5 |
| 2.0 | B2-1 | B2-2 | B2-3 | — | — |

Example 2—Characterization

A contact angle goniometer (Kyowa Interface, Inc. Japan) was used to determine the static water contact angle, sliding angle, advancing and receding contact angle, as shown in FIGS. 1(a) and 1(b). The hysteresis was calculated according to equation (I). The sessile drop model was used with the tangential method to measure the static water contact angles in a proper manner. Approximately 10 μl water droplets were carefully placed on the surface and the angle was measured from the captured image. Measurements, from different locations on the surface, were repeated at least 5 times for each sample to obtain an average value that was representative for the sample.

Figure 10:
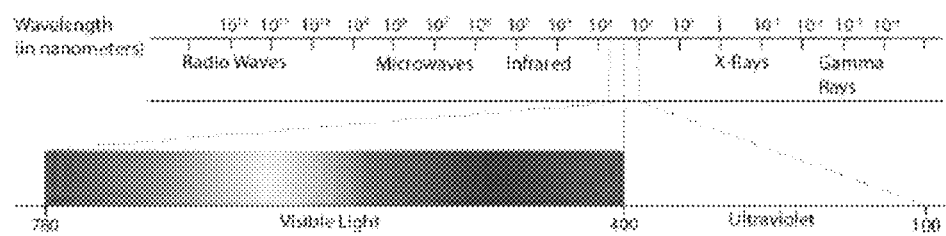
FIG. 10 illustrates a wavelength spectrum of light.

UV-VIS spectrophotometer (JASCO, V-670) was used to measure the transmittance of the spray coated glass slides in the visible light wavelength range of 400 to 780 nm as shown in FIG. 10. Transmittance of the surface to visible light is important for the fabricated surface since the intended use is mainly for self-cleaning of Solar PV panels.

Surface morphology was studied with a field emission scanning electron microscope (FESEM, TESCAN). Prior to analysis, the samples were coated with gold to make the surfaces electrically conductive. The elemental composition of selected locations was analyzed using Energy Dispersive Spectroscopy (EDS).

Surface topography was characterized by 3D optical microscopy (Bruker Inc. Germany). Each of the samples analyzed at 3 different locations and the average value is reported.

The Raman spectra of selected samples were recorded with DXR Raman Spectrometer (Thermo Scientific) using a 455 nm laser source. By analyzing the Raman spectra functional groups presented at the surface examined and confirmed.

FTIR spectra were obtained using a Nicolet is50 spectrometer (Thermo Scientific) with an ATR accessory. FTIR spectroscopy was used to analyze the functional groups presented on the surface. FTIR spectroscopy was also used to determine the functional groups at different annealing temperature and effect of annealing can be examined.

X-ray Photoelectron Spectroscopy (XPS) was carried out to determine the surface atomic concentration. The data were collected on a Thermo Escalab 250 probe system equipped with an aluminum anode to produce a focused X-ray beam. The diameter of the X-ray spot was about 500 μm. The equipment contained a spherical capacitor energy analyzer and a multichannel detector. Surface survey scans were collected, followed by high resolution scans for Carbon, Oxygen, Silicon and Fluorine.

Ultraviolet Resistance Test

Figure 11A:
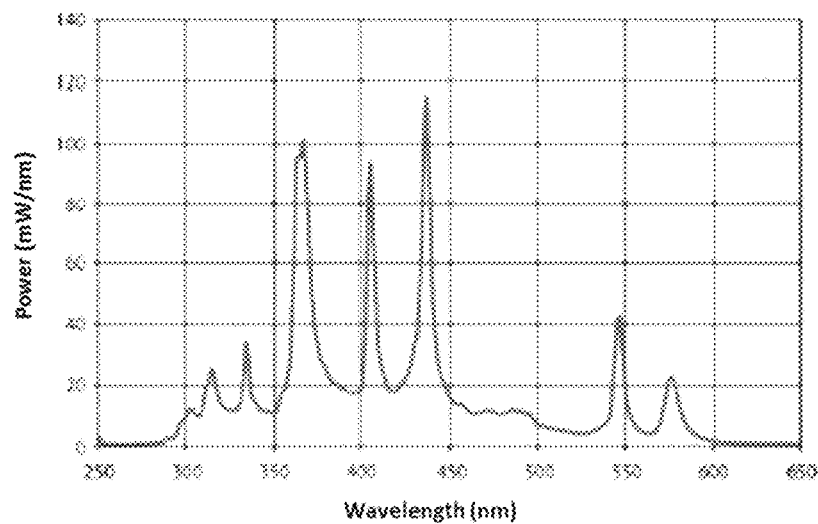
FIG. 11A illustrates a power spectrum of a UV lamp.
Figure 11B:
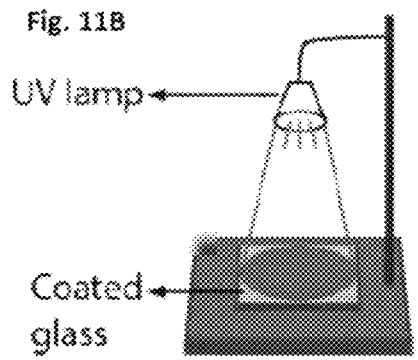
FIG. 11B illustrates a UV lamp setup.

OmniCure S2000 UV spot curing system (EXCELITAS TECHNOLOGIES) was used to study the UV resistance of the coating and OmniCure R2000 radiometer was employed to measure the light intensity reaching the surface of the coated glass substrate. Samples were placed under the UV light source and a radiometer was used to measure the light intensity that reached sample surface. FIG. 11(a) Power spectra of the OmniCure S2000 UV lamps, FIG. 11(b) showing illustration of Sample placed under the UV light for testing the UV resistance. Sample B1-3 was tested under a UV light intensity of 2500 W/m$^2$ (250 mW/cm$^2$) for 10 hours and followed by exposure to a very high UV light intensity of 30000 W/m$^2$ (3000 mW/cm$^2$) for 2 hours.

Thermal Stability Test

Selected sample B1-3 tested for thermal stability at different temperature of 300° C., 350° C. and 400° C. First, oven was heated to the intended temperature then at least three samples of b1-3 for each temperature placed in the oven for 2 hours annealing. After annealing, the contact angle of the samples were measured and characterized by FTIR.

Water Jet Test

Water jet test schematic is illustrated in FIG. 12. Water was flow continuously at the rate of 1 L/min through a 4 mm diameter tube impacting the surface. Coated glass was placed under water jet for 1 hour and total volume of 60 L water was consumed during the water jet test. Adjustable stick was properly adjusted so that distance between water tube tip to surface of the glass was tested which is D2 adjusted to 15 cm and D1 about 10 cm as showed in the illustration.

Abrasion Resistance Test

Sample was placed on the BUEHLER 240 GRIT size sand paper with the coated surface in contact with the sand paper and on top of glass surface placed 100 g of weight. Abrasion test was conducted as illustrated in FIG. 13. In the first step, the sample traveled a distance of 10 cm on the sand paper and the glass slide horizontally was rotated 90°. In the second step, it traveled back to original position with traveling distance of 10 cm. These two steps were considered as one cycle. Total of 5 cycles of abrasion test were conducted that is corresponds to a total traveling distance of 100 cm. According to the glass piece size of 25×25 mm and 100 g of weight on it, applied pressure on the surface during the test was about 1.6 kPa.

Sand Blasting Test

An air pressure of approximately 300 kPa was applied to blow sand through a 6 mm nozzle opening. Sample surface to nozzle tip distance was adjusted to about 15 cm. As shown in FIG. 14, sand particles are continuously fed from the sand container and hitting the coated glass surface. More than 300 g of sand particles were blown on the surface in about 10 minutes duration.

Example 3—Spray Coating Parameters

For a uniform deposition of the coating solution on the glass surface, it is important to control the spray coating parameters within specific limits. Since transmittance of the glass substrate after the application of coating is important, each coating layer should be applied such that the decrease in transmittance is minimized. As mentioned, spray gun distances (10 and 15 cm) and five cycles (layers) were considered. FIGS. 15(a) and 15(b) show how each of the cycles (coating layers) of solution A affects the glass transmittance for both distances. Spraying of Sol A was performed immediately after 1 hour of stirring, otherwise Sol A viscosity increased and it transformed to gel with time as sol-gel reaction is taking place. As indicated in the FIGS. 15(a) and 15(b), transmittance of coated glass with sol A (Sol A was sprayed after 24 hours after sol A prepared). It is obvious that the coating reduces the transmittance and the thicker the coating the lower the transmittance is. The application of first layer on the glass surface compromised the transmittance by more than 25% for 10-cm and more than 20% for 15 cm. The decrease in transmittance is ascribed to the high viscosity of the Sol A.

Figure 16:
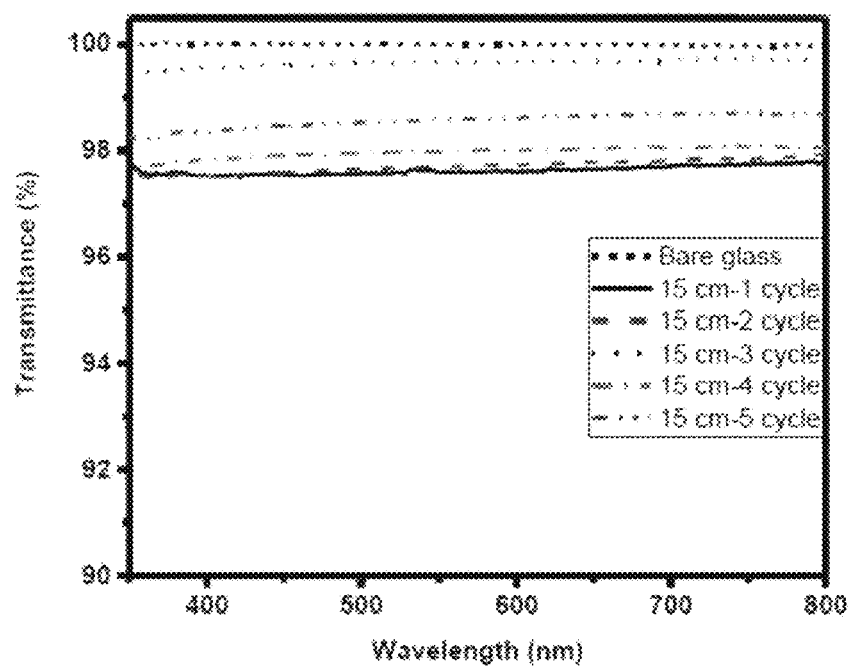
FIG. 16 represents transmittance spectra of the coated substrate immediately after preparation, wherein the substrate is spray-coated at a spray distance of 15 cm.

In general, spraying from a distance of 15 cm resulted in a better transmittance for all cycles when compared with the spraying distance of 10 cm. When highly viscous Sol A is sprayed over the glass surface, tiny droplets are formed rather than a continuous coating. Formation of droplets may account for the decrease in the transmittance by approximately 20% at a 15 cm spray distance and only with one spray cycle. The results show that, to get a smooth first layer, Sol A should be sprayed immediately after synthesis process to avoid gelation which gives rise to high viscosity. Thus, Sol A was sprayed immediately after the synthesis process from a distance of 15 cm. FIG. 16 shows how transmittance is varied by multiple cycles of spray-coating with a spray distance of 15 cm. The decrease in transmittance of the glass could be maintained at levels which are within 2-3% of that of the bare glass. By comparing FIG. 15(a), 15(b), and FIG. 16, one may conclude that the viscosity of the solution affects the spray coating process and spraying of the viscous solution may form tiny droplets on the surface rather than uniformly spread over the glass surface and increased the light reflectance. To avoid compromising on transmittance of the glass, sol A was used right after it prepared before sol A. It is evident from our experiment that, significant increase in viscosity should be avoided.

Based on FIG. 15(a), 15(b), and FIG. 16, it was decided to 3 cycles of Sol A with pressure of 300 kPa and at a spray distance of 15 cm. It is clear from the FIG. 16, that transmittance of 3 cycles is very close to glass. Similar to application of sol A, for application of sol B, spray pressure of 300 kPa and spray distance of 15 cm was adopted.

Example 4—Effect of Silica Nanoparticles on Hydrophobicity and Transmittance

Following adjusting of the spraying process of Sol A in terms of optical properties, the coating hydrophobicity is studied.

The second layer of Sol B with different weight percentage (0%, 0.5%, 1.0% and 2.0%) of silica nanoparticles was sprayed on the surface immediately after curing of first layer. Static, sliding, advancing, receding angles and hysteresis were measured accordingly. When the water droplet on the surface start sliding within the tilting degree of 300 then the sliding angle, advancing angle, receding angle and hysteresis were reported otherwise only static water contact angle was reported and other details reported as a NA (Not Available). These results are separately listed in Tables 4, 5, 6, and 7.

TABLE 4

Contact angle of the samples sprayed with
Solution B without silica Nanoparticles.

| Samples | CA | SA | Advancing Angle (AA) | Receding Angle (RA) | Hysteresis (H) |
|---|---|---|---|---|---|
| B0-1 | 108.5 ± 1.8 | NA | NA | NA | NA |
| B0-2 | 110.2 ± 1.1 | NA | NA | NA | NA |
| B0-3 | 111.6 ± 0.7 | NA | NA | NA | NA |
| B0-4 | 113.8 ± 1.4 | NA | NA | NA | NA |
| B0-5 | 114.2 ± 1.1 | NA | NA | NA | NA |

When the second layer applied without silica nanoparticles, there is no significant change in the static contact angle with the increase of the spray cycles. The results indicating that even 1 to 2 cycles spraying of second layer Sol B can be enough for the functionalization of the surface with low surface energy functional groups. Without inducing surface roughness and by only modifying the surface chemistry, the highest reported static water contact angle did not exceed 120°.

TABLE 5

Contact angle of the samples sprayed with Solution
B including 0.5 wt % silica Nanoparticles.

| Samples | CA | SA | Advancing Angle (AA) | Receding Angle (RA) | Hysteresis (H) |
|---|---|---|---|---|---|
| B0.5-1 | 117.9 ± 2.8 | NA | NA | NA | NA |
| B0.5-2 | 121.3 ± 3.6 | NA | NA | NA | NA |
| B0.5-3 | 129.9 ± 3.7 | NA | NA | NA | NA |
| B0.5-4 | 138.6 ± 2.3 | NA | NA | NA | NA |
| B0.5-5 | 144.0 ± 2.4 | 18.8 ± 4.3 | 146.2 ± 2.9 | 120.7 ± 7.9 | 25.5 ± 7.3 |

Figure 17A:
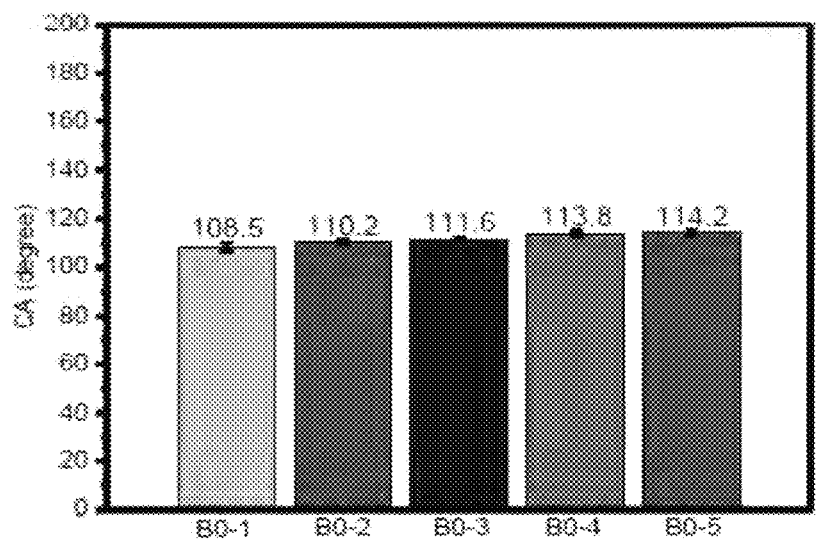
FIG. 17A represents a water contact angle of the superhydrophobic coating, wherein the hydrophobic layer does not include silica nanoparticles and/or perfluoroalkyl-functionalized silica nanoparticles.
Figure 17B:
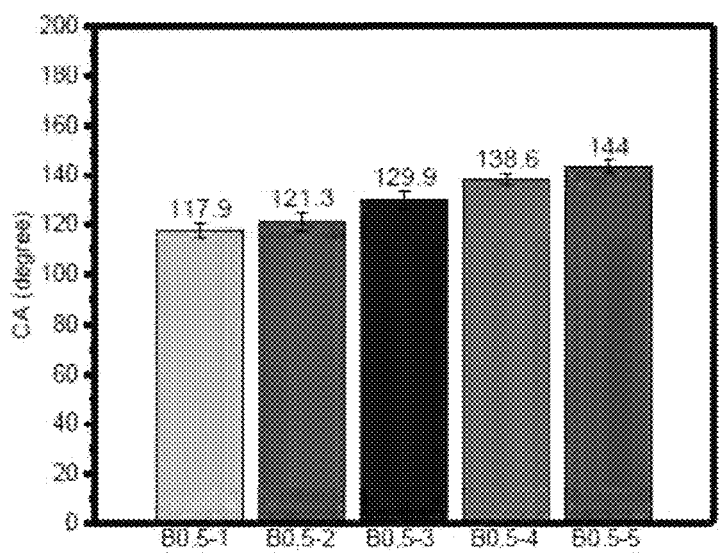
FIG. 17B represents a water contact angle of the superhydrophobic coating, wherein the hydrophobic layer includes silica nanoparticles and/or perfluoroalkyl-functionalized silica nanoparticles.

According to the FIG. 17A and FIG. 17B, it can be observed that the addition of the 0.5 wt % silica nanoparticles to Sol B, increases the static CA by about 100 (from 108 to 118°) when Sol B sprayed on the surface at only one cycle. More Sol B deposition brought about more surface functionalized silica nanoparticles on the surface and smooth surface become rougher as the deposition cycle increases. The results indicate that by tuning the roughness of the surface, it can become ultra-hydrophobic and further tuning of the roughness to a preferable level, surface can exhibit superhydrophobic properties. This conclusion become more convincing when Sol B applied with 1 wt % silica, and only 3 cycles of spraying made the surface superhydrophobic with very low sliding angle and hysteresis. These results are further proof of the importance of surface roughness for the hydrophobicity. It is only by designing desirable surface roughness that a surface can change from hydrophobic to superhydrophobic state. FIG. 18 shows the state of a water droplet and corresponding static contact angle on the bare glass (uncoated glass substrate) and coated samples with 1.0 wt % silica nanoparticles.

TABLE 6

Static, sliding, advancing, and receding angles and hysteresis of the
samples sprayed with Solution B including 1 wt % silica Nanoparticles.

| Samples | CA | SA | AA | RA | H |
|---|---|---|---|---|---|
| B1-1 | 126.8 ± 4.6 | 15.4 ± 2.3 | 131.1 ± 2.6 | 116.3 ± 4.2 | 14.8 ± 3.6 |
| B1-2 | 136.2 ± 4.8 | 23 ± 4.5 | 141.8 ± 5.8 | 113.9 ± 7.7 | 27.9 ± 4.7 |
| B1-3 | 169.1 ± 1.0 | 1 ± 0 | 165.9 ± 2.5 | 159.4 ± 1.4 | 6.5 ± 1.8 |
| B1-4 | 168.7 ± 2.8 | 1 ± 0 | 166 ± 1.4 | 160.4 ± 2.9 | 5.5 ± 2.5 |
| B1-5 | 170.6 ± 1.1 | 1 ± 0 | 167.3 ± 0.9 | 162.7 ± 3.0 | 4.6 ± 2.5 |

Figure 19:
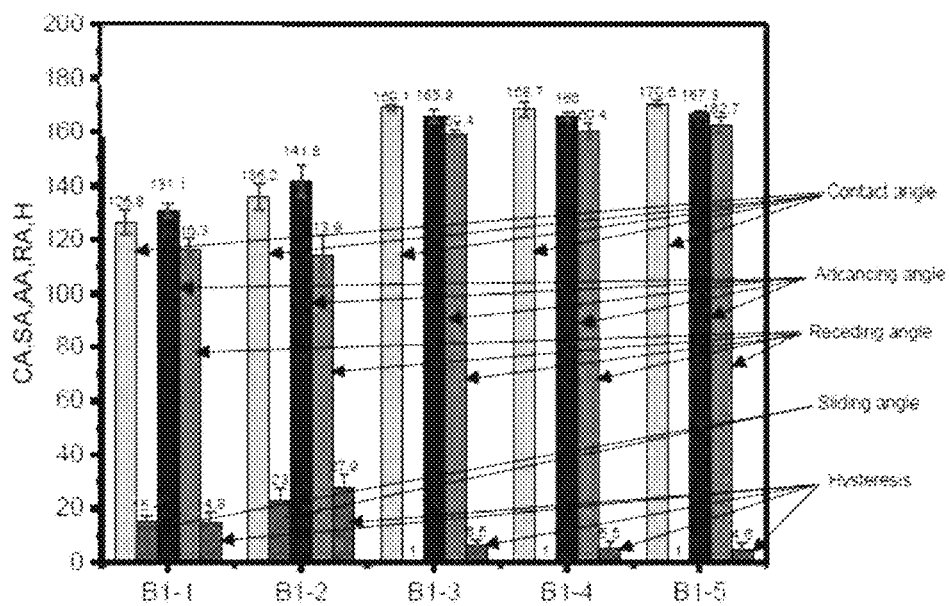
FIG. 19 represents average values of a contact angle (CA), a sliding angle (SA), an advancing angle (AA), a receding angle (RA), and a hysteresis (H) of a water droplet on a superhydrophobic coating that is formed by the suspension that includes 1.0 wt % of silica nanoparticles, relative to the total weight of the solution.

Although higher number of spray cycles can result in higher static water contact angle and lower sliding angle and hysteresis as evident from the FIG. 19, but more silica particles are deposited decreasing the transmittance of the surface. The effect of silica deposition on the transparency of such surfaces is discussed in the following sections.

Figure 20:
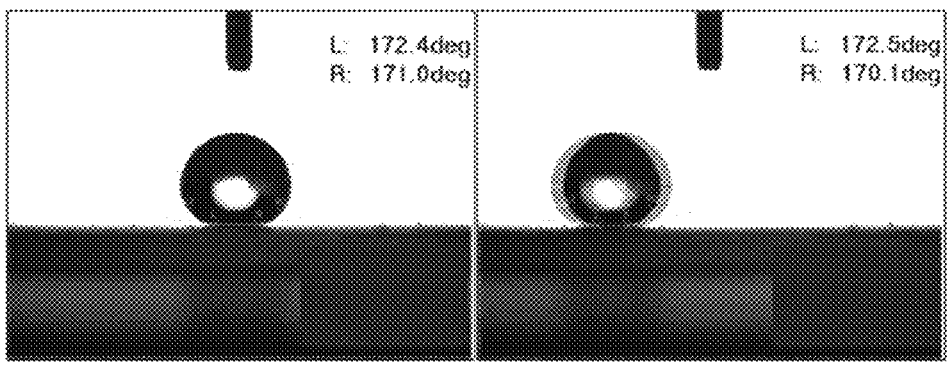
FIG. 20A represents a state of a water droplet on a superhydrophobic coating with three hydrophobic layers that include perfluoroalkyl-functionalized silica nanoparticles, wherein the substrate with the superhydrophobic coating is positioned at zero tilting angle.
FIG. 20B represents a state of a water droplet on a superhydrophobic coating with three hydrophobic layers that include perfluoroalkyl-functionalized silica nanoparticles, wherein the substrate with the superhydrophobic coating is positioned at 10 tilting angle.

FIG. 20 shows a water droplet starting to move at a very low tilting angle. A very low sliding angle of water droplet on sample B1-3 approximately 10 indicates that the water droplet on this surface is in Cassie-Baxter state.

Figure 21:
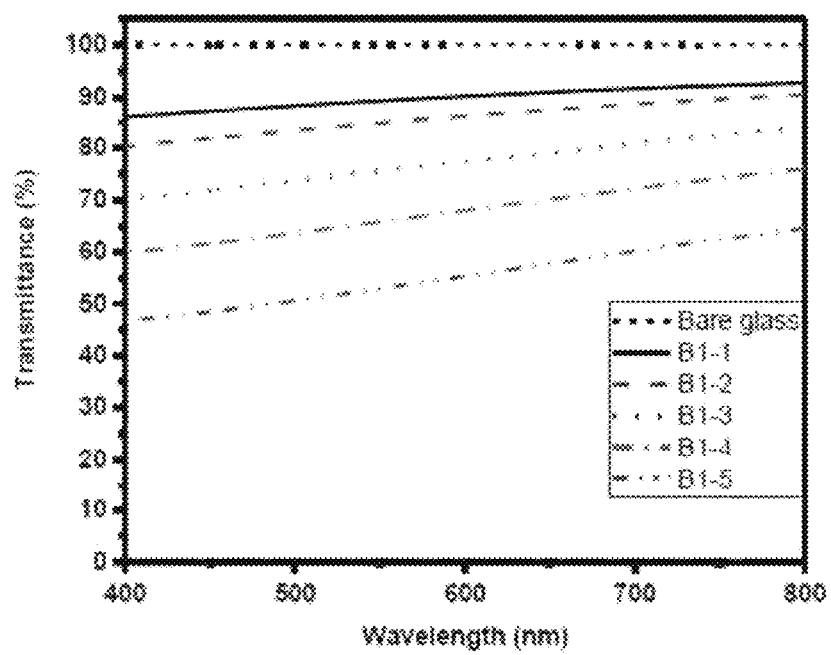
FIG. 21 represents transmittance spectra of the superhydrophobic coatings that include perfluoroalkyl-functionalized silica nanoparticles.
Figures 22A, 22B, 22C, 22D:
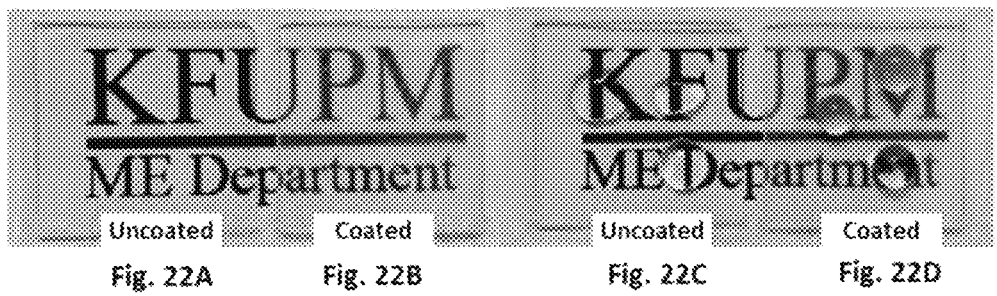
FIG. 22A is an image of a glass substrate.
FIG. 22B is an image of a superhydrophobic coating having perfluoroalkyl-functionalized silica nanoparticles.
FIG. 22C is an image of a water droplet on the glass substrate.
FIG. 22D is an image of a water droplet on the superhydrophobic coating.

FIG. 21, it is clear that sample B1-3 is be the best sample with preferable combinations of superhydrophobicity and transmittance to visible light. It has a CA of 169.1°, SA of 1° and hysteresis of 6.5. Furthermore, it shows more than 70% transmittance at a wavelength of 400 nm. With an increase of visible light wavelength its transmittance also increased correspondingly and almost reached up to 85% at the wavelength of 800 nm as showed in the FIG. 21. FIG. 22 shows visual appearance of the uncoated glass and coated glass (sample B1-3).

Figure 23:
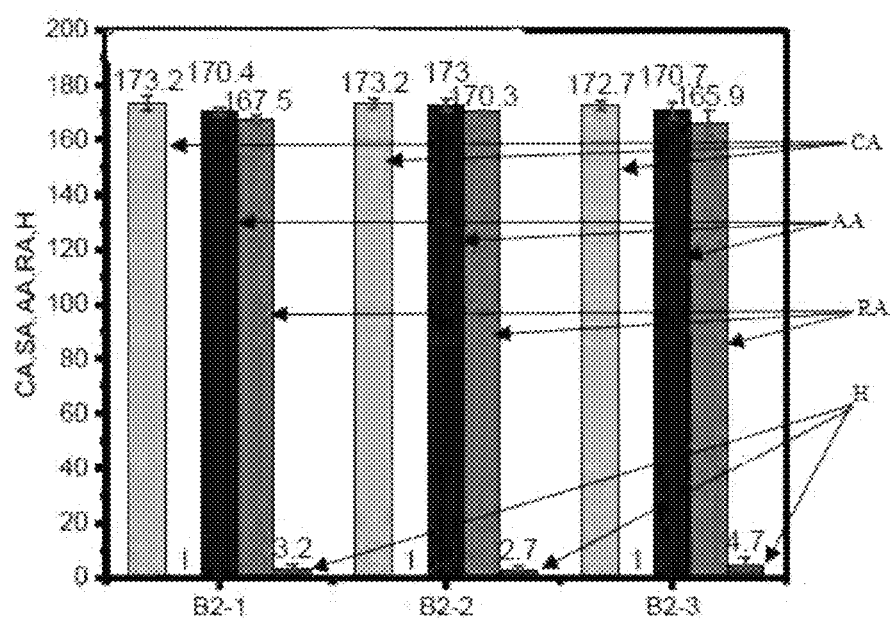
FIG. 23 represents average values of a contact angle (CA), a sliding angle (SA), an advancing angle (AA), a receding angle (RA), and a hysteresis (H) of a water droplet on a superhydrophobic coating that is formed by the suspension that includes 2.0 wt % of silica nanoparticles, relative to the total weight of the solution.

Table 7 and FIG. 23 shows that regardless of the number of cycles all samples sprayed with Sol B having 2.0 wt % silica nanoparticles result in superhydrophobic surface. Although Sol B with 2.0 wt % of silica nanoparticles sprayed only by one cycle (B2-1) can make the surface superhydrophobic, its transmittance is found to be far below that of B1-3.

TABLE 7

Contact angle, sliding angle, advancing angle, receding angle and hysteresis of the samples sprayed with solution B including 2 wt % silica Nanoparticles.

| Samples | CA | SA | AA | RA | H |
|---|---|---|---|---|---|
| B2-1 | 173.2 ± 2.8 | 1 ± 0 | 170.4 ± 1.8 | 167.5 ± 1.2 | 3.2 ± 1.9 |
| B2-2 | 173.2 ± 2.0 | 1 ± 0 | 173 ± 2.0 | 170.3 ± 0.3 | 2.7 ± 1.9 |
| B2-3 | 172.7 ± 1.7 | 1 ± 0 | 170.7 ± 3.1 | 165.9 ± 4.6 | 4.7 ± 2.9 |

Example 5—Superhydrophobic Surface Morphology

Figure 24A:
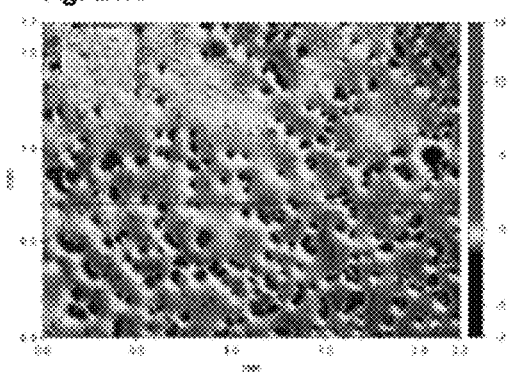
FIG. 24A is a 2D AFM micrograph of a surface of the superhydrophobic coating with one hydrophobic layer.
Figure 24B:
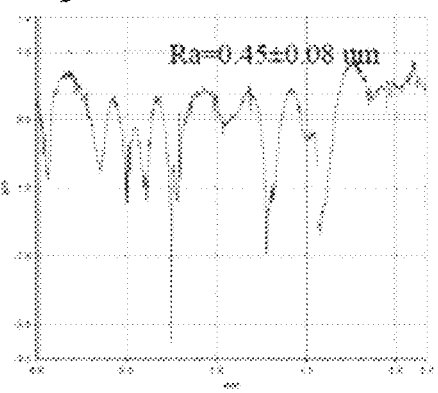
FIG. 24B is a line scan of the 2D AFM micrograph of a surface of the superhydrophobic coating with one hydrophobic layer.
Figure 24C:
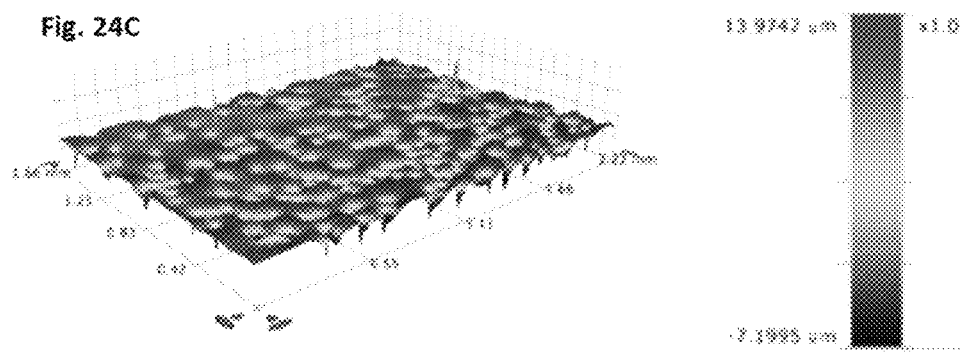
FIG. 24C is a 3D AFM micrograph of a surface of the superhydrophobic coating with one hydrophobic layer.
Figure 26A:
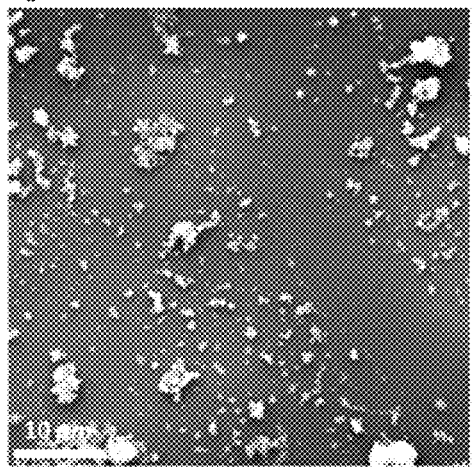
FIG. 26A is a SEM micrograph of a surface of the superhydrophobic coating with one hydrophobic layer at a low magnification.
Figure 26B:
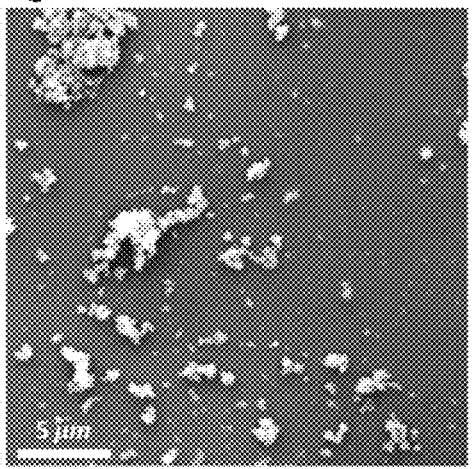
FIG. 26B is a SEM micrograph of a surface of the superhydrophobic coating with one hydrophobic layer at a medium magnification.
Figure 26C:
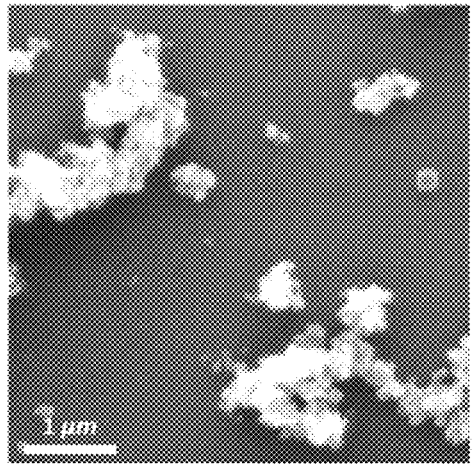
FIG. 26C is a SEM micrograph of a surface of the superhydrophobic coating with one hydrophobic layer at a high magnification.
Figure 26D:
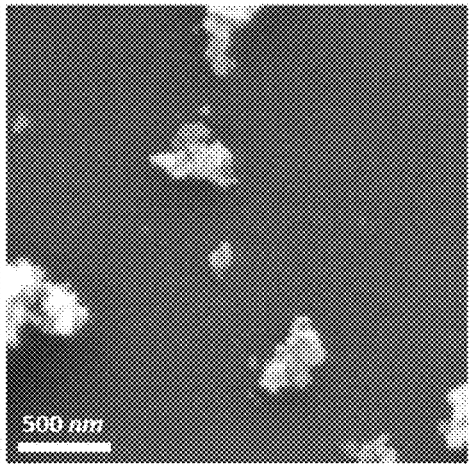
FIG. 26D is a SEM micrograph of a surface of the superhydrophobic coating with one hydrophobic layer at a very high magnification.
Figure 27A:
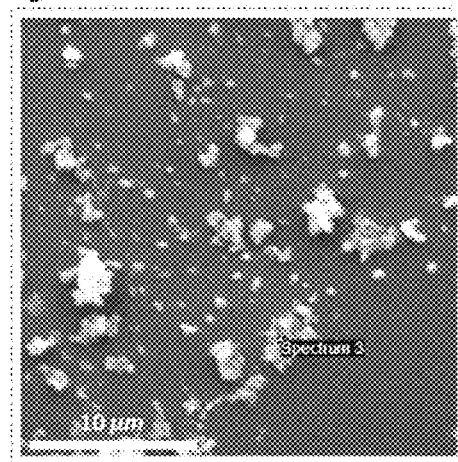
FIG. 27A is a SEM micrograph of a surface of the superhydrophobic coating with one hydrophobic layer.
Figure 27C:
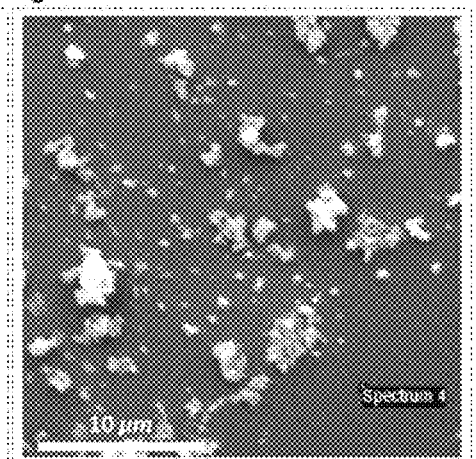
FIG. 27C is another SEM micrograph of a surface of the superhydrophobic coating with one hydrophobic layer.
Figure 27B:
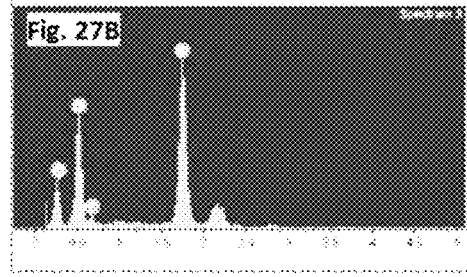
FIG. 27B is an EDS spectrum of the superhydrophobic coating with one hydrophobic layer, wherein the EDS spectrum is taken at the point "spectrum 3" of the surface.
Figure 27D:
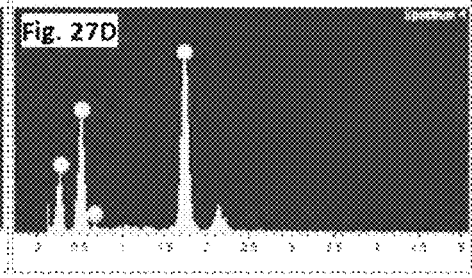
FIG. 27D is an EDS spectrum of the superhydrophobic coating with one hydrophobic layer, wherein the EDS spectrum is taken at the point "spectrum 4" of the surface.
Figure 28A:
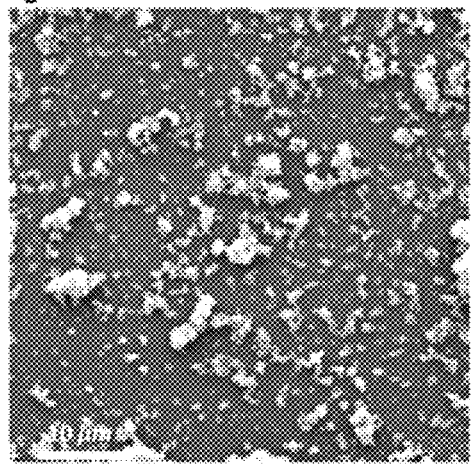
FIG. 28A is a SEM micrograph of a surface of the superhydrophobic coating with three hydrophobic layers at a low magnification.
Figure 28B:
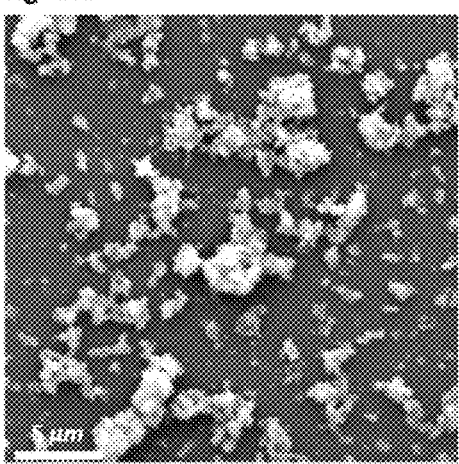
FIG. 28B is a SEM micrograph of a surface of the superhydrophobic coating with three hydrophobic layers at a medium magnification.
Figure 28C:
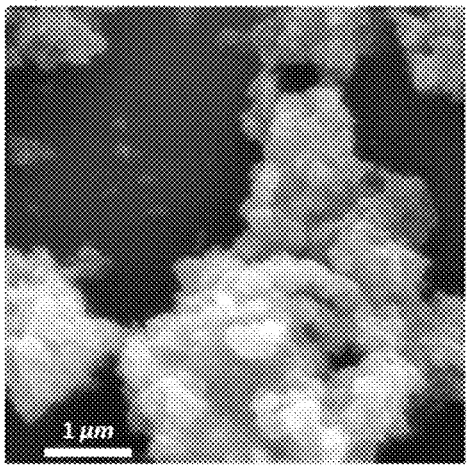
FIG. 28C is a SEM micrograph of a surface of the superhydrophobic coating with three hydrophobic layers at a high magnification.
Figure 28D:
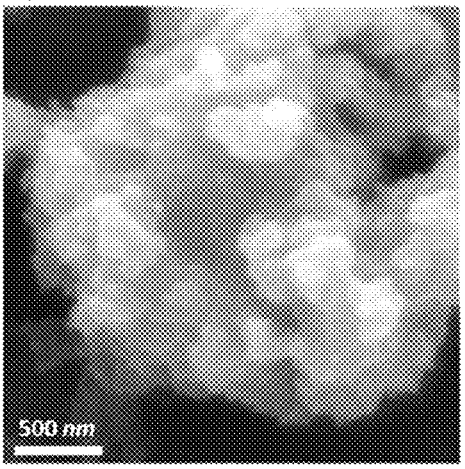
FIG. 28D is a SEM micrograph of a surface of the superhydrophobic coating with three hydrophobic layers at a very high magnification.
Figure 29A:
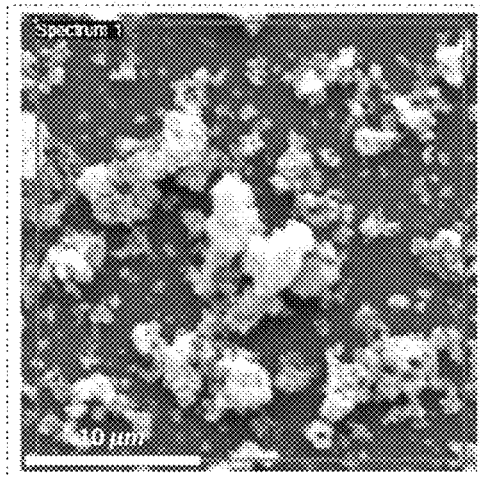
FIG. 29A is a SEM micrograph of a surface of the superhydrophobic coating with three hydrophobic layers.
Figure 29C:
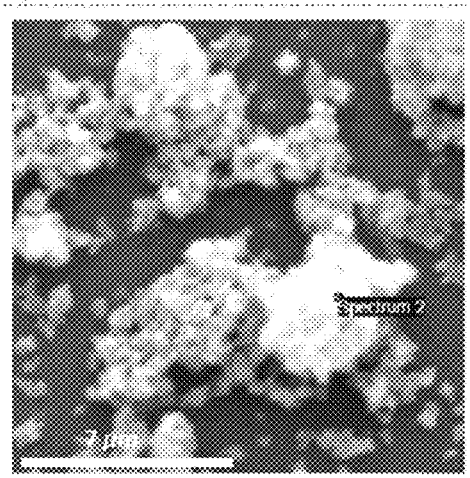
FIG. 29C is another SEM micrograph of a surface of the superhydrophobic coating with three hydrophobic layers.
Figure 29B:
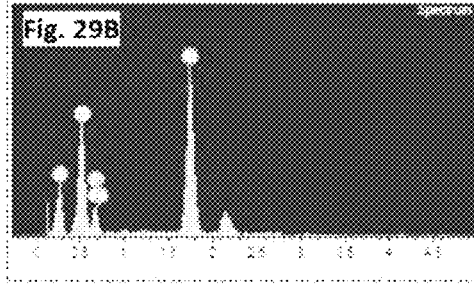
FIG. 29B is an EDS spectrum of the superhydrophobic coating with three hydrophobic layers, wherein the EDS spectrum is taken at the point "spectrum 1" of the surface.
Figure 29D:
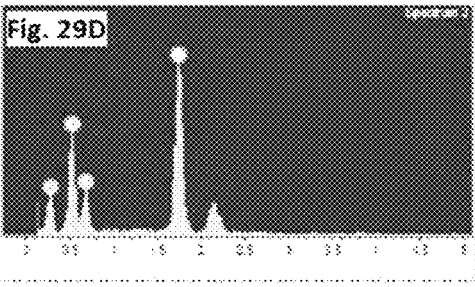
FIG. 29D is an EDS spectrum of the superhydrophobic coating with three hydrophobic layers, wherein the EDS spectrum is taken at the point "spectrum 2" of the surface.

Roughness of the surface was measured by a 3D optical profilometer, wherein a 2D surface topography, a 3D surface topography, and a line scan is shown for the sample B1-1 in FIG. 24, and for the sample B1-3 in FIG. 25. The AFM results indicate that the sample B1-1 have a higher roughness than the sample B1-3. For the sample B1-1, although deposition of Sol B is only one cycle, it has higher roughness than the sample B1-3. By observing the corresponding line scan of B1-1 it is easy to understand that the surface roughness is mainly due to the rough deposition of the first layer of Sol A by manual spray coating process. The first layer creates the roughness at micro level giving rise to roughness of the surface when it was measured on the area of 1.7×2.2 mm. This is clearer when the line scans of two samples are compared. On sample B1-3 line scan waviness and small spikes deviated from waviness, creating submicron and nano-roughness more uniformly are observed. Although the roughness of the surface can be measured on large area by 3D optical profilometer, but it may not give the actual roughness value of the surface at micro and nano level like Atomic Force Microscopy. Another reason for this observation is that the optical profilometer collects the surface information by reflected light. Hence, if light passes through a transparent surface, the results may be misleading. Although in our case the samples used to measure the surface roughness were coated with gold to minimize the error between readings from optical profilometer and actual roughness. Although sample B1-1 has higher roughness, it lacks the dual scale roughness structure, which is an important factor for the extreme water-repellency. It is clear from the line scan of these two samples that sample B1-3 has the dual scale combination of nano and micro structure which is preferred for non-wetting characteristics.

SEM, XPS, and Raman Analyses

FIG. 26 and FIG. 28 show SEM micrographs of sample B1-1 and B1-3 at different magnifications, respectively.

The SEM images of sample B1-1 from different magnifications, show clearly that some of the area is not fully covered by the silica nanoparticles, for this reason, the surface roughness created by the particles is not enough to create air pockets for resulting hydrophobicity. It is clear from the CA result that hydrophobic surface on the sample B1-1 resulted from the low surface energy rather than the roughness since the sample B0-1 (sprayed with 0 wt %) having hydrophobic surface and CA result almost near to the sample B1-1. According to the chemicals (such as PFOTS) used in the experiment and from literature statement that closest hexagonal packing of $CF_3$ groups give the lowest surface energy of the materials. Once the surface of a sample was sprayed with PFOTS, the surface revealed a surface energy as low as 6 $mJ/m^2$. See A. Venkateswara Rao, S. S. Latthe, D. Y. Nadargi, H. I-Iirashima, and V. Ganesan, "Preparation of MTMS based transparent superhydrophobic silica films by sol-gel method," *J. Colloid Interface Sci.*, vol. 332, no. 2, pp. 484-490, 2009; M. Psarski, J. Marczak, G. Celichowski, G. B. Sobieraj, K. Gumowski, F. Zhou, W. Liu, and V. sp oo, "Hydrophobization of epoxy nanocomposite surface with 1,1,2,2-perfluorooctyltrichlorosilane for superhydrophobic properties," *Cent. Eur. J. Phys.*, vol. 10, no. 5, pp. 1197-1201, 2012; Takashi Nishino, Masashi Meguro, Katsuhiko Nakamae, A. Motonori Matsushita, and Y. Ucda, "The Lowest Surface Frcc Energy Based on —CF3 Alignment," 1999; E. F. Hare, E. G. Shafrin, and W. A. Zisman, "Properties of films of adsorbed fluorinated acids," *J. Phys. Chem.*, vol. 58, no. 3, pp. 236-239, 1954; and E. Lindner and E. Arias, "Surface free energy characteristics of polyfluorinated silane films," *Langmuir*, vol. 8, no. 4, pp. 1195-1198, April 1992.

When the SEM image of sample B1-1 and B1-3 are compared, it is observed that the surface of the sample B1-3 is better covered by the silica nanoparticles; in addition to that the agglomeration of silica particles is also observed. Agglomeration of the silica particles at micron or submicron level can be advantageous in creating micro and nano-roughness structure. See B. Bhushan, Y. C. Jung, and K. Koch, "Micro-, nano- and hierarchical structures for superhydrophobicity, self-cleaning and low adhesion," *Philos. Trans. R. Soc. London A Math. Phys. Eng. Sci.*, vol. 367, no. 1894, 2009; D. Byun, J. Hong, and Saputra, "Wetting Characteristics of Insect Wing Surfaces," *J. Bionic Eng.*, vol. 6, no. 1, pp. 63-70, March 2009; and Y. Yoon, D. Kim, and J.-B. Lee, "Hierarchical micro/nano structures for superhydrophobic surfaces and super-lyophobic surface against liquid metal," *Micro Nano Syst. Lett.*, vol. 2, no. 1, p. 3, December 2014.

FIG. 27 and FIG. 29 are EDS elemental analysis of samples B1-1 and B1-3, respectively. EDS results from both samples did not reveal any peaks corresponding to Cl, indicating that hydrolyzation and condensation of PFOTS took place completely. First —Cl replaced by the —OH groups by hydrolyzation reaction followed by the condensation reaction between two Si—OH groups to for siloxane (Si—O—Si) network. Presence of Fe peak in EDS spectrum may be due to 99.5% trace metals basis of silica nanoparticles used.

The chemical composition and surface atomic concentration of sample B1-3 was further characterized by XPS, as shown in FIG. 30. The C (C1s 284 eV, CKLL 982 eV) and O1s (532 eV) peaks can be seen clearly in the spectrum. Si (Si2p 102 eV and Si2s 153 eV) and F (F1s 688 eV and FKLL 835 eV) signals, characteristic of covalently bonded Si and F, was detected. High-resolution XPS provides additional insight into the chemical composition of the film further and confirming the presence of $CF_2$ and $CF_3$ groups. See H. Zhang, Y. Ma, J. Tan, X. Fan, Y. Liu, J. Gu, B. Zhang, H. Zhang, and Q. Zhang, "Robust, self-healing, superhydrophobic coatings highlighted by a novel branched thiol-ene fluorinated siloxane nanocomposites," Compos. Sci. Technol., vol. 137, pp. 78-86, 2016. Missing of C12p (200 eV) peak from the spectra indicating that the Cl atoms on the PFOTS completely replaced by OH groups and via condensation reaction connected to the silica particles as well as first layer and further confirming the conclusion from the EDS result.

Figure 31:
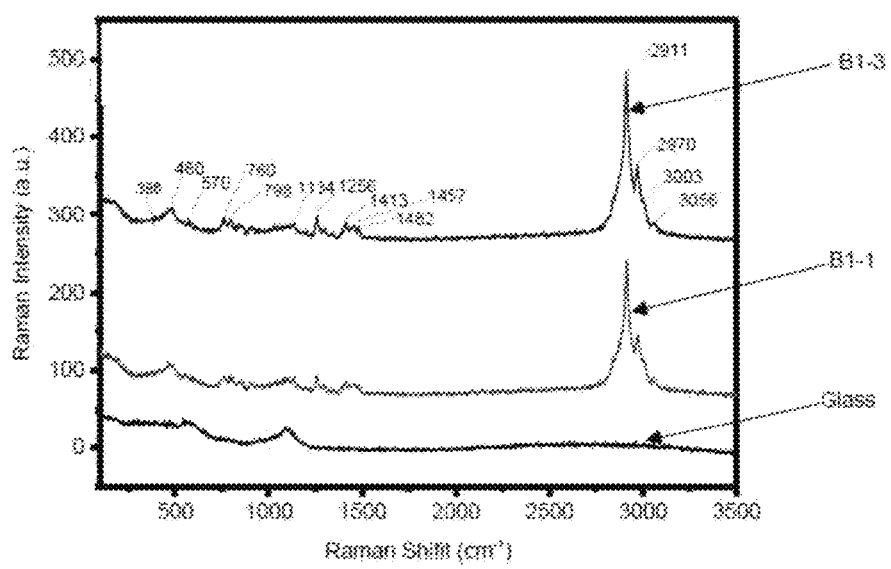
FIG. 31 represents Raman spectra of the substrate and the superhydrophobic coatings.

Selected sample B1-1 and B1-3 were further characterized by Raman Spectroscopy, FIG. 31 shows the labeled peak positions and Table 8 provides summarized Raman bands assignment of corresponding peaks.

TABLE 8

Raman bands assignment

| Raman bands (cm−1) | Assignment |
| --- | --- |
| 3056 | epoxy group CH stretching |
| 3003 | epoxy group CH stretching |
| 2970 | Anti-symmetric stretching vibrations of $CH_3$ |
| 2908 | Anti-symmetric stretching vibrations of $CH_3$ |
| 1482 | $CH_3\ \delta_s$ |
| 1457 | $CH_3\ \delta_s$ |
| 1413 | epoxy group |
| 1256 | epoxy ring breathing |
| 1131 | epoxy group |
| 570 | $CF_3$ symmetric deformation |
| 480 | Si—O—Si |
| 356 | $CF_2$ twisting |

See K. S. S. Kumar, V. Kumar, and C. P. R. Nair, "Bulk superhydrophobic materials: a facile and efficient approach to access superhydrophobicity by silane and urethane chemistries," J. Mater. Chem. A, vol. 2, no. 37, p. 15502, July 2014; D. Bersani, P. Lottici, M. Casalboni, and P. Prosposito, "Structural changes induced by the catalyst in hybrid sol-gel films: a micro-Raman investigation," 2001; and J. Mihály, S. Sterkel, H. M. Ortner, L. Kocsis, L. Hajba, É. Furdyga, and J. Mink, "FTIR and FT-Raman Spectroscopic Study on Polymer Based High Pressure Digestion Vessels," Croat. Chem. Acta, vol. 79, no. 3, pp. 497-501, 2006.

Both sample B1-1 and B1-3 having similar Raman spectra with only difference in peak intensity. For both samples, the presence of $CF_2$, $CF_3$ peaks indicated that the surface functionalization of the silica nanoparticles were successfully taken place by the PFOTS, other peaks contributed from the first layer which is formed from hydrolysis and condensation of MTMS and GLYMO. There is almost no small difference between B1-1 and B1-3 spectra peaks position, as B1-1 and B1-3 samples are both coated with second layer Sol B, only with difference in spray cycles.

Both B1-1 and B1-3 have substantially the same surface chemistry, however they revealed different wettability to the water droplets. B1-3 showed less wettability than the B1-1. This difference in wettability indicates the importance of micro- and nano-surface roughness to change the characteristics of a surface from hydrophobic to superhydrophobic. See S. Herminghaus, "Roughness-induced non-wetting," Europhys. Lett., vol. 79, no. 5, p. 59901, September 2007; M. Nosonovsky, B. Bhushan, A. A. V, and A, "Roughness-induced superhydrophobicity: a way to design non-adhesive surfaces," J. Phys. Condens. Matter, vol. 20, no. 22, p. 225009, June 2008; and Q. Zheng and C. Lü, "Size Effects of Surface Roughness to Superhydrophobicity," Procedia IUTAM, vol. 10, pp. 462-475, 2014. As shown in FIG. 28, SEM images B1-3 sample surface deposited with more silica particles, and surface thus is provided with enough roughness that necessary to create superhydrophobic surface. Also, agglomeration of the silica nanoparticles at some extent is favorable for superhydrophobicity since it can provide surface with hierarchical structure of micro-nano roughness.

Example 6—Self-Cleaning Properties

FIG. 32 illustrates self-cleaning mechanism of the superhydrophobic surfaces. When a surface is superhydrophobic, it cannot easily become wet by water. When water droplets hit the superhydrophobic surface, they will bounce away and/or start rolling off of the surface. During the rolling, water droplets can collect certain amounts of dust particles.

FIG. 33 shows how this mechanism works on the surface of B1-3 sample. It compares the self-cleaning ability of both coated and bare glass when tilted around with the angle of 10°. The adjacent surfaces are covered with a similar amount of sand particles. The droplets of colored water are shown to roll off the coated surface taking away the dust, while those on the bare surface stuck to it. It is worth mentioning that only 6 droplets of water were sufficient to remove all the dust on the 25×25 mm area of coated glass surface.

As water droplet spread on the hydrophilic surface, not like superhydrophobic surface, dust particles not removed by water droplets. The mud formed, from dust particles in humid air condition, on the surface of glass more strongly adhered to surface. Once mud dried, there is formation of a thin mud solution film between dust particles and glass surface and alters the surface characteristics. See G. Hassan, B. S. Yilbas, S. A. M. Said, N. Al-Aqeeli, and A. Matin, "Chemo-Mechanical Characteristics of Mud Formed from Environmental Dust Particles in Humid Ambient Air.," Sci. Rep., vol. 6, p. 30253, July 2016.

Example 7—Thermal Stability and Effect of Annealing

Sample B1-3 revealed the preferred properties in terms of superhydrophobicity and transmittance, was selected for testing the thermal stability of the superhydrophobic coating. To do so, the sample was kept in the furnace for 2 hours at 300° C., 350° C. and 400° C., then the different contact angles and hysteresis were measured to study the thermal stability of coatings on glass substrate. The results that are listed in Table 13 revealed that annealing at temperatures higher than 300° C. for two hours drastically reduces the contact angle.

TABLE 13

Contact angle, sliding angle, advancing angle, receding angle and hysteresis of the sample B1-3 annealed at different temperature.

| Temperature | CA | SA | AA(L) | RA(R) | Hysteresis(H) |
|---|---|---|---|---|---|
| 0° C. | 169.1 ± 1.0 | 1 ± 0 | 165.9 ± 2.5 | 159.4 ± 1.4 | 6.5 ± 1.8 |
| 300° C. | 167.1 ± 1.0 | 1 ± 0 | 166.2 ± 2.7 | 159.3 ± 1.6 | 6.9 ± 2.1 |
| 350° C. | 137.5 ± 3.8 | NA | NA | NA | NA |
| 400° C. | 72.1 ± 6.4 | NA | NA | NA | NA |

FIG. 34 shows that annealing improved the overall transmittance of the surface by about 8%. Similar results were reported by other researchers. See L. Xu, D. Zhu, X. Lu, and Q. Lu, "Transparent, Thermally and Mechanically Stable Superhydrophobic Coating Prepared by Electrochemical Template strategy," *J. Mater. Chem. A*, 2015; M. Alam and D. Cameron, "Optical and electrical properties of transparent conductive ITO thin films deposited by sol-gel process," *Thin Solid Films*, vol. 377, pp. 455-459, 2000; and S.-S. Kim, S.-Y. Choi, C.-G. Park, and H.-W. Jin, "Transparent conductive ITO thin films through the sol-gel process using metal salts," *Thin Solid Films*, vol. 347, no. 1, pp. 155-160, 1999. Budunoglu et al reported that optical transparency can be further improved when some films are calcinated under an appropriate temperature resulting in even higher optical transmission than the bare glass slide because of the reduced back reflection. Superhydrophobic surface can be oxidized at elevated temperature resulting to loss of hydrophobicity as it is evident from the results of our study obtained at 400° C.

Figure 35:
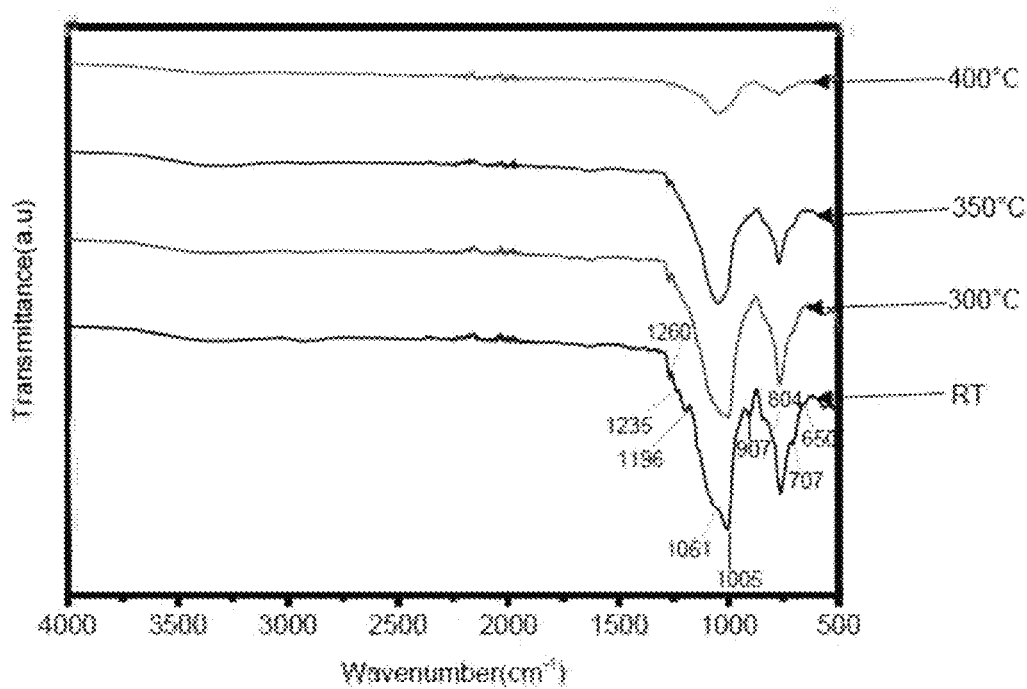
FIG. 35 represents FTIR spectra of the superhydrophobic coating after annealing at various temperatures.

Degradation of the superhydrophobic surface is mainly due to a decomposition and oxidation of surface chemistry rather than to a change in the surface roughness. See Y. Xiu, D. W. Hess, and C. P. Wong, "UV and thermally stable superhydrophobic coatings from sol-gel processing," *J. Colloid Interface Sci.*, vol. 326, no. 2, pp. 465-470, 2008. FTIR analysis of the surface before and after heat treatment at different temperatures indicated that hydrocarbon absorptions were absent. FIG. 35 illustrates FTIR bands peak position for room temperature (RT) and heat-treated samples.

The FTIR spectroscopy bands occurred at 1005 cm$^{-1}$ and 1061 cm$^{-1}$ corresponding to Si—O—Si stretching. See L. M. Johnson, L. Gao, C. Shields I V, M. Smith, K. Efimenko, K. Cushing, J. Genzer, and G. P. López, "Elastomeric microparticles for acoustic mediated bioseparations," *J. Nanobiotechnology*, vol. 11, no. 1, p. 22, June 2013; and H. Wang, J. Fang, T. Cheng, J. Ding, L. Qu, L. Dai, X. Wang, and T. Lin, "One-step coating of fluoro-containing silicananoparticles for universal generation of surface superhydrophobicity," *Chem. Commun.*, vol. 28, no. 7, pp. 877-879, 2008. Two tiny peaks at 1235 cm$^{-1}$ and 1196 cm$^{-1}$ superimposed between 1061 and 1260 cm$^{-1}$ on the left shoulder of the Si—O—Si peak at 1061 cm$^{-1}$ are due to the stretching vibration of C—F bonds anticipated, which is the sign of the fluorination of the silica nanoparticles by the PFOTS molecules. See K. Nozawa, H. Gailhanou, L. Raison, P. Panizza, H. Ushiki, E. Sellier, J. P. Delville, and M. H. Delville, "Smart Control of Monodisperse Sto 1 ber Silica Particles: Effect of Reactant Addition Rate on Growth Process," *Langmuir*, vol. 21, pp. 1516-1523, 2005; and P. Wang, J. Liu, W. Chang, X. Fan, C. Li, and Y. Shi, "A facile cost-effective method for preparing robust self-cleaning transparent superhydrophobic coating," *Appl. Phys. A*, 2016. However, these two tiny peaks become less significant on the 300° C. line and totally disappear on the 350° C. and 400° C. lines. Without the presence of low surface energy functional groups such as $CF_2$ and $CF_3$, the surface water contact angle decreased to 137.5° for the sample heat treated at 350° C. and to 72.1° for the sample heat treated at 400° C. Peak around 907 cm$^{-1}$ corresponding to C—H bonds arising from PFOTS molecules is not present on the lines of heat treated samples. See S. S. Latthe, H. Imai, V. Ganesan, and A. V. Rao, "Superhydrophobic silica films by sol-gel co-precursor method," *Appl. Surf Sci.*, vol. 256, no. 1, pp. 217-222, 2009.

The existence of C—F bonds in the form of $CF_2$ and $CF_3$ are also located at 650 and 707 cm$^{-1}$. See A. Hozumi and O. Takai, "Effect of hydrolysis groups in fluoro-alkyl silanes on water repellency of transparent two-layer hard-coatings," *Appl. Surf Sci.*, vol. 103, no. 4, pp. 431-441, 1996; and H. Ni, X. Wang, W. Zhang, X. Wang, and Z. Shen, "Stable hydrophobic surfaces created by self-assembly of poly(methyl methacrylate) end-capped with 2-perfluorooctylethyl methacrylate units," *Surf Sci.*, vol. 601, no. 17, pp. 3632-3639, 2007. These functional groups, which are responsible for lowering the surface energy, become less significant on the 300° C. and totally disappear at higher temperatures. The absence of these peaks on the samples heat-treated at 350° C. and 400° C. result in drastic reduction of the water contact angles and in increasing the sliding angle and hysteresis. The FTIR spectroscopy bands at 1260 cm$^{-1}$ ($CH_3$ bending) and 804 cm$^{-1}$ ($CH_3$ rocking) which are present only on the RT, 300° C. and 350° C. lines indicate that 400° C. heat treatment has totally degraded the superhydrophobic surface. Although $CF_2$ and $CF_3$ peaks were absent on the 350° C. lines, the presence of $CH_3$ peaks still give this sample some hydrophobic characteristics as reported earlier. As stated in the literature review, $CF_2$ and $CF_3$ groups have lowest surface energy compared to the $CH_3$ and other functional ending groups. This explains why the sample heat treated at 350° C. is still hydrophobic when surface maintains proper roughness. This is a further indication that the combination of surface roughness and surface chemistry are vital for the fabrication of the superhydrophobic surfaces. All the FTIR bands peaks position and assigned functional groups are listed in the Table 9.

TABLE 9

Fourier transform infrared bands assignment.

| FTIR bands (cm$^{-1}$) | Assignment |
|---|---|
| 1235 | stretching vibration of C—F bonds |
| 1196 | stretching vibration of C—F bonds |
| 1260 | $CH_3$ bending |
| 803 | $CH_3$ rocking |
| 1005 | Si—O—Si stretching |
| 1061 | Si—O—Si stretching |
| 907 | C—H bonds (arising from PFOTS molecules) |
| 650 | $CF_2$ and $CF_3$ |
| 707 | $CF_2$ and $CF_3$ |

Example 8—Resistance to Ultraviolet Radiation

After the long period of UV irradiation (10 hours at UV lamp intensity of 2500 W/m$^2$ and 2 hours at UV lamp intensity of 30000 W/m$^2$), test sample contact angle details are measured and are reported in compare to C—C bond (bond energy of 346 kJ/mol). These results are listed in Table 10.

According to the literature, long-term daily mean values of sunshine duration and Global Solar Radiation (GSR) is about 9.2 hours and 5123 W/m² per day respectively in the region of Riyadh, Saudi Arabia (Lat. is 24.57°, Lon. is 46.72°, and Alt. is 564 m). See M. Mohandes and S. Rehman, "Global Solar Radiation Maps of Saudi Arabia," *J. Energy Power Eng.*, vol. 4, no. 1237, pp. 1934-8975, 2010. Approximately 5% of solar terrestrial radiation is Ultra-Violet Radiation (UVR) (approximately 256 W/m² per day). In our study, the highest intensity of the UV lamp 100 times more than the actual UV light intensity in the Riyadh region. The results show that the average values for the different types of angles are almost identical before and after UV irradiation. This is an indication of high UV resistance of the produced superhydophobic surface. This is mainly due to the presence of Si—O—Si (Si—O bond energy of 452 kJ/mol) and C—F (bond energy of 485 kJ/mol) high chemical energy bonding which require very high energy or very long exposure time to degrade compare to C—C bond (bond energy of 346 kJ/mol).

TABLE 10

Contact angle, sliding angle, advancing angle, receding angle and hysteresis of sample B1-3 before and after ultraviolet irradiation test.

| UV testing | CA | SA | Advancing contact angle (AA) | Receding contact angle (RA) | Hysteresis (H) |
|---|---|---|---|---|---|
| Before | 169.1 ± 1.0 | 140 | 165.9 ± 2.5 | 159.4 ± 1.4 | 6.5 ± 1.8 |
| After | 169.0 ± 1.2 | 140 | 166.0 ± 2.2 | 159.1 ± 1.3 | 6.9 ± 1.9 |

Figures 36A, 36B, 36C, 36D:
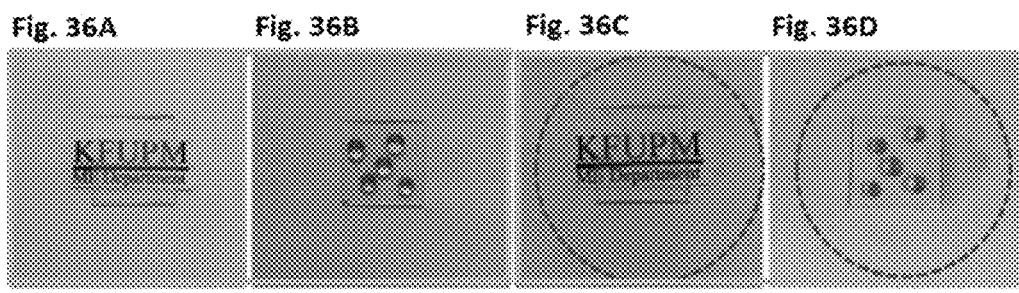
FIG. 36A is an image of the substrate with the superhydrophobic coating before exposing to UV radiation.
FIG. 36B is an image of the state of a water droplet on the substrate with the superhydrophobic coating before exposing to UV radiation.
FIG. 36C is an image of the substrate with the superhydrophobic coating after exposing to UV radiation.
FIG. 36D is an image of the state of a water droplet on the substrate with the superhydrophobic coating after exposing to UV radiation.

From FIG. 36, it can be clearly observed that the A4 white paper placed under the sample (dashed circle line area) changed to yellowish color after UV irradiation test. The dashed circle area is approximately the spot size of UV light when irradiated on the surface of sample. It is also clear from FIG. 36, that not only has the surface retained its hydrophobicity, it has also maintained its transparency.

For the silica film, only small side groups (such as PFOTS molecules, connected to silica surface by condensation reaction) exist on the surface; these moieties are more UV stable than are polymers because negligible impurities and less UV-fragile defects exist on the silica surface. Thus, the silica film exhibits better UV stability than do organic polymers. In addition, the silica main chain is comprised of Si—O bonds, which have higher bond strength and thus better UV stability than organic polymer materials. The above proven UV irradiation resistance enables the application of the fabricated superhydrophobic surface outdoor field environment.

Basically, organic polymers with reactive (e.g., double bonds) or low energy (e.g., tertiary hydrogen) structures in the polymer main chain, are vulnerable to UV irradiation. When impurities (i.e., catalyst) and UV absorbing groups are present, the polymer can undergo a photo-oxidation process to form carbonyl or hydroxyl groups on the surface and thus degrade (unzip) into smaller chains.

Figure 37:
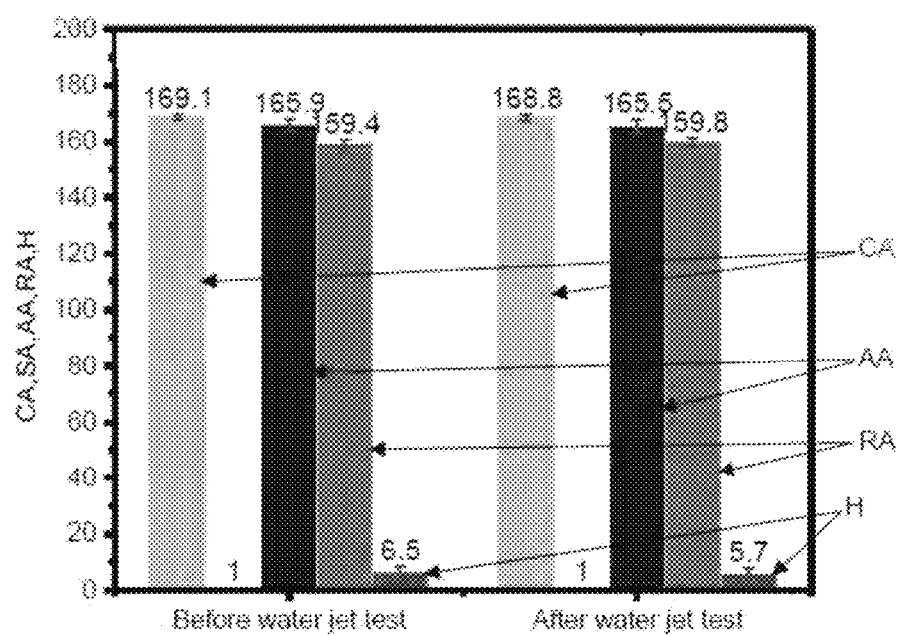
FIG. 37 represents average values of a contact angle (CA), a sliding angle (SA), an advancing angle (AA), a receding angle (RA), and a hysteresis (H) of a water droplet on the superhydrophobic coating before and after the water jet test.

Example 9—Superhydrophobic Surface Resistance to Water Jet, Abrasion, and Sand Blasting Table 11 and FIG. 37 show the measured angles before and after water jet that characterize the hydrophobicity of the surface. A comparison of the contact angle details before and after one hour of water jet testing is also shown in both the table and the graph of FIG. 37. It is evident that, the average values of static water contact angle, sliding angle and hysteresis did not experience any significant changes. This indicates that the intense water jet test did not damage the hydrophobicity of the surface by either removing silica nanoparticles on the surface or degrading the functional —$CF_3$ groups or other low surface energy functional groups. Without degradation of the surface chemistry and roughness of superhydrophobic surface, it can maintain same superhydrophobic properties after the water jet test. Minute change in the angles after test can be ascribed to the normal experimental measurement error.

TABLE 11

Contact angle details before and after water jet test.

| Water jet test | CA | SA | AA (L) | RA(R) | Hysteresis(H) |
|---|---|---|---|---|---|
| Before | 169.1 ± 1.0 | 1 ± 0 | 165.9 ± 2.5 | 159.4 ± 1.4 | 6.5 ± 1.8 |
| After | 168.8 ± 1.3 | 1 ± 0 | 165.5 ± 2.7 | 159.8 ± 1.6 | 5.7 ± 2.3 |

Figures 38A, 38B:
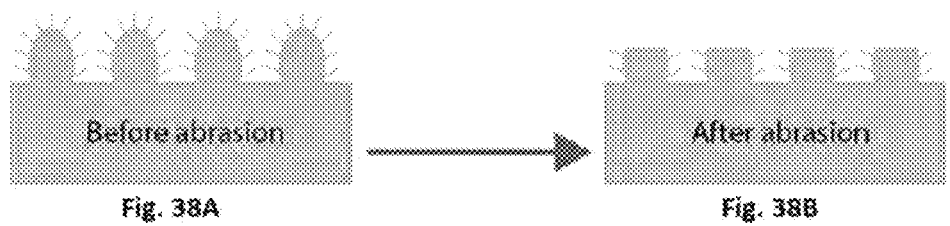
FIG. 38A illustrates the state of the surface of the superhydrophobic coating before abrasion.
FIG. 38B illustrates the state of the surface of the superhydrophobic coating after abrasion.
Figure 39:
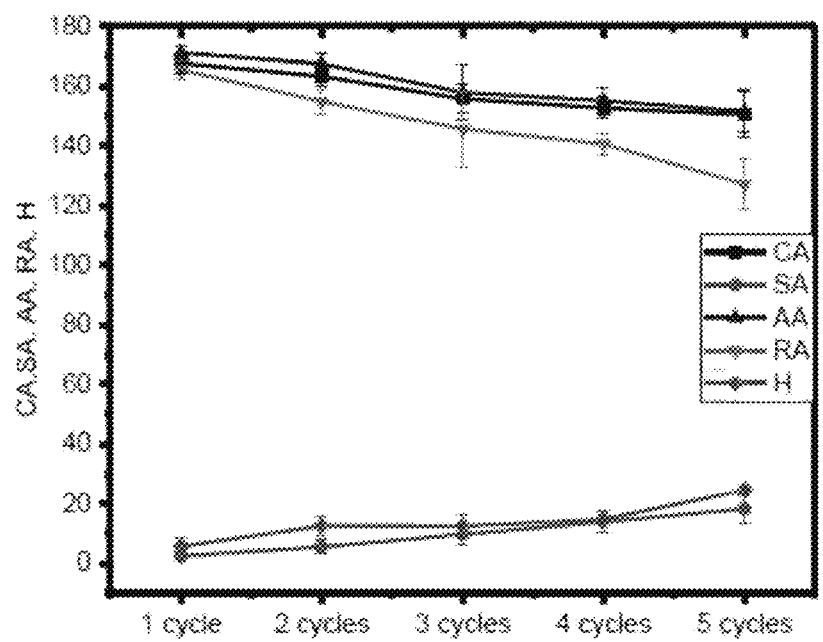
FIG. 39 represents average values of a contact angle (CA), a sliding angle (SA), an advancing angle (AA), a receding angle (RA), and a hysteresis (H) of a water droplet on the superhydrophobic coating at various numbers of hydrophobic layers.

The results in Table 12 and FIG. 39 describe the effect of abrasion on the hydrophobic properties of the fabricated surface after each cycle. It is clear that degradation of these properties becomes significant after few cycles. The abrasive surface of the sand paper has started to affect the roughness of the produced surface after the 1st cycle by flattening or removing its asperities as illustrated in FIG. 38. It is worth mentioning that the static contact angle, CA, remains above 150° even after 5 cycles, but RA and H have been chiefly affected.

TABLE 12

Change in contact angles with number of cycles.

| No. of cycles | CA | SA | Advancing angle (AA) | Receding Angle (Ra) | Hysteresis (H) |
|---|---|---|---|---|---|
| 1 cycle | 167.6 ± 3.5 | 2.4 ± 1.1 | 171 ± 2.2 | 165.4 ± 2.9 | 5.6 ± 2.6 |
| 2 cycles | 163.3 ± 3.0 | 5.4 ± 2.5 | 167.4 ± 3.2 | 154.9 ± 4.1 | 12.5 ± 3.3 |

TABLE 12-continued

Change in contact angles with number of cycles.

| No. of cycles | CA | SA | Advancing angle (AA) | Receding Angle (Ra) | Hysteresis (H) |
|---|---|---|---|---|---|
| 3 cycles | 155.8 ± 4.9 | 9.6 ± 3.4 | 157.9 ± 9.4 | 145.5 ± 12.9 | 12.4 ± 4.0 |
| 4 cycles | 152.7 ± 3.6 | 13.8 ± 3.4 | 155.1 ± 4.1 | 140.5 ± 3.7 | 14.6 ± 1.6 |
| 5 cycles | 150.5 ± 8 | 18.2 ± 5.1 | 151.6 ± 7.0 | 127.0 ± 8.4 | 24.6 ± 1.7 |

Figures 40A, 40B:
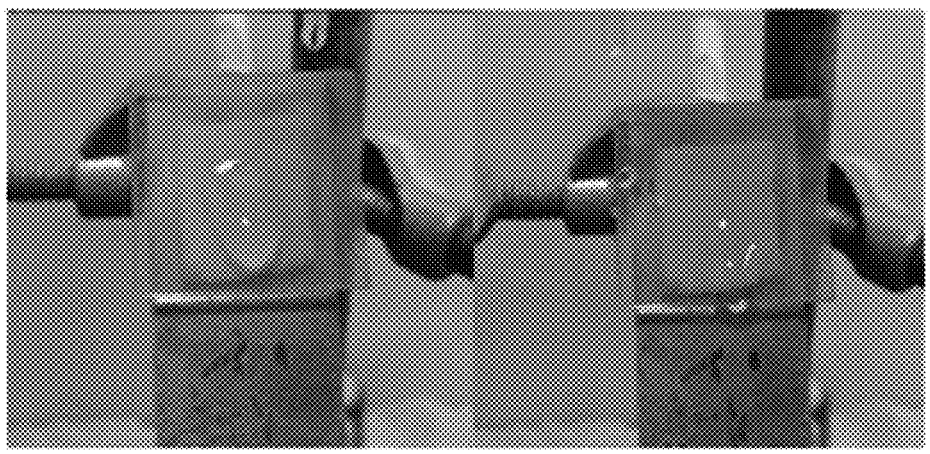
FIG. 40A is an image that represents the state of a water droplet on the center of the superhydrophobic coating after the sand blast test.
FIG. 40B is an image that represents the state of a water droplet on the edge of the superhydrophobic coating after the sand blast test.

Sand blasting test is one of the simulated tests that have been conducted to evaluate the robustness of the fabricated superhydophobic surface. This test can simulate the surface encountering outdoor aggressive weather conditions such as strong winds associated with sand storms, as is the case in desert areas. With the help of high-speed wind, sand particles may impinge on the surface with high potential energy. Sand blasting is considered as a very aggressive test and thus the coating on the central area of sample B1-3 was removed and only the edge areas were found to have a water contact angle of about 1200, as shown in FIG. 40. After sand blasting, sample center becomes hydrophilic due to the removal of the coating by high speed sand particles, while the area on the edge remains still hydrophobic and water still can roll off the surface rather than spread on it.

Example 10—Application of Developed Solutions to Different Substrates

Figures 41A, 41B, 41C:
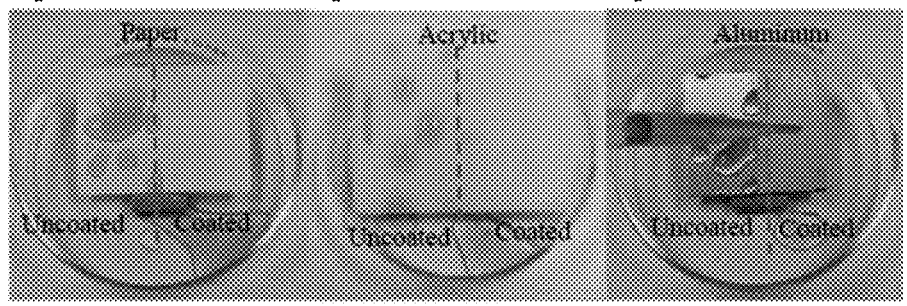
FIG. 41A is an image of a superhydrophobic coating, wherein the substrate is paper.
FIG. 41B is an image of a superhydrophobic coating, wherein the substrate is acrylic.
FIG. 41C is an image of a superhydrophobic coating, wherein the substrate is aluminum.
Figures 41D, 41E, 41F:
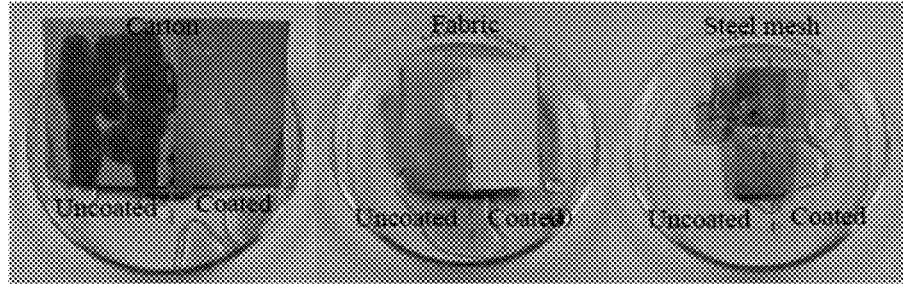
FIG. 41D is an image of a superhydrophobic coating, wherein the substrate is carton.
FIG. 41E is an image of a superhydrophobic coating, wherein the substrate is fabric.
FIG. 41F is an image of a superhydrophobic coating, wherein the substrate is steel mesh.

FIG. 41 shows that once the desired solutions (sol A and sol B) are prepared, the resulting coating can be applied successfully to any substrate, making it superhydrophobic.

Paper, acrylic sheet, aluminum, carton, fabric cloth and steel mesh half were coated first with sol A and followed by sol B as explained in methodology part. It is clear from the FIG. 41 that, all of the selected substrates were showing superhydrophobic nature after treatment. The developed coating solutions in this research can be applied to various substrates mainly because of first layer behaves as adhesive layer and/or binder. After functionalized silica particles are sprayed on the surface, particles can embed or stably bind to the first layer. It is worth to mention that very few coatings have shown success on a variety of substrates.

To see how water droplets, interact with the fabricated superhydrophobic surfaces and hydrophilic (uncoated) surface, water droplet motion was recorded by camera. A water droplet of about 7 μl and was dropped from a height of 10 cm on different coated and uncoated substrates such as paper, cloth (fabric), Aluminum sheet, glass, acrylic sheet, steel mesh. FIG. 42 shows time-lapse photographs of how water droplets behave on the coated and uncoated surfaces of these materials. It is clear from the images that usually on coated superhydrophobic surfaces water droplets are bouncing, thus leading to the conclusion that the developed coating is suitable to be utilized in different applications, not only for PV panels.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method of forming a superhydrophobic coating, comprising:
   mixing a solution comprising an alkyl alkoxysilane, a glycidyl-containing alkoxysilane, an alcohol, ammonium hydroxide, and water for 20 to 60 minutes to form a mixture and applying the mixture onto a substrate;
   heating the substrate and the mixture applied thereon, wherein the substrate is functionalized with the alkyl alkoxysilane and the glycidyl-containing alkoxysilane, thereby forming a coated substrate comprising a binding layer on the substrate;
   applying a suspension comprising perfluoroalkyl-functionalized silica nanoparticles onto the coated substrate to form a hydrophobic layer on the binding layer, thereby forming the superhydrophobic coating; and
   annealing the substrate with the superhydrophobic coating at a temperature in the range of 100° C. to 300° C. for no more than 2 hours,
   wherein the alkyl alkoxysilane is selected from the group consisting of methytrimethoxysilane, methyltriethoxysilane, ethyltrimethoxysilane, trimethylethoxysilane, and dimethyldiethoxysilane, and
   wherein the glycidyl-containing alkoxysilane is (3-glycidyloxypropyl) trimethoxysilane.

2. The method of claim 1,
   wherein the mixture is applied onto the substrate by spray-coating, and
   wherein the suspension is applied onto the coated substrate by spray-coating.

3. The method of claim 1, wherein the substrate and the mixture applied thereon are heated at a temperature of 30 to 90° C. for no more than 3 hours.

4. The method of claim 1, wherein a weight percent of the perfluoroalkyl-functionalized silica nanoparticles in the suspension is in the range of 0.1 wt % to 2.0 wt %, relative to the total weight of the suspension.

5. The method of claim 1,
   wherein a molar ratio of the glycidyl-containing alkoxysilane to the alkyl alkoxysilane in the solution is from 1:1 to 1:5, and
   wherein a molar ratio of the alkyl alkoxysilane to the water in the solution is from 1:3 to 1:6.

6. The method of claim 1, wherein the perfluoroalkyl-functionalized silica nanoparticles in the suspension are formed by sonicating silica nanoparticles in the presence of a perfluoroalkylsilane.

7. The method of claim 6, wherein the perfluoroalkylsilane is 1,1,2,2-perfluorooctyltriethoxysilane.

8. The method of claim 6, wherein an average diameter of the silica nanoparticles is in the range of 1 to 100 nm.

9. The method of claim 1, wherein three layers of the mixture are applied onto the substrate by spray-coating.

10. The method of claim 1, wherein the mixture is applied onto the substrate by spray-coating at a spray distance of 14 to 16 cm.

11. The method of claim 1, wherein the mixture is applied onto the substrate with spray-coating with a pressure of 200 to 400 kPa.

12. The method of claim 1, wherein three layers of the suspension are applied onto the coated substrate by spray-coating.

13. The method of claim 1, wherein a weight percent of the perfluoroalkyl-functionalized silica nanoparticles in the suspension is in the range of 0.1 wt % to 1.0 wt %, relative to the total weight of the suspension.

14. The method of claim 1, wherein the suspension is applied onto the coated substrate by spray-coating at a spray distance of 14 to 16 cm.

15. The method of claim 1, wherein the suspension is applied onto the coated substrate by spray-coating with a pressure of 200 to 400 kPa.

16. The method of claim 1, wherein the suspension consists of the perfluoroalkyl-functionalized silica nanoparticles in an alcohol solvent.

\* \* \* \* \*